United States Patent
Hohlfeld et al.

(10) Patent No.: US 12,187,749 B2
(45) Date of Patent: Jan. 7, 2025

(54) APPLICATION OF DIPYRRINATO-IRIDIUM COMPLEXES IN ANTI-TUMOR AND ANTI-BACTERIAL THERAPY

(71) Applicant: BIOLITEC UNTERGEHMENSBETEILIGUNGS II AG, Vienna (AT)

(72) Inventors: Benjamin Florian Hohlfeld, Berlin (DE); Arno Wiehe, Berlin (DE); Burkhard Gitter, Jena (DE); Dorika Steen, Jena (DE); Gerhard Wieland, Jena (DE); Volker Albrecht, Nuthetal (DE)

(73) Assignee: BIOLITEC UNTERNEHMENSBETEILIGUNGS III AG, Vienna (AT)

( * ) Notice: Subject to any disclaimer, the term of this patent is extended or adjusted under 35 U.S.C. 154(b) by 0 days.

(21) Appl. No.: 18/162,205

(22) Filed: Jan. 31, 2023

(65) Prior Publication Data
US 2023/0242559 A1    Aug. 3, 2023

Related U.S. Application Data

(63) Continuation of application No. PCT/EP2021/071590, filed on Aug. 2, 2021.

(60) Provisional application No. 63/060,572, filed on Aug. 3, 2020.

(51) Int. Cl.
| | |
|---|---|
| C07F 15/00 | (2006.01) |
| A61K 41/00 | (2020.01) |
| A61K 47/54 | (2017.01) |
| A61P 31/04 | (2006.01) |
| A61P 35/00 | (2006.01) |
| C07F 17/02 | (2006.01) |

(52) U.S. Cl.
CPC ...... *C07F 15/0033* (2013.01); *A61K 41/0057* (2013.01); *A61K 47/549* (2017.08); *A61P 31/04* (2018.01); *A61P 35/00* (2018.01); *C07F 17/02* (2013.01)

(58) Field of Classification Search
CPC .. C07F 15/0033; C07F 17/02; A61K 41/0057; A61K 47/549; A61K 49/0021; A61P 31/04; A61P 35/00; A61P 29/00
See application file for complete search history.

(56) References Cited

PUBLICATIONS

Hohlfeld et al. Dipyrrinato-Iridium(III) complexes for application in photodynamic therapy and antimicrobial photodynamic inactivation, (Chemistry-A European Journal, 27, 6440-6459). (Year: 2021).*
Takaki et al. Controlling the Electronic Structures and Excited-State Characteristics of dipyrrinatoiridium(III) complexes by an arylborane or an arylamino unit (Inorg. Chem. 58, 14542-14550). (Year: 2019).*

* cited by examiner

*Primary Examiner* — Matthew P Coughlin
*Assistant Examiner* — Meghan C Heasley
(74) *Attorney, Agent, or Firm* — McCormick, Paulding & Huber PLLC

(57) ABSTRACT

Biologically active compounds and their methods of preparation are provided that may be used as photosensitizers for diagnostic and therapeutic applications, particularly for PDT of cancer, infections and other hyperproliferative diseases, fluorescence diagnosis and PDT treatment of non-tumorous indications such as arthritis, inflammatory diseases, viral or bacterial infections, dermatological, otorhinolaryngology disorders, ophthalmological or urological disorders. As the compounds exhibit also toxicity against targets (tumor cells, bacteria inflammation-related cells) without light these biologically active compounds may also be used for the light-independent treatment of such indications. Embodiments also include methods to synthesize iridium(III) complex structures incorporating a substituted 2,3,5,6-tetrafluorophenyl-dipyrromethene (2,3,5,6-tetratfluorophenyldipyrrin) unit or a substituted 3-nitrophenyl-dipyrromethene (3-nitrophenyl-dipyrrin) unit. Amphiphilic compounds with increased anti-tumour and anti-bacterial efficacy are also provided. Specifically, this is achieved by substitution with bromine atoms and sugar moieties.

12 Claims, 17 Drawing Sheets

Test against *S. aureus.*

Test against *Pseudomonas aeruginosa*.

Test against *S. aureus*.

Test against *Pseudomonas aeruginosa*.

Test against *S. aureus*.

Test against *Pseudomonas aeruginosa*.

Test against *S. aureus*.

Test against *Pseudomonas aeruginosa*.

Test against *S. aureus*.

Test against *S. aureus*.

Test against *S. aureus*.

Test against *S. aureus*.

Test against *S. aureus*.

Test against S. aureus.

Test against S. aureus.

Test against *S. aureus*.

Test against *S. aureus*.

Test against *S. aureus*.

APPLICATION OF DIPYRRINATO-IRIDIUM COMPLEXES IN ANTI-TUMOR AND ANTI-BACTERIAL THERAPY

CROSS REFERENCE TO PRIORITY APPLICATION

This patent application claims priority to U.S. provisional patent application No. 63/060,572, filed on Aug. 3, 2020, by Hohlfeld et al. entitled, "APPLICATION OF DIPYRRINATO-IRIDIUM COMPLEXES IN ANTI-TUMOR AND ANTI-BACTERIAL THERAPY", which is hereby expressly incorporated by reference in its entirety as part of the present disclosure.

TECHNICAL FIELD

The invention relates to the chemistry of biologically active compounds. More particularly it relates to certain dipyrrinato-iridium complexes that can be used to treat tumorous diseases as well as bacterial infections and other diseases including viral infections. The action of these dipyrrinato-iridium complexes against tumor cells and bacteria as well as viruses may be intensified by light, thus they can also be used as photosensitizers for a wide range of light irradiation treatments such as photodynamic therapy of cancer, infections and other diseases.

BACKGROUND

Cancer is one of the main causes of death worldwide. Though many therapeutic approaches are known there is still need for new active substances and therapies that can be applied to tumors which cannot successfully be treated by conventional chemotherapeutics. One of those newer therapeutic approaches is photodynamic therapy (PDT). PDT is now being explored for use in a variety of medical applications [1], and particularly is a well-recognized treatment for the destruction of tumors [2]. Photodynamic therapy uses light and a photosensitizer (a dye) to achieve its desired medical effect. A large number of naturally occurring and synthetic dyes have been evaluated as potential photosensitizers for PDT. Perhaps the most widely studied class of photosensitizers is tetrapyrrolic macrocyclic compounds. Among them, especially porphyrins and chlorins have been tested for their PDT efficacy. However, there is constant interest in new photosensitizer structures among them metal complexes like e.g certain ruthenium complexes [3].

The photodynamic effect is only observed where the three necessary components, the photosensitizer, light and oxygen (which is present in the cells) are present at the same time [1]. This makes PDT by itself a local treatment which is opposed to the systemic action of chemotherapeutics. This localized treatment with PDT limits its efficacy mostly to localized tumors though recent reports also suggest a systemic, immunomodulating effect of PDT [4].

Another field of application for PDT is the antibacterial PDT that is the application of photosensitizers and light against localized bacterial infections. Bacteria are generally divided into two main groups based on the different properties and construction of their outer membranes, i.e. Gram-positive and Gram-negative bacteria. For antibacterial PDT other dyes than for tumor therapy have been employed. Whereas for antitumor PDT amphiphilic photosensitizers have proven to be most effective, for antibacterial PDT usually more hydrophilic and water-soluble dyes have been employed [5]. Specifically, for antibacterial PDT against Gram-negative bacteria water-soluble positively charged photosensitizers have been used [5].

SUMMARY

Embodiments include biologically active compounds that can be used as photosensitizers for a wide range of applications including light irradiation treatments such as PDT of cancer, infections and other diseases. One of the limitations of current PDT is the localized effect of the treatment, which is due to the fact, that light has to be delivered to the treatment site. This could be overcome by compounds which act as photosensitizers but additionally exhibit a light-independent toxicity against e.g. tumor cells or bacteria. Therefore, the structures described herein are active as photosensitizers but may also be used for a systemic treatment due to their light-independent toxicity against e.g. tumor cells or bacteria. In addition, due to their light-absorbing and light-emitting properties these compounds may also be employed for diagnostic purposes e.g. by detecting their luminescence.

Embodiments include chemically stable dipyrrinato-iridium complexes useful for various medical applications such as photodynamic therapy. Yet, these compounds may also be used for the treatment of tumorous and other diseases without having to administer light, thereby also enabling a systemic treatment.

Embodiments include iridium complex structures incorporating a substituted 2,3,5,6-tetrafluorophenyl-dipyrromethene (2,3,5,6-tetrafluorophenyl-dipyrrin) unit or a substituted 3-nitrophenyl-dipyrromethene (3-nitrophenyl-dipyrrin) unit that can be used in the photodynamic therapy of tumors and other hyperproliferative diseases, dermatological disorders, viral or bacterial infections, otorhinolaryngology disorders, ophthalmological disorders or urological disorders. These compounds may also be used in the therapy of tumors and other hyperproliferative diseases, dermatological disorders, viral or bacterial infections, otorhinolaryngology disorders, ophthalmological disorders or urological disorders without the necessity to administer light. Still, these compounds may also be used in light-based diagnostics of tumors, hyperproliferative diseases, dermatological disorders, bacterial infections, otorhinolaryngology disorders, ophthalmological disorders or urological disorders. These compounds may also be used for the fluorescence diagnosis and PDT treatment of a non-tumorous indication such as arthritis and similar inflammatory diseases.

Embodiments include amphiphilic compounds that may be used in the PDT-treatment of tumors, dermatological disorders, viral or bacterial infections, otorhinolaryngology disorders, ophthalmological disorders or urological disorders; and also may be used in the treatment of tumors, dermatological disorders, viral or bacterial infections, otorhinolaryngology disorders, ophthalmological disorders or urological disorders without the necessity to administer light.

Embodiments include pharmaceutically acceptable formulations for the biologically active compounds herein described, such as a liposomal formulation to be injected avoiding undesirable effects like precipitation at the injection site or delayed pharmacokinetics of the compounds.

Briefly stated, embodiments include biologically active compounds and methods to obtain biologically active compounds that can be used as photosensitizers for diagnostic and therapeutic applications, particularly for PDT of cancer, infections and other hyperproliferative diseases, fluorescence diagnosis and PDT treatment of non-tumorous indications such as arthritis, inflammatory diseases, viral or bacterial infections, dermatological, otorhinolaryngology disorders, ophthalmological or urological disorders. As the compounds exhibit also toxicity against targets (tumor cells, bacteria, inflammation-related cells) without light, these biologically active compounds may also be used for the light-independent treatment of such indications. Embodiments also include methods to synthesize iridium complex structures incorporating a substituted 2,3,5,6-tetrafluorophenyl-dipyrromethene (2,3,5,6-tetrafluorophenyl-dipyrrin) unit or a substituted 3-nitrophenyl-dipyrromethene (3-nitrophenyl-dipyrrin) unit. These dipyrromethenes (dipyrrins) may carry a variety of different substituents in the 4-position enabling a fine tuning of their biological or amphiphilic/hydrophilic properties. Embodiments also include compounds with increased anti-tumour and anti-bacterial efficacy. Specifically, this is achieved by substitution with bromine atoms and sugar moieties.

The above and other objects, features and advantages of the present invention will become apparent from the following description read in conjunction with the accompanying drawings.

DETAILED DESCRIPTION OF EMBODIMENTS

Figure 1:
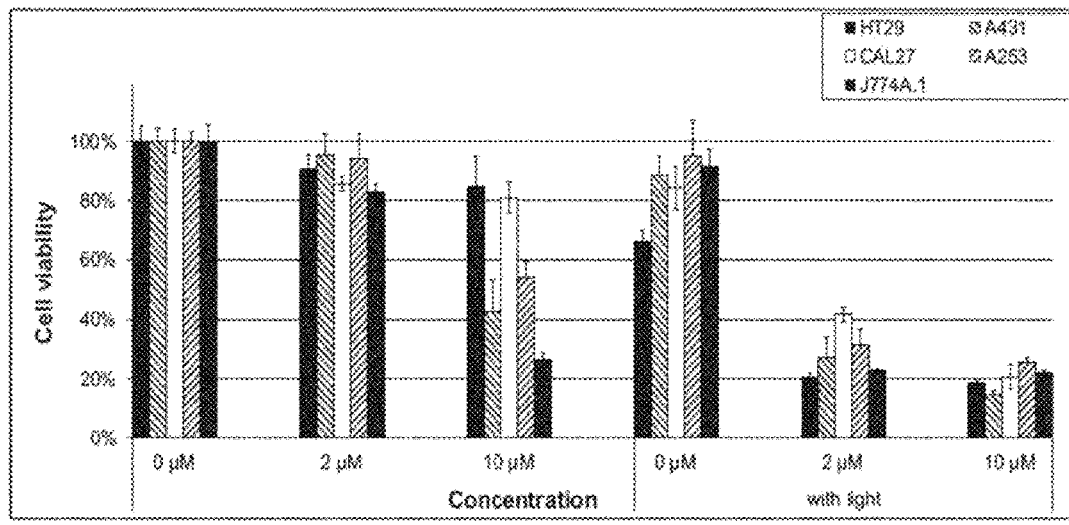
FIG. 1 illustrates the photodynamic activity ('with light' means phototoxicity) of chlorido(5-pentafluorophenyl-dipyninato)-(pentamethylcyclopentadienyl)-iridium(III) tested in selected cell lines.

Embodiments include biologically active compounds that may be used as photosensitizers for a wide range of light irradiation treatments such as PDT of cancer, hyperproliferative diseases, dermatological disorders, viral or bacterial infectious diseases, otorhinolaryngology disorders, ophthalmological disorders and/or urological disorders. Due to their light-independent toxicity they may also be used for the therapy of such diseases without the necessity to administer light. The compounds described herein have the advantage that they are easily produced and characterized, and allow further functionalization to enhance their activity, stability or make new applications possible. Embodiments also include methods to tailor compounds for desired applications, to increase target tissue selectivity and thus therapeutic efficacy. The compounds herein described enhance the effectiveness of biologically active compounds compared to the compounds described in prior art, by allowing to combine PDT and conventional chemotherapeutic or antibacterial treatment and by enhancing selectivity for target tissues over healthy surrounding tissues due to their tailored molecular structures and custom-made pharmacokinetic behavior depending on the particular application. Moreover, the compounds according to present disclosure may be loaded onto the surfaces of medical devices to provide an antitumor or antibacterial effect, or to aid in visualization in diagnostic tools. The compounds may be loaded with conventional techniques known in the art.

Embodiments include biologically active compounds that may be used for different medical indications and treatments, among them PDT, are iridium complex structures incorporating a substituted 2,3,5,6-tetrafluorophenyl-dipyrromethene (2,3,5,6-tetrafluorophenyl-dipyrrin) unit or a substituted 3-nitrophenyl-dipyrromethene (3-nitrophenyl-dipyrrin) unit, preferably iridium(III) complex structures. In addition, these compounds may be employed for fluorescence diagnosis and the treatment of non-tumorous indications such as arthritis and similar inflammatory diseases, extending their applications.

To obtain the novel compounds, embodiments use substituted dipyrromethanes (dipyrranes) which are converted to the corresponding dipyrromethenes (dipyrrins). This conversion is done by treating the corresponding dipyrromethane (dipyrrane) with a suitable oxidizing agent like DDQ or p-chloranil [6,7]. In one embodiment a 2,3,4,5,6-pentafluorophenyl-dipyrromethane or a 4-fluoro-3-nitrophenyl-dipyrromethane is treated with a suitable nucleophile (oxygen, nitrogen or sulfur nucleophiles) yielding the 4-substituted 2,3,5,6-tetrafluorophenyl-dipyrromethanes or the 4-substituted-3-nitrophenyl-dipyrromethanes, which are subsequently oxidized to the dipyrromethenes.

These dipyrromethenes (dipyrrins) are then reacted with a suitable iridium complex precursor compound, e.g. (cyclopentadienyl)iridium chloride dimer, to obtain the corresponding chlorido(cyclopentadienyl)dipyrrinato-iridium (III) complexes. In another embodiment the dipyrromethenes (dipyrrins) are reacted with bis(phenylpyridyl)iridium chloride dimer, to obtain the corresponding bis(phenylpyridyl)dipyrrinato-iridium(III) complexes.

Alternatively, the 2,3,4,5,6-pentafluorophenyl-dipyrromethane or the 4-fluoro-3-nitrophenyl-dipyrromethane, is first reacted with the bis(phenylpyridyl)iridium chloride dimer to obtain the corresponding ([(pentafluorphenyl)-2,2-dipyrrylmethyl]bis(phenyl-2-pyridyl))iridium(III) complex and the {[(4-fluoro-3-nitrophenyl)-2,2-dipyrrylmethyl]-bis(phenyl-2-pyridyl)}iridium(III) complex, respectively. These complexes are then modified via nucleophilic aromatic substitution in the 4-position of the phenyl ring with a suitable nucleophile, specifically oxygen, nitrogen or sulfur nucleophiles carrying sugar moieties.

In a specifically preferred embodiment of the present disclosure the sulfur nucleophile is a sugar thiol compound, e.g. galactosyl-thiol or glucosyl-thiol.

Acceptable starting materials for the synthesis of the iridium complexes described herein may be dipyrromethanes (dipyrranes) which are readily accessible from the condensation reaction of pyrroles and aldehydes [8]. Suitable methods for this condensation have long been known in the art [8]. The dipyrromethane (dipyrrane) may then be modified with nucleophiles according to the literature [9]. The dipyrromethanes (dipyrranes)—whether modified with nucleophiles of not—may then be converted to the corresponding iridium complexes. The pyrrole used for the condensation to the dipyrromethane may be unsubstituted or substituted by methyl groups. Modification of the iridium complexes with sugar moieties may be achieved by the substitution of the para-fluorine atom of the 2,3,4,5,6-pentafluorophenyl or the 4-fluoro-3-nitrophenyl-substituent with suitable sugar nucleophiles which has been described for other pentafluorophenyl-substituted compounds in the literature, e.g. galactosyl-thiol or glucosyl-thiol [10]. The synthesis of compounds described herein is illustrated with the examples given below.

Example 1 shows the synthesis of chlorido(cyclopentadienyl)dipyrrinato-iridium(III) complexes, including those with substituted with methyl groups at the dipyrrin unit.

Example 2 shows the synthesis of bis(phenylpyridyl)dipyrrinato-iridium(III) complexes via the reaction of substituted dipyrromethenes (dipyrrins) with bis(phenylpyridyl) iridium chloride dimer.

Example 3 shows the synthesis of {[(pentafluorphenyl)-2,2-dipyrrylmethyl]bis(phenyl-2-pyridyl)}iridium(III) and {[(4-fluoro-3-nitrophenyl)-2,2-dipyrrylmethyl]-bis(phenyl-2-pyridyl)}iridium(III) and their subsequent modification via nucleophilic aromatic substitution.

Embodiments include an iridium compound based on the formulas 1, 2, 3 or 4:

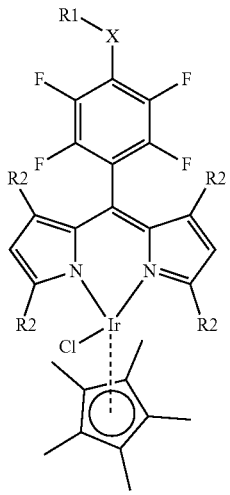

1

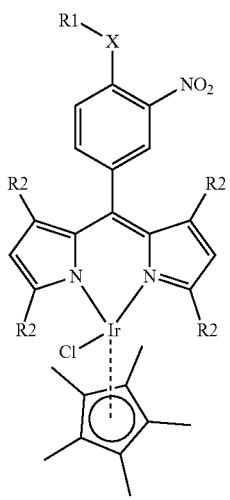

2

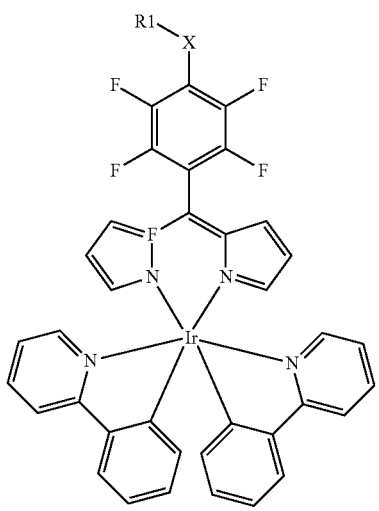

3

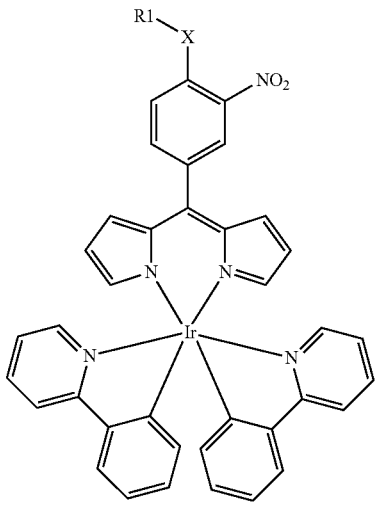

4 wherein X is at least one of O, NH or S; $R^1$ is at least one of a carbohydrate moiety, a short alkyl chain with 3 to 6 carbon atoms, propargyl, HO—$CH_2$—$CH_2$—, $CH(CH_2OH)_2$, $CH_2$—CH(OH)—$CH_2OH$, or CH(OH)—CH(OH)—$CH_3$; and $R^2$ is at least one of hydrogen or a methyl group. The iridium compounds or a pharmaceutically acceptable derivative thereof may be used in therapy and/or in the photodynamic therapy of at least one of tumors, dermatological disorders, viral infections, bacterial infections, otorhinolaryngology disorders, ophthalmological disorders or urological disorders. The iridium compounds or a pharmaceutically acceptable derivative thereof may be used in the preparation of a pharmaceutical composition for use in therapy or photodynamic therapy of tumors and/or arthritis and similar inflammatory diseases, and for use in the diagnosis of arthritis and similar inflammatory diseases or in the diagnosis of tumors. In some instances, the iridium compounds or a pharmaceutically acceptable derivative thereof may be loaded onto a surface of a medical device. A pharmaceutical composition may comprise the iridium compounds described herein or a pharmaceutically acceptable derivative thereof as an active ingredient. In some embodiments, the compound is conjugated to a targeting agent, and the targeting agent may be a peptide.

The specifically substituted iridium complexes as herein described are suitable to be used for the chemotherapy of cancer and other (hyper) proliferative diseases and infections as well as for the photodynamic therapy of those diseases, infections and conditions.

In some embodiments, treatment is accomplished by first incorporating the iridium complexes into a pharmaceutically acceptable application vehicle (e.g. ethanolic solution, liposomal formulation, or another pharmaceutical formulation) for delivery of the derivatives to a specific treatment site. After administering the derivatives in the vehicle to a treatment area, sufficient time is allowed so that the complexes preferentially accumulate in the diseased tissue and exert their effect. In case of PDT treatment, the treatment area is irradiated with light of a proper wavelength and sufficient power to activate the iridium dipyrromethene complexes to induce necrosis or apoptosis in the cells of said diseased tissue. Due to their amphiphilic nature, the chemically stable iridium dipyrromethene complexes according to embodiments of the present disclosure may be prepared in various pharmaceutically acceptable and active preparations for different administration methods, e.g. injections. In one embodiment such amphiphilic compounds are formulated into liposomes. This liposomal formulation can then be injected avoiding undesirable effects such as precipitation at the injection site or delayed pharmacokinetics.

Determination of dark toxicity (DT) and phototoxicity (example 4) of the iridium dipyrromethene complexes as described in present disclosure in cell culture experiments with the HT29 tumor cell line and other cell lines shows the excellent properties of the compounds for use in PDT (FIGS. 1 to 15 and examples 4.1 to 4.15).

The data presented in FIGS. 1 to 15 corresponding to examples 4.1 to 4.15 also show the results of the photodynamic treatment in a model cell line especially relevant for arthritis (J774A.1, a macrophage cell line) with compounds described in present disclosure, demonstrating the usefulness of the disclosed iridium complexes in the diagnosis and treatment of arthritis and similar inflammatory diseases.

The FIGS. 16 to 29 corresponding to example 5 (5.1 to 5.14) illustrate the effect of iridium complexes described herein against bacteria, the Gram-positive germ *Staphylococcus aureus* (5.1 to 5.14) as well as the Gram-negative *Pseudomonas aeruginosa* (5.1 to 5.4), proving that these compounds may also be used to treat bacterial infections. As can be seen from the examples, selected compounds (5.1 to 5.6, 5.8, 5.11, 5.12) show a high antibacterial activity against *S. aureus* even in the absence of light exemplifying their principal suitability for a systemic treatment, especially since the compounds are on the other hand non-toxic to cells in the absence of light (cf. example 4, e.g. 4.2, 4.3, 4.4). For examples 5.1 to 5.7 and 5.12 antibacterial activity is also observed in the presence of complex media (serum addition).

The following examples are presented to provide those of ordinary skill in the art with a full and illustrative disclosure and description of how to make the iridium complexes of the invention and show their chemotherapeutic and photodynamic activity and are not intended to limit the scope of what the inventor regards as the invention. Efforts have been made to ensure accuracy with respect to numbers used (e.g. amounts, temperature etc.), but some experimental errors and deviations should be accounted for. Also, best measures have been taken to name the compounds with their systematic IUPAC name, nevertheless the basic reference are the given structural formulas based on the experimental spectroscopic data.

All reactions were performed in standard round bottom flasks. Air-sensitive reactions were carried out under an argon gas protecting atmosphere. DCM, n-pentane, and methanol were purchased and used as received. Other solvents were purchased and distilled at reduced pressure. Purchased chemicals were used as received without further purification. All liquid reagents were added through syringes. Reactions were monitored by thin-layer chromatography (Merck, TLC Silica gel 60 $F_{254}$ and visualized under UV light (254 nm and 366 nm). Flash column chromatography was performed on silica gel (Fluka silica gel 60M, 40-63 μm). NMR spectra were recorded with JEOL ECX400, JEOL ECP500, Bruker Avance500, and JEOL ECZ600. Multiplicity of the signals was assigned as follows: s=singlet, br s=broad singlet, d=doublet, t=triplet, dd=doublet of doublets, dt=doublet of triplets, td=triplet of doublets, ddd=doublet of doublets of doublets, m=multiplet. Chemical shifts are reported relative to $CDCl_3$ ($^1H$: J=7.26 ppm, $^{13}C$: δ=77.2 ppm), $CD_2Cl_2$ ($^1H$: δ=5.32 ppm, $^{13}C$: δ=53.8 ppm), $(CD_3)_2CO$ ($^1H$: δ=2.05 ppm, $^{13}C$: δ=29.8 ppm), THF-$d_6$ ($^1H$: δ=3.58 ppm, $^{13}C$: δ=67.6 ppm), and DMSO-$d_6$ ($^1H$: δ=2.50 ppm, $^{13}C$: δ=39.5 ppm). All $^{13}C$ NMR spectra are proton-decoupled and coupling constants are given in hertz (Hz). For a detailed peak assignment 2D spectra were measured (COSY, HMBC, and HMQC). HRMS analyses were carried out on an Agilent Technologies 6210 ESI-TOF (electrospray ionization, time of flight) instrument. UV/Vis spectra were recorded on a SPECORD S300 UV/Vis spectrometer (Analytic Jena) in quartz cuvettes (1 cm length). Specified melting points were recorded on a Reichert Thermovar Apparatus and are not corrected. 5-[4-(N-Butylamino)-2,3,5,6-tetrafluorophenyl] dipyrromethane [11], 5-[4-(N-2-hydroxyethylamino)-2,3,5, 6-tetrafluorophenyl]dipyrromethane [12], 5-(4-fluoro-3-nitrophenyl)dipyrromethane [13], 5-[4-(N,N-dibutylamino)-3-nitrophenyl]dipyrromethane and meso-(4-amino-3-nitrophenyl)-substituted dipyrrins [7], 5-(pentafluorophenyl) dipyrrin [14], 5-(4-butyloxy-2,3,5,6-tetrafluorophenyl) dipyrrin [15], and 5-pentafluorophenyl-1,3,7,9-tetramethyl-dipyrrin [16] were prepared according to the literature.

Example 1

Preparation of Chlorido(Cyclopentadienyl)Dipyrrinato-Iridium(III) Complexes, Including Those with Substituted with Methyl Groups at the Dipyrrin Unit General synthetic procedure for the dipyrrins: The corresponding dipyrromethane (1 equiv.) was dissolved in THF and p-chloranil (1 equiv., suspended in 5 mL of THF) was added. The reaction mixture was stirred for the indicated time at room temperature. Afterwards, the THF was evaporated at reduced pressure, the remaining solid was resolved and filtered over a silica gel filled glass frit. The filtrate was evaporated to dryness and purified by column chromatography.

General synthetic procedure for the chlorido(cyclopentadienyl)dipyrrinato-iridium(III) complexes: The corresponding dipyrrin (1 equiv.) and N,N-diisopropylethylamine (14 equiv.) were dissolved in DCM or THF. The flask was shielded from ambient light with aluminum foil. Di(μ-chlorido)bis[chlorido($\eta^5$-pentamethyl-cyclopendienyl) iridium(III)] (0.5 equiv.) was added and the mixture was stirred for 24 h at room temperature. After the indicated time, saturated NaCl-solution was added to the solution and was extracted with DCM several times. The combined organic layers were dried with $Na_2SO_4$, filtered, and evaporated to dryness. The crude product was purified by column chromatography and recrystallization.

1.1 Chlorido(5-pentafluorophenyldipyrrinato)(pentamethylcyclopentadienyl)iridium(III)

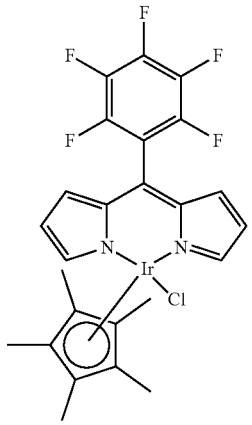

Chlorido(5-pentafluorophenyldipyrrinato)(pentamethylcyclopentadienyl)iridium(III) was prepared according to the general synthetic procedure. 5-(Pentafluorophenyl)dipyrrin (prepared according to the literature [14]) (200 mg, 0.65 mmol), di(μ-chlorido)bis[chlorido($\eta^5$-pentamethylcyclopendienyl)iridium(III)] (257 mg, 0.32 mmol) and N,N-diisopropylethylamine (1.53 mL, 9.03 mmol) were dissolved in 10 mL of DCM. The crude product was purified by column chromatography (silica gel, DCM/EtOAc=9/1, v/v) and recrystallization (DCM/n-hexane) to obtain the product as a red-brown solid (395 mg, 0.59 mmol, 91%).

Mp: >250° C.

$^1$H NMR (500 MHz, CDCl$_3$): δ (ppm)=1.48 (s, 15H, Me$_{Cp*}$), 6.45-6.46 (m, 2H, H$_{pyrrole}$), 6.50 (dd, J=4.4, 1.4 Hz, 2H, H$_{pyrrole}$), 7.69 (t, J=1.3 Hz, 2H, H$_{pyrrole}$).

$^{13}$C NMR (126 MHz, CDCl$_3$): δ (ppm)=8.4 (Me), 86.99 (C$_{Cp*}$), 119.3 (C$_{pyrrole}$), 129.7 (C$_{meso}$), 130.3 (C$_{pyrrole}$), 132.8 (C$_{pyrrole}$), 155.2 (C$_{pyrrole}$).

$^{19}$F NMR (376 MHz, CDCl$_3$): δ (ppm)=-161.62 (ddd, J=21.7, 21.2, 8.0 Hz, 1F, CF$_{ortho}$), -160.54 (ddd, J=21.7, 21.1, 9.0 Hz, 1F, CF$_{ortho}$), -152.72 (t, J=20.8 Hz, 1F, CF$_{ortho}$), -139.87 (dd, J=24.3, 8.5 Hz, 1F, CF$_{meta}$), -137.45 (dd, J=21.4, 7.6 Hz, 1F, CF$_{meta}$).

HRMS (ESI-TOF): m/z calcd. for C$_{25}$H$_{21}$F$_5$IrN$_2$$^+$ [M-Cl]$^+$: 637.1249, found: 637.1267.

1.2 {5-[4-(N-Butylamino)-2,3,5,6-tetrafluorophenyl]dipyrrinato}chlorido-(pentamethylcyclopentadienyl)iridium(III)

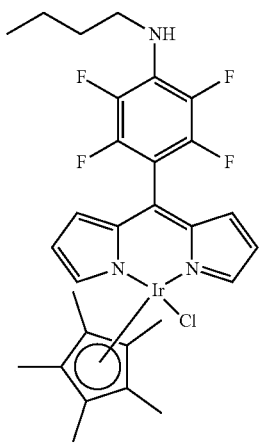

First, 5-[4-(N-butylamino)-2,3,5,6-tetrafluorophenyl]dipyrrin was prepared according to the general synthetic procedure. 5-[4-(N-Butylamino)-2,3,5,6-tetrafluorophenyl]-dipyrromethane (prepared according to the literature [11]) (1.21 g, 3.31 mmol) and p-chloranil (814 mg, 3.31 mmol) were dissolved in 20 mL of THF. The mixture was stirred for 24 h. After evaporation, the solid was resolved in DCM and filtered (DCM). The crude product was purified by column chromatography (silica gel, DCM) to obtain the product as a dark green solid (879 mg, 2.42 mmol, 73%).

Mp: 79-85° C.

$^1$H NMR (500 MHz, CDCl$_3$): δ (ppm)=0.99 (t, J=7.4 Hz, 3H, Me), 1.41-1.50 (m, 2H, CH$_2$), 1.61-1.69 (m, 2H, CH$_2$), 3.46-3.51 (m, 2H, CH$_2$), 3.98 (br s, 1H, NH), 6.41 (dt, J=4.0, 1.0 Hz, 2H, H$_{pyrrole}$), 6.62 (d, J=4.2 Hz, 2H, H$_{pyrrole}$), 7.66 (s, 2H, H$_{pyrrole}$).

$^{13}$C NMR (126 MHz, CDCl$_3$): δ (ppm)=13.9 (Me), 19.95 (CH$_2$), 33.04 (CH$_2$), 45.6 (CH$_2$), 102.2 (Ar—C$_{ipso}$), 118.3 (C$_{pyrrole}$), 131.8 (C$_{pyrrole}$), 145.1 (C$_{pyrrole}$).

$^{19}$F NMR (376 MHz, CDCl$_3$): δ (ppm)=-160.44 (d, J=15.9 Hz, 2F, CF$_{ortho}$), -141.69 (d, J=15.0 Hz, 2F, CF$_{meta}$).

HRMS (ESI-TOF): m/z calcd. for C$_{19}$H$_{18}$F$_4$N$_3$$^+$ [M+H]$^+$: 364.1431, found: 364.1424.

{5-[4-(N-Butylamino)-2,3,5,6-tetrafluorophenyl]dipyrrinato}chlorido(pentamethyl-cyclopentadienyl)iridium(III) was prepared according to the general synthetic procedure. 5-[4-(N-Butylamino)-2,3,5,6-tetrafluorophenyl]dipyrrin (200 mg, 0.55 mmol), di(μ-chlorido)bis[chlorido($\eta^5$-pentamethylcyclopendienyl)iridium(III)] (219 mg, 0.28 mmol) and N,N-diisopropylethylamine (1.31 mL, 7.71 mmol) were dissolved in 10 mL of DCM. The crude product was purified by column chromatography (silica gel, DCM/EtOAc=9/1, v/v) and recrystallization (DCM/n-hexane) to obtain the product as a dark red solid (142 mg, 0.20 mmol, 36%).

Mp: 179-186° C.

$^1$H NMR (500 MHz, CDCl$_3$): δ (ppm)=0.98 (t, J=7.4 Hz, 3H, Me$_{butyl}$), 1.43-1.48 (m, 17H, CH$_2$+Me$_{Cp*}$), 1.61-1.66 (m, 2H, CH$_2$), 3.45-3.48 (m, 2H, CH$_2$), 3.91 (m, 1H, NH), 6.47 (dd, J=4.4, 1.4 Hz, 2H, H$_{pyrrole}$), 6.56 (d, J=4.3 Hz, 2H, H$_{pyrrole}$), 7.65 (s, 2H, H$_{pyrrole}$).

$^{13}$C NMR (126 MHz, CDCl$_3$): δ (ppm)=8.3 (Me$_{Cp*}$), 13.9 (Me$_{butyl}$), 19.96 (CH$_2$), 33.1 (CH$_2$), 45.7 (CH$_2$), 86.8 (C$_{Cp*}$), 110.3 (Ar—C$_{ipso}$), 118.7 (C$_{pyrrole}$), 120.0 (C$_{meso}$), 130.8 (C$_{pyrrole}$), 133.8 (C$_{pyrrole}$), 154.4 (C$_{pyrrole}$).

$^{19}$F NMR (376 MHz, CDCl$_3$): δ (ppm)=-161.08 (d, J=22.8 Hz, 1F, CF$_{ortho}$), -159.99 (d, J=23.4 Hz, 1F, CF$_{ortho}$), -143.18 (dd, J=22.8, 7.8 Hz, 1F, CF$_{meta}$), -140.99 (dd, J=22.5, 8.3 Hz, 1F, CF$_{meta}$).

HRMS (ESI-TOF): m/z calcd. for C$_{29}$H$_{31}$F$_4$IrN$_3$$^+$ [M-Cl]$^+$: 690.2078, found: 690.2071.

UV/Vis (DCM): λ$_{max}$ (nm) [log (ε/L mol$^{-1}$ cm$^{-1}$)]=461 [4.13], 516 [4.06].

1.3 [5-(4-Butyloxy-2,3,5,6-tetrafluorophenyl)dipyrrinato]chlorido-(pentamethylcyclopentadienyl)iridium(III)

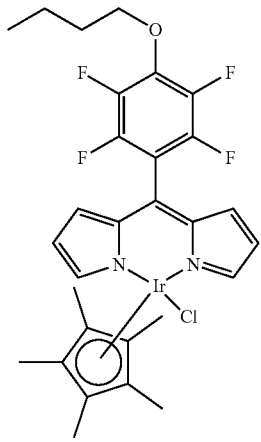

[5-(4-Butyloxy-2,3,5,6-tetrafluorophenyl)dipyrrinato]chlorido(pentamethyl-cyclopentadienyl)iridium(III) was prepared according to the general synthetic procedure. 5-(4-Butyloxy-2,3,5,6-tetrafluorophenyl)dipyrrin (prepared according to the literature [15]) (200 mg, 0.55 mmol), di(s-chlorido)bis[chlorido($\eta^5$-pentamethylcyclopendienyl)iridium(III)] (219 mg, 0.28 mmol) and N,N-diisopropylethylamine (1.31 mL, 7.69 mmol) were dissolved in 10 mL of DCM. The crude product was purified column chromatography (silica gel, DCM, then DCM/EtOAc=9/1, v/v) and recrystallization (DCM/n-hexane) to obtain the product as a dark red solid (341 mg, 0.47 mmol, 86%).

Mp: 200-204° C.

$^1$H NMR (500 MHz, CDCl$_3$): δ (ppm)=0.99 (t, J=7.5 Hz, 3H, Me$_{butyl}$), 1.47 (s, 15H, Me$_{Cp*}$), 1.52-1.58 (m, 2H, CH$_2$), 1.79-1.84 (m, 2H, CH$_2$), 4.32 (t, J=6.5 Hz, 2H, CH$_2$), 6.47 (dd, J=4.4, 1.4 Hz, 2H, H$_{pyrrole}$), 6.56 (d, J=4.4 Hz, 2H, H$_{pyrrole}$), 7.65 (t, J=1.3 Hz, 2H, H$_{pyrrole}$).

$^{13}$C NMR (126 MHz, CDCl$_3$): δ (ppm)=8.3 (Me$_{Cp*}$), 13.8 (Me$_{butyl}$), 18.9 (CH$_2$), 32.1 (CH$_2$), 75.3 (CH$_2$), 86.9 (C$_{Cp*}$), 110.1 (Ar—C$_{Cp*}$), 119.0 (C$_{pyrrole}$), 130.5 (C$_{pyrrole}$), 131.1 (C$_{meso}$), 133.2 (C$_{pyrrole}$), 154.8 (C$_{pyrrole}$).

$^{19}$F NMR (376 MHz, CDCl$_3$): δ (ppm)=−157.41 (dd, J=23.8, 7.8 Hz, 1F, CF$_{ortho}$), −156.18 (dd, J=22.4, 8.7 Hz, 1F, C$_{ortho}$), −141.90 (dd, J=23.9, 9.1 Hz, 1F, CF$_{meta}$), −139.60 (dd, J=22.3, 8.7 Hz, 1F, CF$_{meta}$).

HRMS (ESI-TOF): ma calcd. for C$_{29}$H$_{30}$F$_4$IrN$_2$O$^+$ [M−Cl]$^+$: 691.1918, found: 691.1937.

UV/Vis (DCM): λ$_{max}$ (nm) [log (ε/L mol$^{-1}$ cm$^{-1}$)]=464 [4.25], 514 [4.14].

1.4 {5-[4-(N-Butylamino)-3-nitrophenyl]dipyrrinato}chlorido(pentamethyl-cyclopentadienyl)iridium(III)

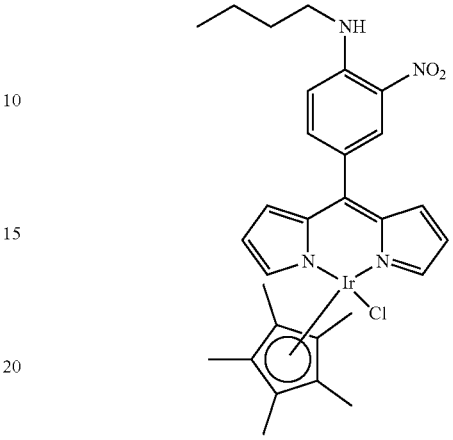

{5-[4-(N-Butylamino)-3-nitrophenyl]dipyrrinato} chlorido(pentamethyl-cyclopentadienyl)iridium(III) was prepared according to the general synthetic procedure. 5-[4-(N-Butylamino)-3-nitrophenyl]dipyrrin (prepared according to the literature [7]) (200 mg, 0.60 mmol), di(μ-chlorido)bis [chlorido($\eta^5$-pentamethylcyclopendienyl)iridium(III)] (237 mg, 0.30 mmol), and N,N-diisopropylethylamine(1.42 mL, 8.32 mmol) were dissolved in 10 mL of THF. The crude product was purified by column chromatography (silica gel, DCM/EtOAc=9/1, v/v) and recrystallization (DCM/n-pentane) to obtain the product as a red solid (192 mg, 0.27 mmol, 46%).

Mp: 221-225° C.

$^1$H NMR (500 MHz, CDCl$_3$): δ (ppm)=1.02 (t, J=7.3 Hz, 3H, Me$_{butyl}$), 1.48-1.57 (m, 17H, CH$_2$+Me$_{Cp*}$), 1.73-1.81 (m, 2H, CH$_2$), 3.35-3.40 (m, 2H, CH$_2$), 6.46 (d, J=3.5, 2H, H$_{pyrrole}$), 6.58 (d, J=4.0 Hz, 2H, H$_{pyrrole}$), 6.90 (d, J=8.8 Hz, 11H, Ar—H$_{meta}$), 7.51 (dd, J=8.8, 2.1 Hz, 1H, Ar—H$_{ortho}$), 7.67 (t, J=1.4 Hz, 2H, H$_{pyrrole}$), 8.20-8.22 (m, 1H, NH), 8.25 (d, J=2.1 Hz, 1H, Ar—H$_{ortho}$).

$^{13}$C NMR (126 MHz, CDCl$_3$): δ (ppm)=8.6 (Me$_{Cp*}$), 13.9 (Me$_{butyl}$), 20.4 (CH$_2$), 31.1 (CH$_2$), 43.1 (CH$_2$), 86.8 (C$_{Cp*}$), 113.1 (Ar—C$_{meta}$), 118.3 (C$_{pyrrole}$), 124.9*, 128.4 (Ar—C$_{ortho}$), 130.9*, 131.4 (C$_{pyrrole}$), 133.3 (C$_{pyrrole}$), 138.5 (Ar—C$_{ortho}$), 144.9 (C$_{meso}$), 145.7 (Ar—C$_{para}$), 153.7 (C$_{pyrrole}$). *These signals could not be assigned exactly to corresponding carbon atoms. They belong to the Ar—C$_{ipso}$ and the Ar—C$_{nitro}$ of the aryl residue.

HRMS(ESI-TOF): m/z calcd. for C$_{29}$H$_{34}$IrN$_4$O$_2^+$ [M−Cl]$^+$: 663.2306, found: 663.2332, m/z calcd. for C$_{58}$H$_{68}$ClIr$_2$N$_8$O$_4^+$ [2M−Cl]$^+$: 1361.4305, found: 1361.4278.

UV/Vis (DCM): λ$_{max}$ (nm) [log (ε/L mol$^{-1}$ cm$^{-1}$)]=449 [4.22], 495 [4.11].

1.5 Chlorido{5-[4-(N-6-methoxy-6-oxohexylamino)-3-nitrophenyl]dipyrrinato}-(pentamethylcyclopentadienyl)iridium(III)

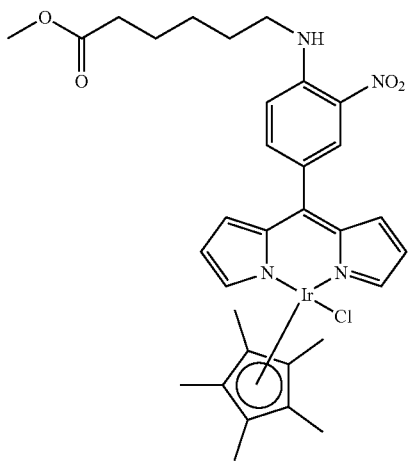

Chlorido{5-[4-(N-6-methoxy-6-oxohexylamino)-3-nitrophenyl]dipyrrinato}-(pentamethylcyclopentadienyl)iridium(III) was prepared according to the general synthetic procedure. 5-[4-(N-6-Methoxy-6-oxohexylamino)-3-nitrophenyl]dipyrrin (prepared according to the literature [7]) (200 mg, 0.49 mmol), di(µ-chlorido)bis[chlorido($\eta^5$-pentamethylcyclopendienyl)iridium(III)] (195 mg, 0.25 mmol), and N,N-diisopropylethylamine (1.17 mL, 6.86 mmol) were dissolved in 10 mL of THF. The crude product was purified by column chromatography (silica gel, DCM/EtOAc=4/1, v/v) and recrystallization (DCM/n-hexane) to obtain the product as a red solid (198 mg, 0.26 mmol, 52%).

Mp: 135-137° C.

$^1$H NMR (500 MHz, CDCl$_3$): δ (ppm)=1.48-1.55 (m, 17K CH$_2$+Me$_{Cp*}$), 1.70-1.76 (m, 2H, CH$_2$), 1.78-1.84 (m, 2H, CH$_2$), 2.37 (t, J=7.4 Hz, 2H, CH$_2$), 3.38 (td, J=7.1, 5.2 Hz, 2H, CH$_2$), 3.68 (Me), 6.46 (dd, J=4.4, 1.5 Hz, 2H, H$_{pyrrole}$), 6.57 (dd, J=4.4, 1.3 Hz, 2H, H$_{pyrrole}$), 6.89 (d, J=8.9 Hz, 1H, Ar—H$_{meta}$), 7.51 (dd, J=8.8, 2.2 Hz, 1H, Ar—H$_{ortho}$), 7.67 (t, J=1.4 Hz, 2H, H$_{pyrrole}$), 8.19 (t, J=5.2 Hz, 11H, NH), 8.25 (d, J=2.1 Hz, 1H, Ar—H$_{ortho}$).

$^{13}$C NMR (126 MHz, CDCl$_3$): δ (ppm)=8.6 (Me$_{Cp*}$), 24.7 (CH$_2$), 26.7 (CH$_2$), 28.8 (CH$_2$), 33.97 (CH$_2$), 4.1 (CH$_2$), 51.7 (Me), 86.8 (C$_{Cp*}$), 113.0 (Ar—C$_{ortho}$), 118.3 (C$_{pyrrole}$), 125.1*, 128.5 (Ar—C$_{ortho}$), 131.0*, 131.4 (C$_{pyrrole}$), 133.3 (C$_{pyrrole}$), 138.6 (Ar—C$_{ortho}$), 144.8 (C$_{meso}$), 145.6 (Ar—C$_{para}$), 153.7 (C$_{pyrrole}$), 173.99 (CO). *These signals could not be assigned exactly to corresponding carbon atoms. They belong to the Ar-C$_{ipso}$ and the Ar—C$_{nitro}$ of the aryl residue.

HRMS (ESI-TOF): m/z calcd. for C$_{32}$H$_{38}$IrN$_4$O$_4^+$ [M−Cl]$^+$: 735.2517, found: 735.2512.

UV/Vis (DCM): λ$_{max}$ (nm) [log (ε/L mol$^{-1}$ cm$^{-1}$)]=449 [4.38], 497 [4.27].

1.6 Chlorido{5-[4-(N,N-dibutylamino)-3-nitrophenyl]dipyrrinato}(pentamethyl-cyclopentadienyl)iridium(III)

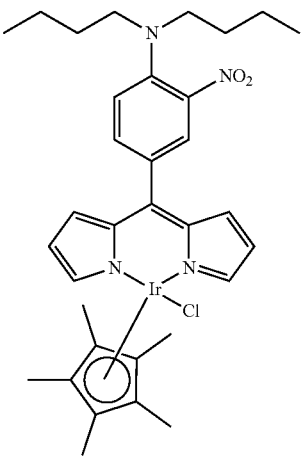

First, 5-[4-(N,N-dibutylamino)-3-nitrophenyl]dipyrrin was prepared according to the general synthetic procedure. 5-[4-(N,N-Dibutylamino)-3-nitrophenyl]dipyrromethane (prepared according to the literature [7]) (1.46 g, 3.70 mmol) and p-chloranil (909 mg, 3.70 mmol) were dissolved in 20 mL of THF. The mixture was stirred for 3 h. After evaporation, the solid was resolved in EtOAc and filtered (EtOAc). The crude product was purified by column chromatography (silica gel, EtOAc) to obtain the product as a dark brown solid (281 mg, 57%).

Mp: 120-126° C.

$^1$H NMR (500 MHz, THF-d$_6$): δ (ppm)=0.92 (t, 1=7.3 Hz, 6H, Me), 1.29-1.40 (m, 4H, CH$_2$), 1.56-1.64 (m, 4H, CH$_2$), 3.23 (t, J=7.4 Hz, 4H, CH$_2$), 6.40 (d, J=4.2 Hz, 2H, H$_{pyrrole}$), 6.66 (d, J=3.9 Hz, 2H, H$_{pyrrole}$), 7.31 (d, J=8.6 Hz, 11H, Ar—H$_{ortho}$), 7.56 (dd, J=9.7, 1.1 Hz, 1H, Ar—H$_{ortho}$), 7.67 (s, 2H, H$_{pyrrole}$), 7.83 (d, J=1.4 Hz, 1H, Ar—H$_{ortho}$).

$^{13}$C NMR (126 MHz, THF-d$_6$): δ (ppm)=14.3 (Me), 21.1 (CH$_2$), 30.7 (CH$_2$), 54.97 (CH$_2$), 118.4 (Ar—C$_{meta}$), 121.1 (C$_{pyrrole}$), 121.5*, 126.2 (C$_{pyrrole}$), 127.5 (Ar—C$_{ortho}$), 136.1 (Ar—C$_{ortho}$), 142.6*, 144.5 (Ar—C$_{para}$), 145.5 (C$_{pyrrole}$), 146.4 (C$_{meso}$). *These signals could not be assigned exactly to corresponding carbon atoms. They belong to the Ar—C$_{ipso}$ and the Ar—C$_{nitro}$ of the aryl residue.

HRMS (ESI-TOF): m/z calcd. for C$_{21}$H$_{29}$N$_4$O$_2^+$ [M+H]$^+$: 393.2285, found: 393.2315.

Chlorido{5-[4-(N,N-dibutylamino)-3-nitrophenyl]dipyrrinato}(pentamethyl-cyclopentadienyl)iridium(III) was prepared according to the general synthetic procedure. 5-[4-(N,N-Dibutylamino)-3-nitrophenyl]dipyrrinato (200 mg, 0.51 mmol), di(s-chlorido)bis[chlorido($\eta^5$-pentamethylcyclopendienyl)iridium(III)] (237 mg, 0.30 mmol), and N,N-diisopropylethylamine (1.42 mL, 8.32 mmol) were dissolved in 10 mL of THF. The crude product was purified by column chromatography (silica gel, DCM/EtOAc=9/1, v/v) and recrystallization (DCM/n-hexane) to obtain the product as a red solid (112 mg, 0.15 mmol, 29%).

Mp: 198-200° C.

$^1$H NMR (500 MHz, CDCl$_3$): δ (ppm)=0.91 (t, J=7.4 Hz, 6H, Me$_{butyl}$), 1.28-1.36 (m, 4H, CL), 1.49 (s, 15H, Me$_{Cp*}$), 1.51-1.62 (m, 4H, CH$_2$), 3.17-3.20 (m, 4H, CH$_2$), 6.47 (dd, J=4.4, 1.5 Hz, 2H, H$_{pyrrole}$), 6.59 (dd, J=4.4, 1.3 Hz, 2H, $H_{pyrrole}$), 7.12 (d, J=8.6 Hz, 1H, Ar—$H_{meta}$), 7.45 (dd, J=8.6, 2.2 Hz, 11H, Ar—$H_{ortho}$), 7.67 (t, J=1.4 Hz, 2H, $H_{pyrrole}$), 7.67 (t, J=1.4 Hz, 1H, Ar—$H_{ortho}$).

$^{13}$C NMR (126 MHz, CDCl$_3$): δ (ppm)=8.6 (Me$_{Cp*}$), 13.96 (Me$_{butyl}$), 20.3 (CH$_2$), 29.7 (CH$_2$), 52.1 (CH$_2$), 86.8 (C$_{Cp*}$), 118.4 (C$_{pyrrole}$), 120.3 (Ar—C$_{meta}$), 128.0 (Ar—C$_{ortho}$), 128.3*, 131.6 (C$_{pyrrole}$), 133.3 (C$_{pyrrole}$), 134.96 (Ar—C$_{ortho}$), 140.7*, 144.7 (C$_{meso}$), 145.4 (Ar—C$_{para}$), 153.8 (C$_{pyrrole}$). *These signals could not be assigned exactly to corresponding carbon atoms. They belong to the Ar—C$_{ipso}$ and the Ar—C$_{nitro}$ of the aryl residue.

HRMS (ESI-TOF): m/z calcd. for C$_{33}$H$_{42}$IrN$_4$O$_2$$^+$ [M−Cl]$^+$: 719.2932, found: 719.2976.

UV/Vis (DCM): $λ_{max}$ (nm) [log (ε/mol$^{-1}$ cm$^{-1}$)]=446 [4.29], 500 [4.20].

1.7 Chlorido(5-pentafluorophenyl-1,3,7,9-tetramethyldipyrrinato)(pentamethyl-cyclopentadienyl)iridium (III)

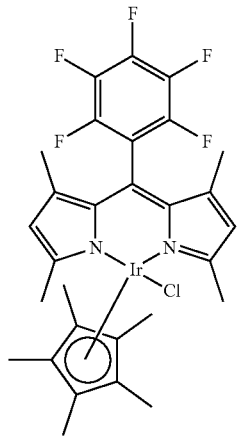

Chlorido(5-pentafluorophenyl-1,3,7,9-tetramethyldipyrrinato)(pentamethyl-cyclopentadienyl)iridium(III) was prepared according to the general synthetic procedure. 5-Pentafluorophenyl-1,3,7,9-tetramethyldipyrrin (prepared according to the literature [16]) (250 mg, 0.68 mmol), di(μ-chlorido)bis[chlorido(η$^5$-pentamethylcyclopendienyl)-iridium(III)] (272 mg, 0.341 mmol), and N,N-diisopropylethylamine (1.62 mL, 9.55 mmol) were dissolved in 10 mL of THF. The crude product was purified by column chromatography (silica gel, EtOAc/n-hexane=1/1, v/v) to obtain the product as an orange-green solid (161 mg, 0.221 mmol, 32%).

Mp: >250° C.

$^1$H NMR (500 MHz, CD$_2$Cl$_2$): δ (ppm)=1.40 (s, 15H, Me$_{Cp*}$), 1.68 (s, 6H, Me), 2.62 (s, 6H, Me), 6.16 (s, 2H, $H_{pyrrole}$).

$^{13}$C NMR (126 MHz, CD$_2$Cl$_2$): δ (ppm)=8.6 (Me$_{Cp*}$), 15.1 (Me), 18.9 (Me), 86.8 (C$_{Cp*}$), 123.4 (C$_{pyrrole}$), 130.6 (C$_{meso}$), 142.1 (C$_{pyrrole}$), 162.9 (C$_{pyrrole}$).

$^{19}$F NMR (376 MHz, CD$_2$Cl$_2$): δ (ppm)=−162.07−−161.89 ((m, 2F, CF$_{ortho}$), −153.99 (t, J=20.9 Hz, 1F, CF$_{para}$), −139.87 (dd, J=24.3, 8.5 Hz, 1F, CF$_{meta}$), −140.38 (dd, J=51.5, 22.8 Hz, 1F, CF$_{meta}$).

HRMS (ESI-TOF): m/z calcd. for C$_{29}$H$_{29}$F$_5$IrN$_2$$^+$ [M−Cl]$^+$: 693.1875, found: 693.1857, m/z calcd. for C$_{58}$H$_{58}$ClF$_{10}$Ir$_2$N$_4$$^+$ [2M−Cl]$^+$: 1421.3443, found: 1421.3393.

UV/Vis (DCM): $λ_{max}$ (nm) [log (ε/L mol$^{-1}$ cm$^{-1}$)]=518 [4.62].

Example 2

Preparation of Bis(Phenylpyridyl)Dipyrrinato-Iridium(III) Complexes Via the Reaction of Substituted Dipyrromethenes (Dipyrrins) with Bis(Phenylpyridyl)Iridium Chloride Dimer General synthetic procedure for the bis(phenylpyridyl) dipyrrinato-iridium(III) complexes: The corresponding dipyrrin (1 equiv.) and N,N-diisopropylethylamine (14 equiv.) were dissolved in THF. Under an argon atmosphere bis(μ-chlorido)tetrakis(2-phenylpyridyl)diiridium(III)(0.5 equiv.) was added and the mixture was stirred for 24 h at reflux. After the indicated time, DCM was added to the solution and was washed with water several times. The organic layer was dried with Na$_2$SO$_4$, filtered, and evaporated to dryness. The crude product was purified by column chromatography and recrystallization.

2.1 {5-[4-(N-2-Hydroxyethylamino)-2,3,5,6-tetrafluorophenyl]dipyrrinato}bis(2-phenyl-pyridyl) iridium(III)

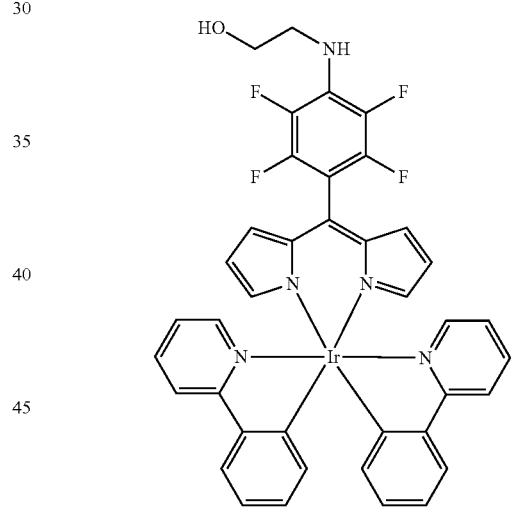

First, 5-[4-(N-2-hydroxyethylamino)-2,3,5,6-tetrafluorophenyl]dipyrrin was prepared according to the following synthetic procedure: 5-[4-(N-2-Hydroxyethylamino)-2,3,5, 6-tetrafluorophenyl]dipyrromethane (prepared according to the literature [12])(2.30 g, 6.51 mmol, 1 equiv.) and p-chloranil (1.60 g, 6.51 mmol, 1 equiv.) were dissolved in 30 mL of THF. The mixture was stirred for 24 h at room temperature. After evaporation, the solid was resolved in EtOAc and filtered over a silica filled glas frid (EtOAc). The filtrate was evaporated to dryness and the crude product was purified by column chromatography (silica gel, EtOAc) to obtain the product as a dark green solid (1.03 g, 2.94 mmol, 45%).

Mp: 129-136° C.

$^1$H NMR (500 MHz, (CD$_3$)$_2$CO): δ (ppm)=3.60-3.63 (m, 2H, CH$_2$), 3.81 (t, J=5.5 Hz, 2H, CH$_2$), 5.35 (br s, 11, NH), 6.43 (dd, J=4.2, 1.2 Hz, 2H, $H_{pyrrole}$), 6.71 (d, J=3.4 Hz, 2H, $H_{pyrrole}$), 7.74 (s, 2H, $H_{pyrrole}$).

$^{13}$C NMR (126 MHz, (CD$_3$)$_2$CO): δ (ppm)=48.4 (CH$_2$), 61.9 (CH$_2$), 119.2 (C$_{pyrrole}$), 120.9 (C$_{meso}$), 128.4 (C$_{pyrrole}$), 141.7 (C$_{pyrrole}$), 145.1 (C$_{pyrrole}$), 149.95 (Ar—CF$_{para}$).

$^{19}$F NMR (376 MHz, (CD$_3$)$_2$CO): δ (ppm)=−161.52 (d, J=16.7 Hz, 2F, CF$_{ortho}$), −144.67 (d, J=15.7 Hz, 2F, CF$_{meta}$).

HRMS (ESI-TOF): m/z calcd. for C$_{17}$H$_{14}$F$_4$N$_3$O$^+$ [M+H]$^+$: 352.1068, found: 352.1075.

{5-[4-(N-2-Hydroxyethylamino)-2,3,5,6-tetrafluorophenyl]dipyrrinato}bis(2-phenyl-pyridyl)iridium(III) was prepared according to the general synthetic procedure. 5-[4-(N-2-Hydroxyethylamino)-2,3,5,6-tetrafluorophenyl]dipyrrin (200 mg, 0.57 mmol), bis(μ-chlorido)tetrakis(2-phenylpyridyl)diiridium(III) (305 mg, 0.29 mmol) and N,N-diisopropylethylamine (1.36 mL, 7.97 mmol) were dissolved in 40 mL of THF. The crude product was purified by column chromatography (silica gel, DCM/EtOAc=9/1, v/v) and recrystallization (DCM+MeOH/n-pentane) to obtain the product as a red-brown solid (170 mg, 0.20 mmol, 35%).

Mp. >250° C.

$^1$H NMR (600 MHz, THF-d$_8$): δ (ppm)=3.51 (t, J=5.4 Hz, 2H, CH$_2$), 3.69 (t, J=5.5 Hz, 2H, CH$_2$), 6.16 (dd, J=4.3, 1.3 Hz, 2H, H$_{pyrrole}$), 6.35 (d, J=0.9 Hz, 2H, H$_{ppy}$), 6.53 (d, J=4.2 Hz, 2H, H$_{pyrrole}$), 6.70 (td, J=7.4, 1.3 Hz, 2H, H$_{ppy}$), 6.75 (t, J=1.3 Hz, 2H, H$_{pyrrole}$), 6.82 (td, 0.1=7.5, 1.2 Hz, 2H, H$_{ppy}$), 6.96 (ddd, J=7.3, 5.8, 1.4 Hz, 2H, H$_{ppy}$), 7.63-7.67 (m, 4H, H$_{ppy}$), 7.91-7.94 (m, 4H, H$_{ppy}$).

$^{13}$C NMR (151 MHz, THF-d$_6$): δ (ppm)=61.6 (CH$_2$), 67.7 (CH$_2$), 105.7 (d, J=6.7 Hz, Ar—Ar—C$_{ipso}$), 118.1 C$_{pyrrole}$), 119.3 (C$_{ppy}$), 121.2 (C$_{ppy}$), 122.6 (C$_{ppy}$), 124.5 (C$_{ppy}$), 126.9 (Ar—C$_{para}$), 129.8 (C$_{ppy}$), 130.4 (C$_{pyrrole}$), 132.8 (C$_{ppy}$), 133.4 (C$_{meso}$), 135.0 (C$_{pyrrole}$), 137.1 (C$_{ppy}$), 145.6 (C$_{ppy}$), 150.3 (C$_{ppy}$), 153.3 (C$_{pyrrole}$), 156.8 (C$_{ppy}$), 169.5 (C$_{ppy}$).

$^{19}$F NMR (376 MHz, THF-d$_8$) δ (ppm)=−162.40 (d, J=15.1 Hz, 2F, CF$_{ortho}$), −145.67-145.23 (m, 2F, CF$_{meta}$).

HRMS (ESI-TOF): m-z calcd. for C$_{39}$H$_{28}$F$_4$IrN$_5$ONa$^+$ [M+Na]$^+$: 874.1751, found: 874.1708, m/z calcd. for C$_{39}$H$_{28}$F$_4$IrN$_5$OK$^+$ [M+K]$^+$: 890.1491, found: 890.1458, m-z calcd. for C$_{78}$H$_{56}$F$_8$Ir$_2$N$_{10}$O$_2$K$^+$ [2M+K]$^+$: 1741.3350, found: 1741.3266.

UV/Vis (DCM): λ$_{max}$ (nm) [log (ε/L mol$^{-1}$ cm$^{-1}$)]=491 [4.59].

2.2 {5-[4-(N-2-Hydroxyethylamino)-3-nitrophenyl]dipyrrinato}bis(2-phenylpyridyl)-iridium(III)

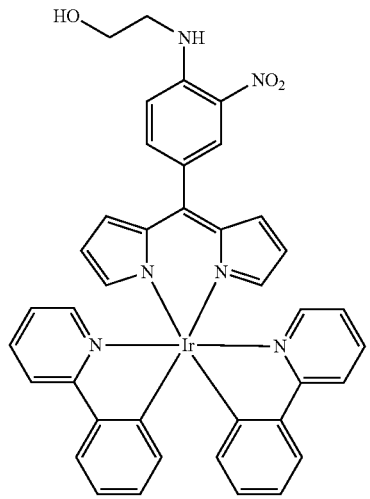

{5-[4-(N-2-Hydroxyethylamino)3-nitrophenyl]dipyrrinato}bis(2-phenylpyridyl)-iridium(III) to was prepared according to the general synthetic procedure. 5-[44N-2-Hydroxyethylamino)-3-nitrophenyl]dipyrrin (prepared according to the literature [7]) (200 mg, 0.62 mmol), bis(s-chlorido)tetrakis(2-phenylpyridyl)diiridium(III) (330 mg, 0.31 mmol), and N,N-diisopropylethylamine (1.47 mL, 8.63 mmol) were dissolved in 40 mL of THF. The crude product was purified by column chromatography (silica gel, DCM/n-hexane=3/1, v/v) and recrystallization (DCM/n-pentane) to obtain the product as an orange solid (223 mg, 0.27 mmol, 44%).

Mp: 241-250° C.

$^1$H NMR (500 MHz, CDCl$_3$): δ (ppm)=3.51 (t, J=5.4 Hz, 2H, CH$_2$), 3.91-3.51 (t, 1=5.4 Hz, 1H), 6.23-6.24 (m, 2H, H$_{pyrrole}$), 6.37 (dd, J=11.6, 7.5 Hz, 2H, H$_{ppy}$), 6.53 (d, J=7.2 Hz, 2H, H$_{pyrrole}$), 6.79-6.93 (m, 9H, Ar—H$_{meta}$, H$_{pyrrole}$, H$_{ppy}$), 7.52 (dd, J=8.7, 2.1 Hz, 1H, Ar—H$_{ortho}$), 7.56-7.61 (m, 4H, H$_{ppy}$), 7.76-7.80 (m, 4H, H$_{ppy}$), 8.26 (d, J=2.1 Hz, 1H, Ar—H$_{ortho}$).

$^{13}$C NMR (126 MHz, CDCl$_3$): δ (ppm)=45.1 (CH$_2$), 60.6 (CH$_2$), 112.5 (Ar—C$_{meta}$), 117.4 (C$_{pyrrole}$), 118.7 (C$_{ppy}$), 120.9 (C$_{ppy}$), 122.0 (d, J=35.7 Hz, C$_{ppy}$), 123.9 (C$_{ppy}$), 127.3*, 128.6 (Ar—C$_{ortho}$), 129.6 (d, J=13.7 Hz, C$_{ppy}$), 130.7 (d, J=16.2 Hz, C$_{pyrrole}$), 131.1*, 132.3 (d, J=18.2 Hz, C$_{ppy}$), 136.18 (d, J=19.0 Hz, C$_{ppy}$), 138.6 (Ar—C$_{ortho}$), 144.7 (d, J=16.4 Hz, C$_{ppy}$), 145.2 (C$_{meso}$), 145.9 (Ar—C$_{para}$), 149.6 (d, J=5.9 Hz, C$_{ppy}$), 152.8 (d, J=32.2 Hz, C$_{pyrrole}$), 156.5 (d, J=25.4 Hz, C$_{ppy}$), 168.8 (d, J=27.2 Hz, C$_{ppy}$). *These signals could not be assigned exactly to corresponding carbon atoms. They belong to the Ar—C$_{ipso}$ and the Ar—C$_{nitro}$ of the aryl residue.

HRMS (ESI-TOF): m/z calcd. for C$_{39}$H$_{37}$IrN$_6$O$_3$K$^+$ [M+K]$^+$: 863.1718, found: 863.1745.

UV/Vis (DCM): λ$_{max}$ (nm) [log (ε/L mol$^{-1}$ cm$^{-1}$)]=483 [4.51].

2.3 {5-[4-(N-1-Hydroxymethyl-2-hydroxyethylamino)-3-nitrophenyl]dipyrrinato}bis(2-phenylpyridyl)iridium(III)

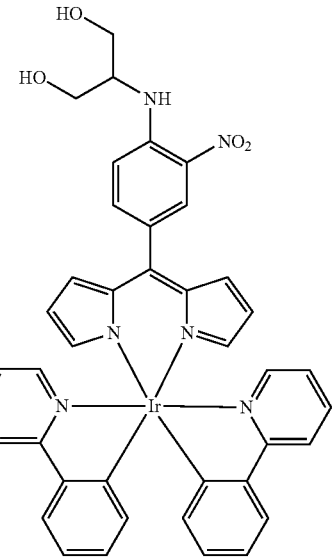

{5-[4-(N-1-Hydroxymethyl-2-hydroxyethylamino)-3-nitrophenyl]dipyrrinato}bis(2-phenylpyridyl)iridium(III) was prepared according to the general synthetic procedure 5-[4-(N-1-Hydroxymethyl-2-hydroxyethylamino)-3-nitrophenyl] dipyrrin (prepared according to the literature [7])(200 mg, 0.56 mmol), bis(μ-chlorido)tetrakis(2-phenylpyridyl) diiridium(III) (303 mg, 0.28 mmol), and N,N-diisopropylethylamine (1.34 mL, 7.90 mmol) were dissolved in 40 mL of THF. The crude product was purified by column chromatography (silica gel, DCM/MeOH=9/1, v/v) and recrystallization (DCM+MeOH/n-hexane) to obtain the product as a red solid (236 mg, 0.28 mmol, 49%).

Mp: 234-241° C.

$^1$H NMR (500 MHz, DMSO-d$_6$): δ (ppm)=3.60-3.64 (m, 2H, CHI), 3.66-3.70 (m, 2H, CH$_2$), 3.79-3.84 (m, 1H, CH), 5.06 (t, J=5.1 Hz, 2H, OH), 6.23 (dd, J=7.1, 3.4 Hz, 2H, H$_{ppy}$), 6.28 (d, J=4.3 Hz, 2H, H$_{pyrrole}$), 6.55 (d, J=4.2 Hz, 2H, H$_{pyrrole}$), 6.68 (s, 2H, H$_{pyrrole}$), 6.78 (t, J=7.3 Hz, 2H, H$_{ppy}$), 6.89 (td, J=7.6, 1.2 Hz, 2H, H$_{ppy}$), 7.15-7.20 (m, 2H, H$_{ppy}$), 7.23 (d, J=9.2 Hz, 1H, Ar—H$_{meta}$), 7.58 (dd, J=9.0, 2.1 Hz, 1H, Ar—H$_{ortho}$), 7.72 (d, J=5.6 Hz, 2H, H$_{ppy}$), 7.77-7.84 (m, 4H, H$_{ortho}$), 8.02 (d, J=2.2 Hz, 1H, Ar—H$_{ortho}$), 8.13 (d, J=8.2 Hz, 2H, H$_{ppy}$), 8.51 (d, J=8.1 Hz, 1H, NH).

$^{13}$C NMR (126 MHz, DMSO-d$_6$): δ (ppm)=55.4 (CH), 59.4 (CH$_2$), 114.2 (Ar—C$_{meta}$), 117.6 (C$_{pyrrole}$), 119.3 (C$_{ppy}$), 120.8 (C$_{ppy}$), 122.9 (C$_{ppy}$), 124.3 (C$_{ppy}$), 125.6*, 127.5 (Ar—C$_{ortho}$), 129.3*, 129.9 (C$_{ppy}$), 130.7 (C$_{pyrrole}$), 131.5 (C$_{ppy}$), 133.8 (C$_{pyrrole}$), 137.2 (C$_{ppy}$), 138.4 (Ar—C$_{ortho}$), 144.6 (C$_{ppy}$), 145.1 (C$_{meso}$), 146.2 (Ar—C$_{para}$), 148.8 (C$_{ppy}$), 151.6 (C$_{pyrrole}$), 155.9 (C$_{ppy}$), 167.9 (C$_{ppy}$).

*These signals could not be assigned exactly to corresponding carbon atoms. They belong to the Ar—C$_{ipso}$ and the Ar—C$_{nitro}$ of the aryl residue.

HRMS (ESI-TOF): m/z calcd. for C$_{40}$H$_{34}$IrN$_6$O$_4^+$ [M+H]$^+$: 855.2265, found: 855.2263, m/z calcd. for C$_{40}$H$_{33}$IrN$_6$O$_4$Na$^+$ [M+Na]$^+$: 877.2085, found: 877.2093, m/z calcd. for C$_{40}$H$_{33}$IrN$_6$O$_4$K$^+$ [M+K]$^+$: 893.1824, found: 893.1834.

UV/Vis (DCM): λ$_{max}$ (nm) [log (ε/L mol$^{-1}$ cm$^{-1}$)]=484 [4.46].

Example 3

Preparation of {[(pentafluorphenyl)-2,2-dipyrrylmethyl]bis(phenyl-2-pyridyl)}iridium(III) and {[(4-fluoro-3-nitrophenyl)-2,2-dipyrrylmethyl]-bis(phenyl-2-pyridyl)}iridium(III) and their subsequent modification via nucleophilic aromatic substitution 3.1 [5-(Pentafluorophenyl)dipyrrinato]bis(2-phenylpyridyl)iridium(III)

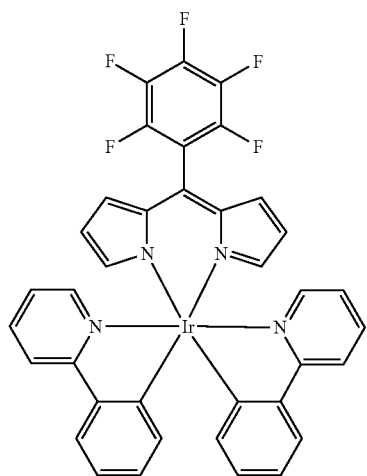

5-(Pentafluorophenyl)dipyrrin (prepared according to the literature [14])(200 mg, 0.65 mmol, 1 equiv.) and N,N-diisopropylethylamine (1.53 mL, 9.03 mmol, 14 equiv.) were dissolved in 40 mL of THF. Bis(μ-chlorido)tetrakis(2-phenylpyridyl)diiridium(III) (346 mg, 0.32 mmol 0.5 equiv.) was added and the mixture was stirred for 24 h at reflux. After the indicated time, DCM was added to the solution and was washed with water several times. The organic layer was dried with Na$_2$SO$_4$, filtered, and evaporated to dryness. The crude product was purified by column chromatography (silica gel, DCM/n-hexane=3/1, v/v) and recrystallization (DCM/h-pentane) to obtain the product as a red-brown solid (337 mg, 0.42 mmol, 65%).

Mp: >250° C.

$^1$H NMR (500 MHz, CDCl$_3$): δ (ppm)=6.27 (dd, J=4.3, 1.3 Hz, 2H, H$_{pyrrole}$), 6.39-6.41 (m, 2H H$_{ppy}$), 6.45 (d, J=4.3 Hz, 2H, H$_{pyrrole}$), 6.80 (t, J=1.2 Hz, 2H, H$_{pyrrole}$), 6.83 (td, J=7.4, 1.3 Hz, 2H, H$_{ppy}$), 6.90-6.94 (m, 4H, H$_{ppy}$), 7.59-7.62 (m, 4H, H$_{ppy}$), 7.81 (d, J=8.0 Hz, 2H, H$_{ppy}$), 7.90-7.92 (m, 2H, H$_{ppy}$).

$^{13}$C NMR (126 MHz, CDCl$_3$): δ (ppm)=118.5 (C$_{pyrrole}$), 118.8 (C$_{ppy}$), 121.1 (C$_{ppy}$), 122.1 (C$_{ppy}$), 124.0 (C$_{ppy}$), 129.5 (C$_{pyrrole}$), 129.8 (C$_{ppy}$), 130.5 (C$_{meso}$), 132.4 (C$_{ppy}$), 133.4 (C$_{pyrrole}$), 136.4 (C$_{ppy}$) 144.7 (C$_{ppy}$), 149.8 (C$_{ppy}$), 154.1 (C$_{pyrrole}$), 155.8 (C$_{ppy}$), 168.8 (C$_{ppy}$).

$^{19}$F NMR (376 MHz, CDCl$_3$): δ (ppm)=−161.67 (t, J=22.3 Hz, 2F, CF$_{ortho}$), −153.79 (t, J=21.2 Hz, 1F, CF$_{para}$, −139.85 (d, J=23.4 Hz, 2F, CF$_{meta}$).

HRMS (ESI-TOF): m/z calcd. for C$_{37}$H$_{22}$F$_5$IrN$_4$Na$^+$ [M+Na]$^+$: 833.1286, found: 833.1280, m/z calcd. for C$_{37}$H$_{22}$F$_5$IrN$_4$K$^+$ [M+K]$^+$: 849.1025, found: 849.1015.

UV/Vis (DCM): λ$_{max}$ (nm) [log (ε/L mol$^{-1}$ cm$^{-1}$)]=491 [4.56].

3.2 [5-(4-Fluoro-3-nitrophenyl)dipyrrinato]bis(2-phenylpyridyl)iridium(III)

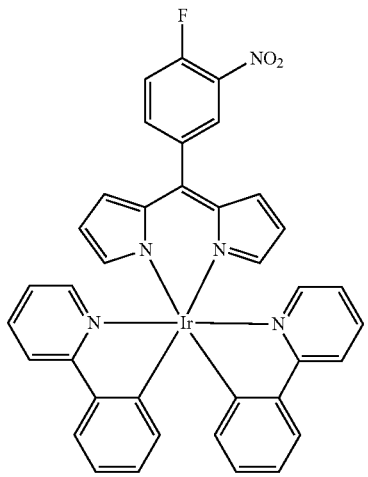

First, 5-(4-fluoro-3-nitrophenyl)dipyrrin was prepared according to the following synthetic procedure. 5-(4-Fluoro-3-nitrophenyl)dipyrromethane (prepared according to the literature [13]) (1.00 g, 3.51 mmol, 1 equiv.) and 2,3-dichloro-5,6-dicyano-1,4-benzoquinone (796 mg, 3.51 mmol, 1 equiv., 1 equiv.) were dissolved in 15 mL of THF. The mixture was stirred for 3 h at room temperature. Afterwards, the solvent was evaporated at reduced pressure, the remaining solid was resolved (EtOAc) and filtered over a silica gel filled glass flit (EtOAc/acetone=1/1, v/v). The filtrate was evaporated to dryness and the crude product was purified by column chromatography (silica gel, EtOAc, then EtOAc/acetone=1/1, v/v) to obtain the product as a dark brown solid (633 mg, 64%).

Mp: >250° C.

$^1$H NMR (500 MHz, THF-$d_6$): δ (ppm)=6.41 (dd, J=4.2, 1.4 Hz, 2H, $H_{pyrrole}$), 6.54 (dd, J=4.2, 1.1 Hz, 2H, $H_{pyrrole}$), 7.56 (dd, J=11.0, 8.5 Hz, 1H, Ar—$H_{meta}$), 7.71 (s, 2H, $H_{pyrrole}$), 7.84 (ddd, J=8.8, 4.4, 2.4 Hz, 1H, Ar—$H_{ortho}$), 8.23 (dd, J=7.2, 2.3 Hz, 1H, Ar—$H_{ortho}$).

$^{13}$C NMR (126 MHz, THF-$d_8$): δ (ppm)=102.5 (Ar—$C_{meta}$), 114.2, 119.1 ($C_{pyrrole}$), 129.5 (Ar—$C_{ortho}$), 130.3 ($C_{pyrrole}$), 136.8, 145.8 ($C_{pyrrole}$), 152.89 (d, J=167.3 Hz, Ar—$C_{para}$).

$^{19}$F NMR (376 MHz, THF-$d_8$): δ (ppm)=−119.35 (s, 1F, CF).

HRMS (ESI-TOF): m/z calcd. for $C_{15}H_{11}FN_3O_2^+$ [M+H]$^+$: 284.0830, found: 284.0858.

5-(4-Fluoro-3-nitrophenyl)dipyrrin (455 mg, 1.61 mmol, 1 equiv.) and N,N-diisopropylethylamine (3.82 mL, 22.49 mmol, 14 equiv.) were dissolved in 50 mL of THF. Bis(μ-chlorido)tetrakis(2-phenylpyridyl)diiridium(III) (861 mg, 0.80 mmol, 0.5 equiv.) was added and the mixture was stirred for 24 h at reflux. After the indicated time, DCM was added to the solution and was washed with water several times. The organic layer was dried with $Na_2SO_4$, filtered, and evaporated to dryness. The crude product was purified by column chromatography (silica gel, DCM/n-hexane=4/1, v/v) and recrystallization (DCM/n-hexane) to obtain as a reddish-green solid (366 mg, 0.47 mmol, 29%).

Mp: >250° C.

$^1$H NMR (500 MHz, CDCl$_3$): δ (ppm)=6.27 (d, J=4.9 Hz, 2H, $H_{pyrrole}$), 6.36-6.41 (m, 4H, $H_{pyrrole}$+$H_{ppy}$), 6.82-6.85 (m, 4H, $H_{pyrrole}$+$H_{ppy}$), 6.89-6.97 (m, 4H, $H_{ppy}$), 7.33 (dd, J=10.4, 8.5 Hz, 1H, Ar—$H_{meta}$), 7.61-7.65 (m, 41H, $H_{ppy}$), 7.70 (ddd, J=8.4, 4.1, 2.2 Hz, 11H, Ar—$H_{ortho}$), 7.81-7.84 (m, 4H, $H_{ppy}$), 8.14 (dd, J=7.0, 2.1 Hz, 11H, Ar—$H_{ortho}$).

$^{13}$C NMR (126 MHz, CDCl$_3$): δ (ppm)=117.3 (d, J=20.7 Hz, Ar—$C_{meta}$), 118.2 (d, J=8.5 Hz, $C_{pyrrole}$), 118.9 ($C_{ppy}$), 121.1 ($C_{ppy}$), 122.1 (d, J=29.4 Hz, $C_{ppy}$), 124.1 ($C_{ppy}$), 127.8 (Ar—$C_{ortho}$), 129.8 (d, J=11.0 Hz, $C_{ppy}$), 130.8 (d, J=2.7 Hz, $C_{pyrrole}$), 132.3 (d, J=13.8 Hz, $C_{ppy}$), 133.8 (d, J J=4.9 Hz, $C_{pyrrole}$), 136.4 (d, J=16.0 Hz, $C_{ppy}$), 136.8*, 137.3 (d, J=8.3 Hz, Ar—$C_{ortho}$), 143.6 ($C_{meso}$), 144.6 (d, J=12.8 Hz, $C_{ppy}$), 149.5 ($C_{ppy}$), 153.7 (d, 1=9.4 Hz, $C_{pyrrole}$), 155.3 (d, J=266.5 Hz, CF), 155.97 (d, J=20.0 Hz, $C_{ppy}$), 168.9 (d, J=20.9 Hz, $C_{ppy}$). *This signal could not be assigned exactly to a corresponding carbon atom. It belongs to the Ar—$C_{ipso}$ or the Ar—$C_{nitro}$ of the aryl residue.

$^{19}$F NMR (376 MHz, CDCl$_3$): δ (ppm)=−118.08 (ddd, J=10.8, 6.5, 4.0 Hz, 1F, CF).

HRMS (ESI-TOF): m/z calcd. for $C_{37}H_{26}FIrN_5O_2^+$ [M+H]$^+$: 784.1694, found: 784.1695, m/z calcd. for $C_{37}H_{25}FIrN_5O_2Na^+$ [M+Na]$^+$: 806.1514, found: 806.1521, m/z calcd. for $C_{37}H_{25}FIrN_5O_2K^+$ [M+K]$^+$: 822.1253, found: 806.1270.

UV/Vis (DCM): $\lambda_{max}$ (nm) [log (ε/L mol$^{-1}$ cm$^{-1}$)]=485 [4.58].

General synthetic procedure for the substitution with thio-carbohydrates: The bis(phenylpyridyl)dipyrrinato-iridium(III) complex (1 equiv.) and the corresponding thio-carbohydrate sodium salt (1.2 equiv.) were dissolved DMF. The mixture was stirred for the indicated time at room temperature. Afterwards, 5 ml of water was added and then evaporated to dryness. The crude product was purified by column chromatography and recrystallization.

3.3 Bis(2-phenylpyridyl){5-[2,3,5,6-tetrafluoro-4-(1'-thio-β-D-glucosyl)phenyl]-dipyrrinato}iridium (III)

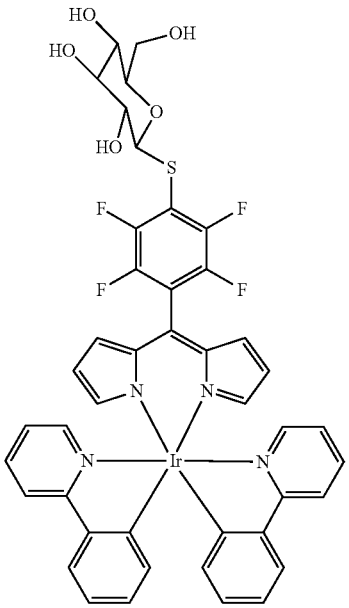

Bis(2-phenylpyridyl){5-[2,3,5,6-tetrafluoro-4-(1'-thio-β-D-glucosyl)phenyl]dipyrrinato}-iridium(III) was prepared according to the general synthetic procedure. (5-Pentafluorophenyldipyrrinato)bis(2-phenylpyridyl)iridium(III)(90 mg, 0.11 mmol) and 1'-thio-β-D-glucose sodium salt (29 mg, 0.13 mmol) were dissolved in 5 mL of DMF. The mixture was stirred for 20 min at room temperature. The crude product was purified by column chromatography (silica gel, DCM/MeOH=9/1) and recrystallization (DCM+MeOH/n-hexane) to obtain the product as a reddish-green solid (107 mg, 0.10 mmol, 98%).

Mp: 204-210° C.

$^1$H NMR (500 MHz, DMSO-$d_6$): δ (ppm)=3.07-3.23 (m, 4H, 2'-H, 3'-H, 4'-H, 5'-H), 3.33 (dd, J=12.3, 5.5 Hz, 1H, 6'-H+$H_2$O), 3.59 (dd, J=9.3, 2.3 Hz, 1H, 6'-H), 4.38 (dt, J=9.1, 5.6 Hz, 1H, OH), 4.83 (t, J=8.6 Hz, 1H, 1'-H), 5.03 (t, J=4.9 Hz, 1H, OH), 5.21 (d, J=4.8 Hz, 1H. OH), 5.61 (d, J=6.0 Hz, 1H, OH), 6.24 (d, J=7.5 Hz, 2H, $H_{ppy}$), 6.30 (d, J=4.3 Hz, 2H, $H_{pyrrole}$), 6.61 (d, J=4.0 Hz, 2H, $H_{pyrrole}$), 6.66 (s, 2H, $H_{pyrrole}$), 6.79 (t, J=7.6 Hz, 2H, $H_{ppy}$), 6.90 (t, J=7.5 Hz, 2H, $H_{ppy}$), 7.18 (t, J=6.7 Hz, 2H, $H_{ppy}$), 7.75-7.85 (m, 6H, $H_{ppy}$), 8.15 (d, J=8.3 Hz, 2H, $H_{ppy}$).

$^{13}$C NMR (126 MHz, DMSO-$d_6$): δ (ppm)=61.1 (6'-C), 70.1 (2'-C), 74.6 (4'-C), 78.0 (3'-C), 81.6 (5'-C), 84.6 (1'-C, 118.6 ($C_{pyrrole}$), 119.4 ($C_{ppy}$), 120.98 ($C_{ppy}$), 122.8 ($C_{ppy}$), 124.3 ($C_{ppy}$) 129.3 ($C_{ppy}$), 130.2 ($C_{pyrrole}$), 131.3 ($C_{meso}$), 131.5 ($C_{ppy}$), 132.7 ($C_{pyrrole}$), 137.4 ($C_{ppy}$), 144.6 ($C_{ppy}$), 148.8 ($C_{ppy}$), 152.9 ($C_{pyrrole}$), 155.2 ($C_{ppy}$), 167.8 ($C_{ppy}$).

$^{19}$F NMR (376 MHz, DMSO-$d_6$): δ (ppm)=−142.11 (dd, J=26.4, 10.6 Hz, 2F, $CF_{ortho}$), −133.24 (ddd, J=78.5, 26.5, 10.9 Hz, 2F, $CF_{meta}$).

HRMS (ESI-TOF): m/z calcd. for $C_{43}H_{33}F_4IrN_4O_3S^+$ [M]$^+$: 986.1732, found: 986.1755, m/z calcd. for $C_{43}H_{33}F_4IrN_4OSSNa^+$ [M+Na]$^+$: 1009.1629, found. 1009.1641, m/z calcd. for $C_{43}H_{33}F_4IrN_4O_5SNa^+$ [M+K]$^+$: 1025.1369, found: 1025.1392, m/z calcd. for $C_{86}H_{66}F_8Ir_2N_8O_{10}S_2Na^+$ [2M+Na]$^+$: 1995.3366, found: 1995.3373.

UV/Vis (MeOH): $\lambda_{max}$ (nm) [log ($\epsilon$/L mol$^{-1}$ cm$^{-1}$)]=487 [4.44].

3.4 Bis(2-phenylpyridyl){5-[2,3,5,6-tetrafluoro-4-(1'-thio-β-D-galactosyl)phenyl]-dipyrrinato}iridium (III)

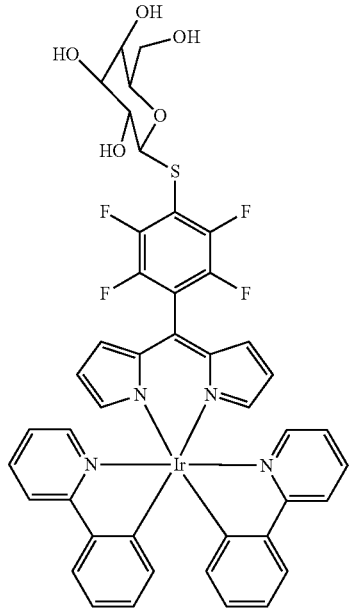

Bis(2-phenylpyridyl){5-[2,3,5,6-tetrafluoro-4-(1'-thio-β-D-galactosyl)phenyl]-dipyrrinato}iridium(III) was prepared according to the general synthetic procedure. (5-Pentafluorophenyldipyrrinato)bis(2-phenylpyridyl)iridium(III) (90 mg, 0.11 mmol) and 1'-thio-β-D-galactose sodium salt (29 mg, 0.13 mmol) were dissolved in 5 mL of DMF. The mixture was stirred for 20 min at room temperature. The crude product was purified by column chromatography (silica gel, DCM/MeOH=9/1) and recrystallization (DCM+MeOH/n-hexane) to obtain the product as a reddish-green solid (101 mg, 0.10 mmol, 92%).

Mp: 200-209° C.

$^1$H NMR (500 MHz, DMSO-d$_6$): δ (ppm)=3.43-3.53 (m, 5H, 3'-H, 4'-H, 5'-H, 6'-H+H$_2$O), 3.67-3.69 (m, 1H, 2'-H), 4.48 (dt, J=11.1, 5.4 Hz, 1H, OH), 4.55 (d, J=4.3 Hz, 1H, OH), 4.76-4.80 (m, 1H, 11H), 4.95 (d, 1=5.8 Hz, 1H, OH), 5.40 (d, J=6.3 Hz, 1H, OH), 6.24 (d, J=7.2 Hz, 2H, H$_{ppy}$), 6.30 (d, J=4.5 Hz, 2H, H$_{pyrrole}$), 6.59 (d, J=4.2 Hz, 2H, H$_{pyrrole}$), 6.67 (s, 2H, H$_{pyrrole}$), 6.79 (t, J=7.7 Hz, 2H, H$_{ppy}$), 6.90 (t, J=7.9 Hz, 2H, H$_{ppy}$), 7.18 (t, J=7.1 Hz, 2H, H$_{ppy}$), 7.78-7.85 (m, 6H, H$_{ppy}$), 8.15 (d, J=8.2 Hz, 2H, H$_{ppy}$).

$^{13}$C NMR (126 MHz, DMSO-d$_6$): δ (ppm)=60.3 (6'-C), 68.3 (2'-C), 71.3 (4'-C), 74.5 (3'-C), 79.7 (5'-C), 85.4 (1'-C), 118.6 (C$_{pyrrole}$), 119.4 (C$_{ppy}$), 120.99 (C$_{ppy}$), 122.8 (C$_{ppy}$), 124.3 (C$_{ppy}$), 129.3 (C$_{ppy}$), 130.1 (C$_{pyrrole}$), 131.2 (C$_{meso}$), 131.5 (C$_{ppy}$), 132.7 (C$_{pyrrole}$), 137.4 (C$_{ppy}$), 144.6 (C$_{ppy}$), 148.8 (C$_{ppy}$), 152.9 (C$_{meso}$), 155.2 (C$_{ppy}$), 167.8 (C$_{ppy}$).

$^{19}$F NMR (376 MHz, DMSO-d$_6$): δ (ppm)=−142.25-−142.211 (m, 2F, CF$_{ortho}$), −132.99 (ddd, J=51.1, 26.5, 10.8 Hz, 2F, CF$_{meta}$).

HRMS (ESI-TOF): m/z calcd. for C$_{43}$H$_{34}$F$_4$IrN$_4$O$_5$S$^+$ [M+H]$^+$: 987.1810, found: 987.1787, m/z calcd. for C$_{43}$H$_{33}$F$_4$IrN$_4$O$_5$SNa$^+$ [M+Na]$^+$: 1009.1629, found: 1009.1616, m/z calcd. for C$_{43}$H$_{33}$F$_4$IrN$_4$O$_5$SNa$^+$ [M+K]$^+$: 1025.1369, found: 1025.1356.

UV/Vis (MeOH): $\lambda_{max}$ (nm) [log ($\epsilon$/L mol$^{-1}$ cm$^{-1}$)]=487 [4.59].

3.5 {5-[3-Nitro-4-(1'-thio-β-D-glucosyl)phenyl]dipyrrinato}bis(2-phenylpyridyl)-iridium(III)

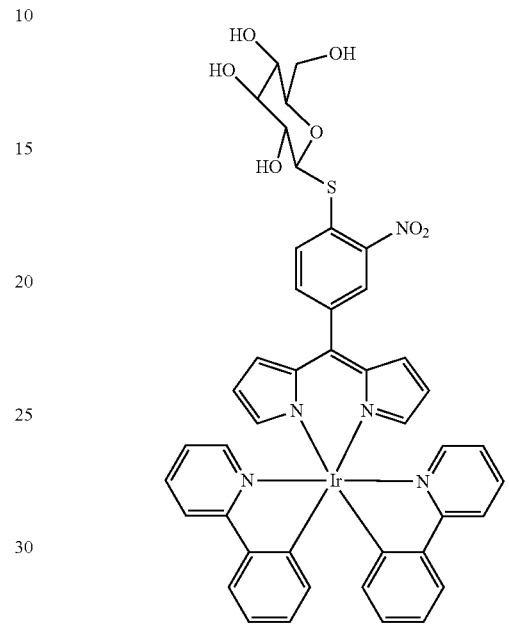

{5-[3-Nitro-4-(1'-thio-β-D-glucosyl)phenyl]dipyrrinato}bis(2-phenylpyridyl)iridium(III) was prepared according to the general synthetic procedure. [5-(4-Fluoro-3-nitrophenyl)-dipyrrinato]bis(2-phenylpyridyl)iridium(III) (90 mg, 0.12 mmol) and 1'-thio-β-D-glucose sodium salt (30 mg, 0.14 mmol) were dissolved in 5 mL of DMF. The mixture was stirred for 20 min at room temperature. The crude product was purified by column chromatography (silica gel, DCM/MeOH=9/1, v/v) and recrystallization (DCM+MeOH/n-hexane to obtain the product as a red solid (99 mg, 0.10 mmol, 90%).

Mp: >250° C.

$^1$H NMR (500 MHz, DMSO-d$_6$): δ (ppm)=3.17-3.22 (m, 1H, 2'-H), 3.25-3.31 (m, 2H, 3'-H, 4'-H), 3.38-3.49 (m, 2H, 5'-H, 6'-H), 3.70-3.74 (m, 1H, 6'-H), 4.57-4.62 (m, 1H, OH), 4.92 (t, J=9.7 Hz, 1H, 1'-H), 5.10 (d, J=5.3 Hz, H, OH), 5.23 (d, J=4.7 Hz, 1H, OH), 5.61 (d, J=3.9 Hz, 1H, OH), 6.23-6.25 (m, 2H, H$_{ppy}$), 6.29 (d, J=5.5 Hz, 2H, H$_{pyrrole}$), 6.44 (t, J=4.7 Hz, 2H, H$_{pyrrole}$), 6.69 (d, J=13.4 Hz, 2H, H$_{pyrrole}$), 6.79 (t, J=7.3 Hz, 2H, H$_{ppy}$), 6.90 (t, J=7.4 Hz, 2H, H$_{ppy}$), 7.18-7.22 ((m, 2H, H$_{ppy}$), 7.69 (dd, J=8.3, 1.8 Hz, 1H, Ar—H$_{ortho}$), 7.75-7.85 (m, 6H, H$_{ppy}$), 7.94 (t, J=8.6 Hz, 1H, Ar—H$_{ortho}$), 8.13-8.16 (m, 3H, H$_{ppy}$, Ar—H$_{meta}$).

$^{13}$C NMR (126 MHz, DMSO-d$_6$): δ (ppm)=60.9 (6'-C), 69.7 (2'-C), 72.3 (4'-C), 78.3 (3'-C), 81.1 (5'-C), 84.6 (1'-C), 117.8 (C$_{pyrrole}$), 119.3 (C$_{ppy}$), 120.8 (C$_{ppy}$), 122.9 (d, J=11.4 Hz, C$_{ppy}$), 124.2 (C$_{ppy}$), 126.3 (d, J=11.0 Hz, Ar—C$_{ortho}$), 127.7 (d, J=16.6 Hz, Ar—C$_{meta}$), 129.3 (C$_{ppy}$), 130.9 (C$_{pyrrole}$), 131.5 (C$_{ppy}$), 133.2 (C$_{pyrrole}$), 135.3 (Ar—C$_{para}$), 135.7 (Ar—C$_{ortho}$), 135.97 (d, J=6.1 Hz, C$_{ppy}$), 137.2*, 144.3*, 144.6 (C$_{meso}$), 144.96 (d, J=14.2 Hz, C$_{ppy}$), 148.9 (d, J=10.7 Hz, C$_{ppy}$), 152.1 (C$_{pyrrole}$), 155.6 (C$_{ppy}$), 167.74 (d, J=5.1 Hz, C$_{ppy}$). *These signals could not be assigned exactly to corresponding carbon atoms. They belong to the Ar—$C_{ipso}$ and the Ar—$C_{nitro}$ of the aryl residue.

HRMS (ESI-TOF): m/z calcd. for $C_{43}H_{36}IrN_5O_7SNa^+$ [M+Na]$^+$: 982.1857, found: 982.1888, m/z calcd. for $C_{43}H_{36}IrN_5O_7SK^+$ [M+K]$^+$: 998.1596, found: 998.1627.

UV/Vis (MeOH): J=(nm) [log (ε/L mol$^1$ cm$^{-1}$)]=482 [4.49].

3.6 {5-[3-Nitro-4-(1'-thio-β-D-galactosyl)phenyl]dipyrrinato}bis(2-phenylpyridyl)-iridium(III)

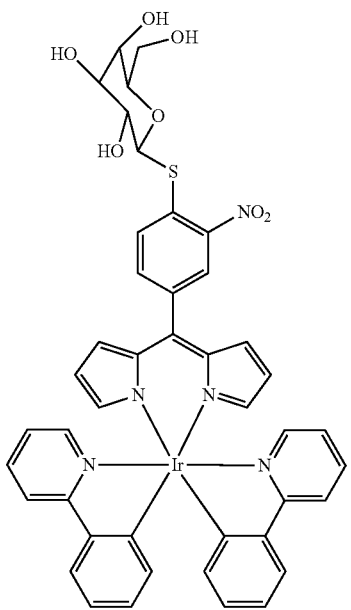

{5-[3-Nitro-4-(1'-thio-β-D-galactosyl)phenyl]dipyrrinato}bis(2-phenylpyridyl)-iridium(III) was prepared according to the general synthetic procedure. [5-(4-Fluoro-3-nitrophenyl)-dipyrrinato]bis(2-phenylpyridyl)iridium(III) (90 mg, 0.12 mmol) and 1'-thio-β-D-galactose sodium salt (30 mg, 0.14 mmol) were dissolved in 5 mL of DMF. The mixture was stirred for 20 min at room temperature. The crude product was purified by column chromatography (silica gel, DCM/MeOH=9/1, v/v) and recrystallization (DCM+MeOH/n-hexane) to obtain the product as a red solid (101 mg, 0.10 mmol, 92%).

Mp: >250° C.

$^1$H NMR (500 MHz, DMSO-d$_6$), δ (ppm)=3.42-3.45 (m, 1H, 3'-H), 3.51-3.54 (m, 2H, 6'-H), 3.60-3.67 (m, 2H, 4'-H, 5'-H), 3.76-3.78 (m, 1H, 2'-H), 4.61 (d, J=4.5 Hz, 1H, OH), 4.67-4.71 (m, 1H, OH), 4.86 (t, J=9.4 Hz, 1H, 1'-H), 5.03 (d, J=5.8 Hz, H, OH), 5.45 (dd, J=6.1, 1.0 Hz, 1H, OH), 6.22-6.25 (m, 2H, H$_{ppy}$), 6.29 (dd, J=4.3, 0.9 Hz, 2H, H$_{pyrrole}$), 6.42-6.46 (m, 2H, H$_{pyrrole}$), 6.69 (d, J=13.1 Hz, 2H, H$_{pyrrole}$), 6.79 (td, J=7.3, 1.7 Hz, 2H, H$_{ppy}$), 6.89 (t, J=7.5 Hz, 2H, H$_{ppy}$), 7.17-7.22 (m, 2H, H$_{ppy}$), 7.68 (dt, J=8.4, 2.2 Hz, 1H, Ar—H$_{ortho}$), 7.80-7.85 (m, 6H, H$_{ppy}$), 7.98 (t, J=8.8 Hz, 1H, Ar—H$_{ortho}$), 8.13-8.16 (m, 3H, H$_{ppy}$, Ar—H$_{meta}$).

$^{13}$C NMR (126 MHz, DMSO-d$_6$): δ (ppm)=60.6 (6'-C), 68.4 (2'-C), 68.95 (4'-C), 74.7 (3'-C), 79.4 (5'-C), 85.5 (1'-C), 117.9 (C$_{pyrrole}$), 119.3 (C$_{ppy}$), 120.8 (C$_{ppy}$), 122.9 (d, J=15.5 Hz, C$_{ppy}$), 124.2 (C$_{ppy}$), 126.3 (Ar—C$_{ortho}$), 127.7 (d, J=11.0 Hz, Ar—C$_{meta}$), 129.3 (C$_{ppy}$), 130.9 (d, J=7.7 Hz, C$_{pyrrole}$), 131.5 (C$_{ppy}$), 133.3 (C$_{pyrrole}$), 135.0 (Ar—C$_{para}$), 135.3 (Ar—C$_{ortho}$), 135.9 (d, J=6.2 Hz, C$_{ppy}$), 137.2*, 144.5*, 144.6 (C$_{meso}$), 144.7 (C$_{ppy}$), 148.9 (C$_{ppy}$), 152.0 (d, J=6.9 Hz, C$_{pyrrole}$), 155.6 (C$_{ppy}$), 167.74 (d, J=6.2 Hz, C$_{ppy}$).

*These signals could not be assigned exactly to corresponding carbon atoms. They belong to the Ar—$C_{ipso}$ and the Ar—$C_{nitro}$ of the aryl residue.

HRMS (ESI-TOF): m/z calcd. for $C_{43}H_{37}IrN_5O_7S^+$ [M+H]$^+$: 960.2037, found: 960.2081, m/z calcd. for $C_{43}H_{36}IrN_5O_7SNa^+$ [M+Na]$^+$: 982.1857, found: 982.1927, m/z calcd. for $C_{43}H_{36}IrN_5O_7SK^+$ [M+K]$^+$: 998.1596, found: 998.1668, m/z calcd. for $C_{86}H_{72}Ir_2N_{10}O_{14}S_2Na^+$ [2M+Na]$^+$: 1941.3822, found: 1941.3948.

UV/Vis (MeOH): $\lambda_{max}$ (nm) [log (ε/L mol$^{-1}$ cm$^{-1}$)]=481 [4.59].

3.7 Bis(2-Phenylpyridyl){5-[4-(N-prop-2-ynylamino)-2,3,5,6-tetrafluorophenyl]-dipyrrinato}iridium(III)

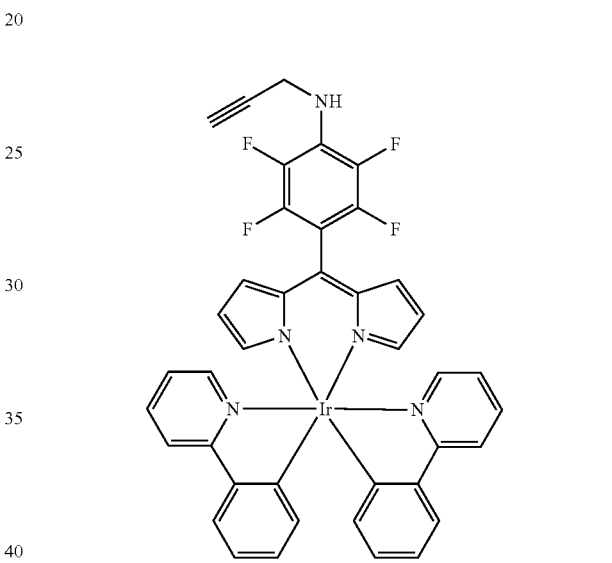

(5-Pentafluorophenyldipyrrinato)bis(2-phenylpyridyl) iridium(III) (100 mg, 0.12 mmol, 1 equiv.) and propargylamine (0.16 mL, 2.47 mmol, 10 equiv.) were dissolved in 1 ml of DMSO. The mixture was stirred for 24 h at 80° C. After the indicated time, the mixture was diluted with EtOAc and was washed with water several times. The organic layer was dried with Na$_2$SO$_4$, filtered, and evaporated to dryness. The crude product was purified by column chromatography (silica gel, DCM/n-hexane=1/1, v/v) and recrystallization (DCM+MeOH/n-hexane) to obtain the product as a red-brown solid (66 mg, 78 µmol, 64%).

Mp: >250° C.

$^1$H NMR (500 MHz, THF-d$_6$): δ (ppm)=2.68-2.69 (m, 1H, CH), 4.17 (d, J=6.2, 2H, CH$_2$), 5.84 (br s, 1H, NH), 6.17 (d, J=4.2 Hz, 2H, H$_{pyrrole}$), 6.36 (d, J=7.4 Hz, 2H, H$_{ppy}$), 6.52 (d, J=4.1 Hz, 2H, H$_{pyrrole}$), 6.71 (t, J=7.4 Hz, 2H, H$_{ppy}$), 6.76 (s, 2H, H$_{pyrrole}$), 6.84 (t, J=7.4 Hz, 2H, H$_{ppy}$), 6.97 (t, J=6.5 Hz, 2H, H$_{ppy}$), 7.63-7.57 (m, 4H, H$_{ppy}$), 7.93 (d, J=7.4 Hz, 4H, H$_{ppy}$).

$^{13}$C NMR (126 MHz, THF-d$_6$): δ (ppm)=35.7 (CH$_2$), 73.1 (CH), 81.8 (C), 108.1 (Ar—C$_{ipso}$), 118.6 (C$_{pyrrole}$), 119.7 (C$_{ppy}$), 121.6 (C$_{ppy}$), 122.99 (C$_{ppy}$, 124.8 (C$_{ppy}$), 130.2 (C$_{ppy}$), 130.8 (C$_{pyrrole}$), 133.2 (C$_{ppy}$), 133.5 (C$_{meso}$), 135.3 (C$_{pyrrole}$), 137.5 (C$_{ppy}$), 145.95 (C$_{ppy}$), 150.7 (C$_{ppy}$), 154.0 (C$_{pyrrole}$), 157.1 (C$_{ppy}$), 169.9 (C$_{ppy}$).

$^{19}$F NMR (376 MHz, THF-d$_8$): δ (ppm)=−160.84 (d, J=15.8 Hz, 2F, CF$_{ortho}$), −144.86 (dd, J=19.8, 5.4 Hz, 2F, CF$_{meta}$).

HRMS (ESI-TOF): m/z calcd. for C$_{40}$H$_{27}$F$_4$IrN$_5^+$ [M+H]$^+$: 846.1826, found: 846.1836, m/z calcd. for C$_{40}$H$_{26}$F$_4$IrN$_5$Na$^+$ [M+Na]$^+$: 868.1646, found: 868.1663, m/z calcd. for C$_{40}$H$_{26}$F$_4$IrN$_5$K$^+$ [M+K]$^+$: 884.1385, found: 884.1409, m/z calcd. for C$_{80}$H$_{52}$F$_8$Ir$_2$N$_{10}$K$^+$ [2M+K]$^+$: 1729.3139, found: 1729.3156.

UV/Vis (DCM): λ$_{max}$ (nm) [log (ε/L mol$^{-1}$ cm$^{-1}$)]=490 [4.46].

3.8 Bis(2-Phenylpyridyl){5-[4-(prop-2-ynyloxy)-2,3,5,6-tetrafluorophenyl]dipyrrinato}-iridium(III)

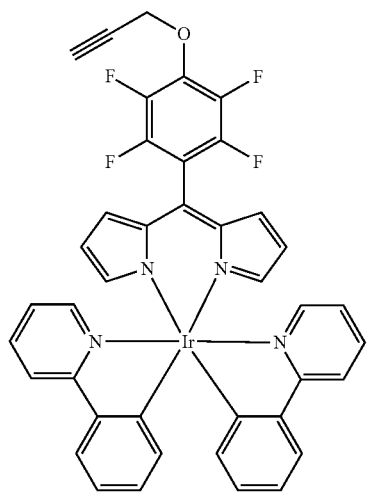

(5-Pentafluorophenyldipyrrinato)bis(2-phenylpyridyl) iridium(III) (70 mg, 86 μmol, 1 equiv.) was dissolved in 5 mL of THF. Freshly powdered potassium hydroxide (24 mg, 0.43 mmol, 5 equiv.) and propargyl alcohol (0.05 mL, 0.86 mmol, 10 equiv.) were added. The mixture was stirred for 24 h at room temperature. Afterwards, the mixture was diluted with DCM and washed several times with water. The organic layer was dried with Na$_2$SO$_4$, filtered, and evaporated to dryness. The crude product was purified by column chromatography (silica gel, DCM/n-hexane=1/1, v/v) to obtain the product as a black solid (63 mg, 75 μmol, 87%).

Mp: >250° C.

$^1$H NMR (500 MHz, THF-d$_8$): δ (ppm)=3.19 (t, J=2.4 Hz, 1H, CH), 5.01 (d, J=2.4 Hz, 2H, CH$_2$), 6.19 (dd, J=4.3, 1.2 Hz, 2H, H$_{pyrrole}$), 6.36 (d, J=7.4 Hz, 2H, H$_{ppy}$), 6.49 (d, J=4.2 Hz, 2H, H$_{pyrrole}$), 6.72 (td, J=7.4, 1.1 Hz, 2H, H$_{ppy}$), 6.78 (s, 2H, H$_{pyrrole}$), 6.84 (td, J=8.3, 7.7, 1.0 Hz, 2H, H$_{ppy}$), 6.94-6.99 (m, 2H, H$_{ppy}$), 7.64-7.69 (m, 4H, H$_{ppy}$), 7.92-7.95 (m, 4H, H$_{ppy}$).

$^{13}$C NMR (126 MHz, THF-d$_8$): δ (ppm)=62.9 (CH$_2$), 78.3 (C), 79.1 (CH), 118.9 (C$_{pyrrole}$), 119.8 (C$_{ppy}$), 121.7 (C$_{ppy}$), 123.0 (C$_{ppy}$), 124.9 (C$_{ppy}$), 130.2 (C$_{ppy}$), 130.6 (C$_{pyrrole}$), 132.0 (C$_{meso}$), 133.2 (C$_{ppy}$), 134.6 (C$_{pyrrole}$), 137.5 (C$_{ppy}$), 145.9 (C$_{ppy}$), 150.6 (C$_{ppy}$), 154.5 (C$_{pyrrole}$), 156.8 (C$_{ppy}$), 169.9 (C$_{ppy}$).

$^{19}$F NMR (376 MHz, THF-d$_8$): δ (ppm)=−155.75 (d, J=16.0 Hz, 2F, CF$_{ortho}$), −141.46 (d, J=16.0 Hz, 2F, CF$_{meta}$).

HRMS (ESI-TOF): m/z calcd. for C$_{40}$H$_{25}$F$_4$IrN$_4$ONa$^+$ [M+Na]$^+$: 869.1486, found: 869.1447, m/z calcd. for C$_{40}$H$_{25}$F$_4$IrN$_4$OK$^+$ [M+K]$^+$: 885.1225, found: 885.1193.

UV/Vis (DCM): λ$_{max}$ (nm) [log (ε/L mol$^{-1}$ cm$^{-1}$)]=491 [4.51].

3.9 {5-[3-Nitro-4-(N-prop-2-ynylamino)phenyl]dipyrrinato}bis(2-phenylpyridyl)-iridium(III)

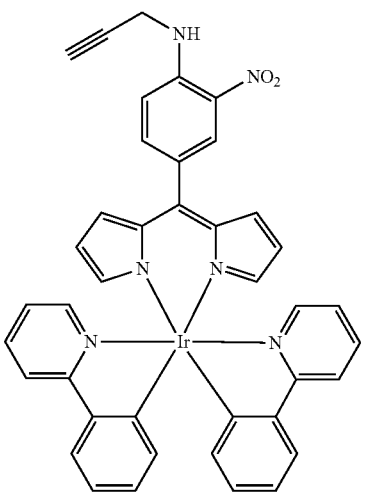

[5-(4-Fluoro-3-nitrophenyl)dipyrrinato]bis(2-phenylpyridyl)iridium(III) (90 mg, 0.12 mmol, 1 equiv.) and propargylamine (0.15 mL, 2.30 mmol, 20 equiv.) were dissolved in 5 mL of DCM. The mixture was stirred for 24 h at room temperature. After the indicated time, the mixture was diluted with EtOAc and was washed with water several times. The organic layer was dried with Na$_2$SO$_4$, filtered, and evaporated to dryness. The crude product was purified by column chromatography (silica gel, DCM/n-hexane=2/1, v/v) to obtain the product as a red solid (85 mg, 0.10 mmol, 90/).

Mp: >250° C.

$^1$H NMR (500 MHz, CD$_2$Cl$_2$): δ (ppm)=2.40 (t, J=2.5 Hz, 1H, CH), 4.22 (dd, J=5.8, 2.5 Hz, 2H, CH$_2$), 6.26 (dd, J=4.3, 1.3 Hz, 2H, H$_{pyrrole}$), 6.39 (t, J=6.7 Hz, 2H, H$_{ppy}$), 6.56 (d, J=4.3 Hz, 2H, H$_{pyrrole}$), 6.81 (s, 2H, H$_{pyrrole}$), 6.84 (t, J=7.3 Hz, 2H, H$_{ppy}$), 6.94-7.01 (m, 4H, H$_{ppy}$), 7.05 (d, J=8.8 Hz, 1H, Ar—H$_{meta}$), 7.63 (dd, J=8.7, 2.1 Hz, 1H, Ar—H$_{ortho}$), 7.64-7.70 (m, 4H, H$_{ppy}$), 7.85 (d, J=5.8 Hz, 2H, H$_{ppy}$), 7.88 (d, J=8.1 Hz, 2H, H$_{ppy}$), 8.21 (t, J=5.7 Hz, 1H, NH), 8.28 (d, J=2.1 Hz, 1H, Ar—H$_{ortho}$).

$^{13}$C NMR (126 MHz, CD$_2$Cl$_2$): δ (ppm)=33.2 (CH$_2$), 72.6 (CH), 79.4 (C), 113.2 (Ar—C$_{meta}$), 117.8 (d, J=4.7 Hz, C$_{pyrrole}$), 119.2 (C$_{ppy}$), 121.3 (C$_{ppy}$), 122.6 (d, J=20.7 Hz, C$_{ppy}$), 124.4 (C$_{ppy}$), 128.4 (Ar—C$_{ortho}$), 128.7*, 129.9 (d, J=9.3 Hz, *), 131.3 (d, J=7.3 Hz, C$_{pyrrole}$), 132.5 (d, J=9.0 Hz, C$_{ppy}$), 134.8 (d, J=10.2 Hz, C$_{pyrrole}$), 136.8 (d, J=9.9 Hz, C$_{ppy}$), 138.7 (Ar—C$_{ortho}$), 144.4 (C$_{meso}$), 145.1 (d, J=10.1 Hz, C$_{ppy}$), 146.3 (Ar—C$_{para}$), 149.98 (d, J=7.1 Hz, C$_{ppy}$), 152.98 (d, J=17.7 Hz, C$_{pyrrole}$), 156.8 (C$_{ppy}$), 169.0 (d, J=16.7 Hz, C$_{ppy}$). *These signals could not be assigned exactly to corresponding carbon atoms. They belong to the Ar—C$_{ipso}$ and the Ar—C$_{nitro}$ of the aryl residue.

HRMS (ESI-TOF): m/z calcd. for C$_{40}$H$_{29}$IrN$_6$O$_2$Na$^+$ [M+Na]$^+$: 841.1873, found: 841.1866, m/z calcd. for C$_{40}$H$_{29}$IrN$_6$O$_2$K$^+$ [M+K]$^+$: 857.1613, found: 857.1607.

UV/Vis (DCM): λ$_{max}$ (nm) [log (ε/L mol$^{-1}$ cm$^{-1}$)]=483 [4.61].

Example 4

Cell tests of selected compounds in the HT 29 and other cell lines

The photosensitizing activity was determined in the following cell lines:
- HT29 (human colon adenocarcinoma cell line)
- L929 (mouse fibroblast cell line)
- A431 (human epidermoid carcinoma cell line)
- A253 (submaxillary salivary gland, epidermoid cell line)
- CAL-27 (human tongue squamous cell carcinoma cell line)
- J774A.1 (Mouse BALB/c monocyte macrophage).

The cell lines were grown in DMEM (c.c.pro GmbH) supplemented with 10% heat-inactivated fetal calf serum (FCS, c.c.pro GmbH), 1% penicillin (10000 IU) and streptomycin (10000 μg/ml, c.c.pro GmbH). Cells were kept as a monolayer culture in a humidified incubator (5% $CO_2$ in air at 37° C.). A photosensitizer stock solution (2 mM) was performed in DMSO and was kept in the dark at 4° C. Further dilution was performed in DMEM medium without phenol red supplemented with 10% FCS to reach a final photosensitizer concentration of 2 or 10 μM, respectively. After seeding the cells in micro plates, the cells were incubated with fresh medium (DMEM without phenol red) containing 10% FCS with 2 or 10 μM of the photosensitizer for 24 h before light exposure. Before photosensitization, cells were washed, cell culture medium was exchanged with DMEM without phenol red and 10% FCS, then irradiated at room temperature with white light source at a fixed fluence rate of about 100 mW/cm² (50 J/cm²). Following irradiation, cells were incubated in a humidified incubator (5% $CO_2$ in air at 37° C.) for 24 h until cell viability assay. The cell viability was assessed by the XTT assay. 500 mg XTT (sodium 3'-[phenyl-aminocarbonyl)-3,4-tetrazolium]-bis(4-methoxy-6-nitro)benzene sulfonic acid, Applichem GmbH) is dissolved in 500 ml PBS-Buffer (without $Ca^{2+}$ and $Mg^{2+}$) and sterile filtered. Solution was stored in the dark at −20° C. until use. A sterile solution containing PMS (N-methyl dibenzopyrazine methyl sulfate, Applichem GmbH) was needed as an activation reagent for the XTT. 0.383 mg PMS was dissolved in 1 ml PBS-Buffer. The solution should be stored frozen and should not be exposed to light. The XTT reagent solution was thawed in a 37° C. water bath and the activation solution (PMS) was added immediately prior to use. To prepare a reaction solution sufficient for one micro plate (96 wells), 0.1 ml activation solution (PMS) was given to 5 ml XTT reagent. The medium in the micro plate was exchanged with RPMI without phenol red and 10% FCS (100 μl) prior adding 50 μl XTT reaction solution per well. The micro plate was incubated for 2-3 hours at 37° C. and 5% $CO_2$ until an orange dye was formed. The micro plate has been shaken gently to evenly distribute the dye in the wells. The absorbance of the samples was measured with a microplate reader (Infinite 200, Tecan Group Ltd.) at a wavelength of 490 nm.

FIGS. 1 to 15 of examples 4.1 to 4.15 illustrate the photodynamic activity ('with light' means phototoxicity) of selected compounds according to embodiments of present disclosure. It is to be noted that the compounds are also active against the macrophage cell line J774A.1. As macrophages are relevant in inflammatory processes, the compounds of the present invention may also be applied in the diagnosis and treatment of inflammatory diseases, like arthritis or otitis media.

4.1 Cell test of chlorido(5-pentafluorophenyldipyrrinato)-(pentamethylcyclopentadienyl)-iridium(III) shown in FIG. 1

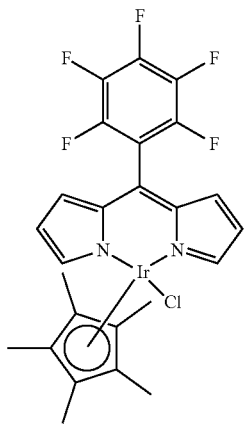

Figure 2:
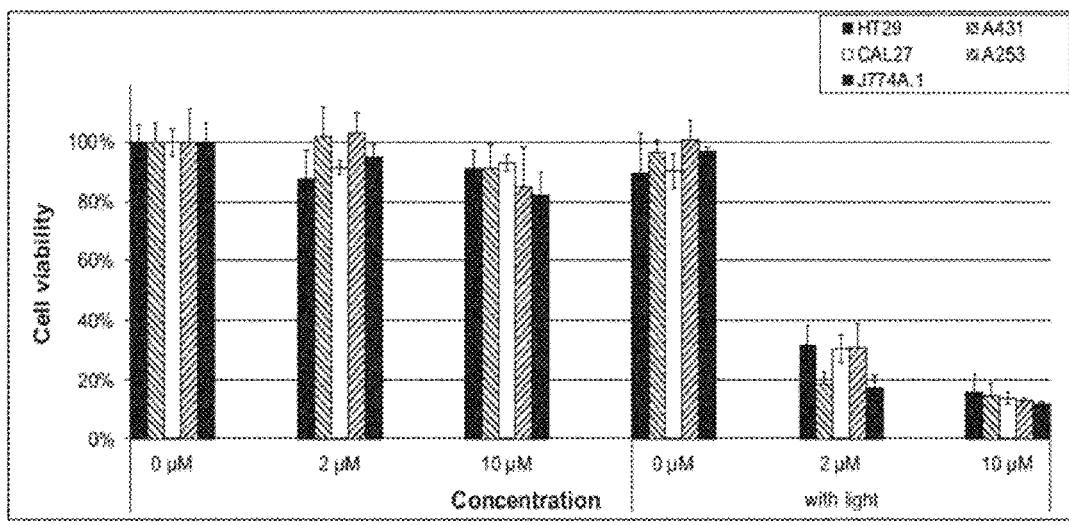
FIG. 2 illustrates the photodynamic activity ('with light' means phototoxicity) of {5-[4-(N-butylamino)-2,3,5,6-tetrafluorophenyl]dipyrrinato}chlorido-(pentamethylcyclopentadienyl)iridium(III) tested in selected cell lines.

4.2 Cell test of {5-[4-(N-butylamino)-2,3,5,6-tetrafluorophenyl]dipyrrinato}chlorido-(pentamethylcyclopentadienyl)iridium(III) shown in FIG. 2

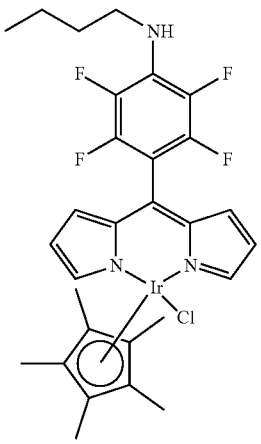

Figure 3:
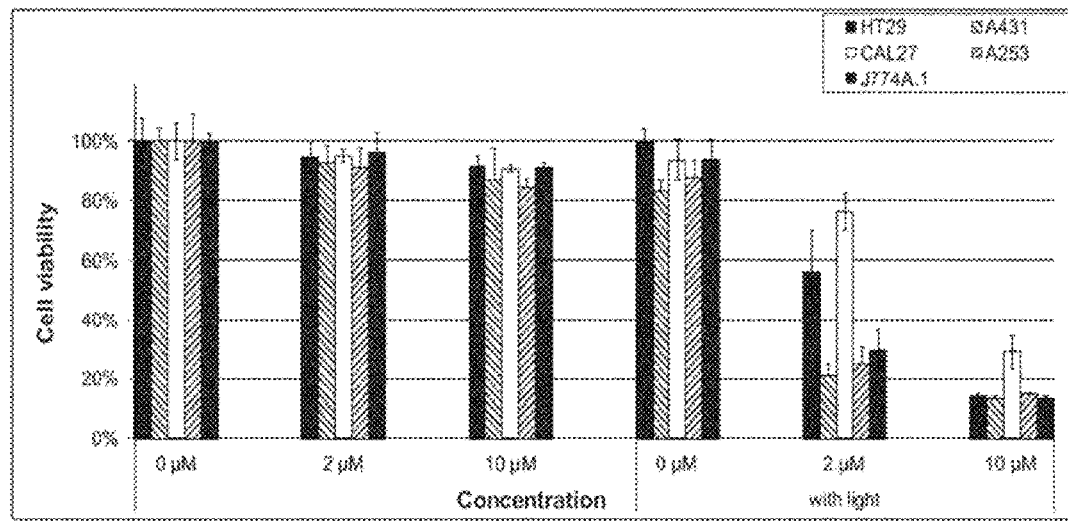
FIG. 3 illustrates the photodynamic activity ('with light' means phototoxicity) of [5-(4-butyloxy-2,3,5,6-tetrafluorophenyl)dipyrrinato]chlorido-(pentamethylcyclopentadienyl)iridium(III) tested in selected cell lines.

4.3 Cell test of [5-(4-butyloxy-2,3,5,6-tetrafluorophenyl)dipyrrinato]chlorido-(pentamethylcyclopentadienyl)iridium(III) shown in FIG. 3

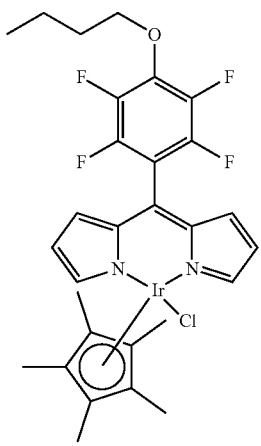

Figure 4:
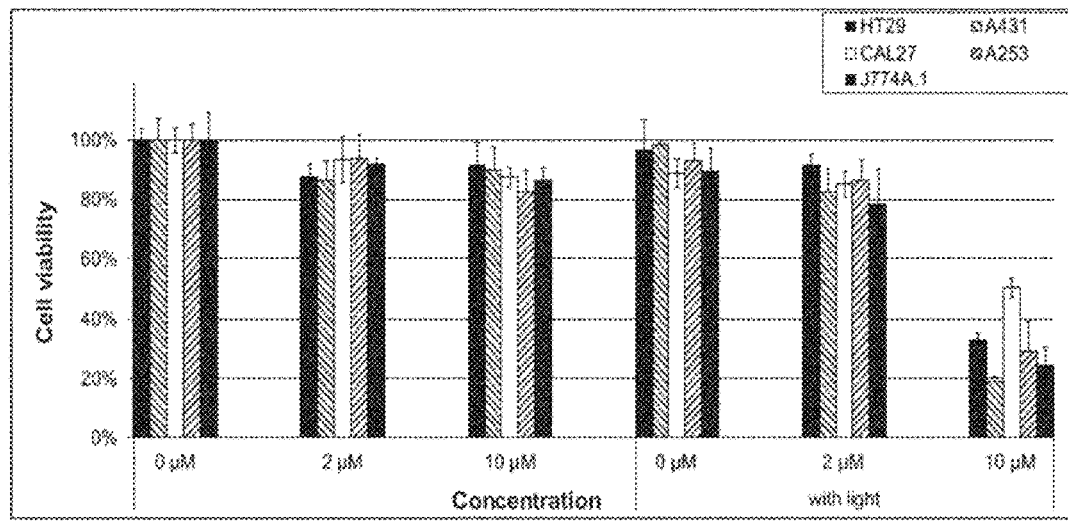
FIG. 4 illustrates the photodynamic activity ('with light' means phototoxicity) of chlorido{5-[4-(N,N-dibutylamino)-3-nitrophenyl]dipyrrinato}-(pentamethyl-cyclopentadienyl)iridium(III) tested in selected cell lines.

4.4 Cell test of chlorido{5-[4-(N,N-dibutylamino)-3-nitrophenyl]dipyrrinato}-(pentamethyl-cyclopentadienyl)iridium(III) shown in FIG. 4

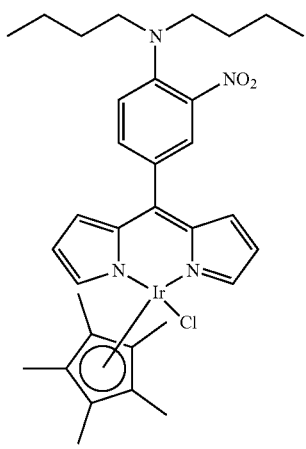

Figure 5:
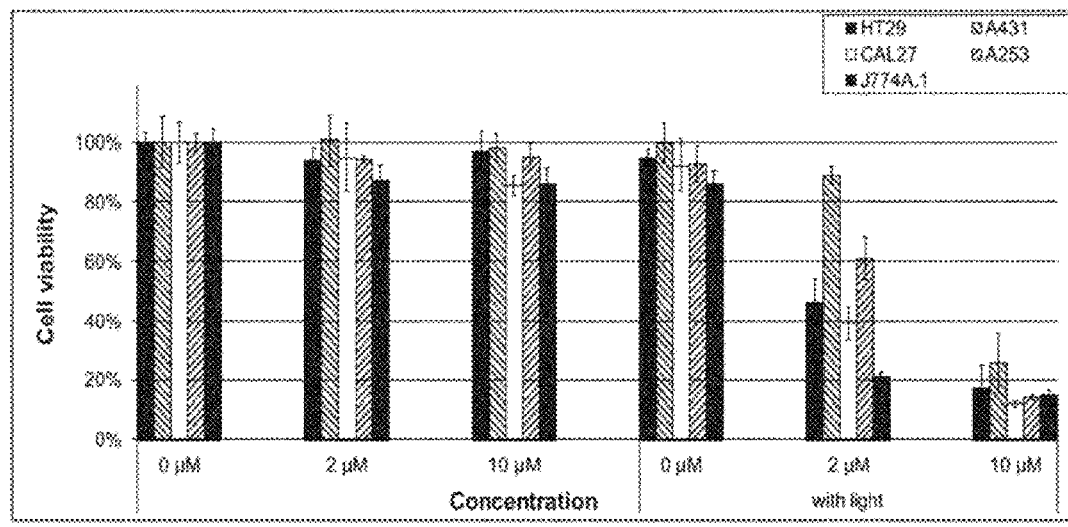
FIG. 5 illustrates the photodynamic activity ('with light' means phototoxicity) of chlorido(5-pentafluorophenyl-1,3,7,9-tetramethyldipyrrinato)-(pentamethyl-cyclopentadienyl)iridium(III) tested in selected cell lines.

4.5 Cell test of chlorido(5-pentafluorophenyl-1,3,7,9-tetramethyldipyrrinato)-(pentamethyl-cyclopentadienyl)iridium(III) shown in FIG. 5

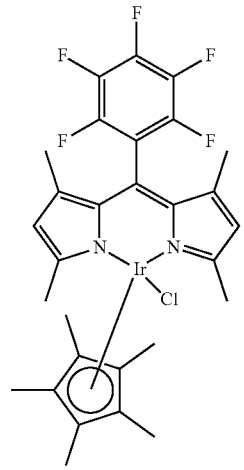

Figure 6:
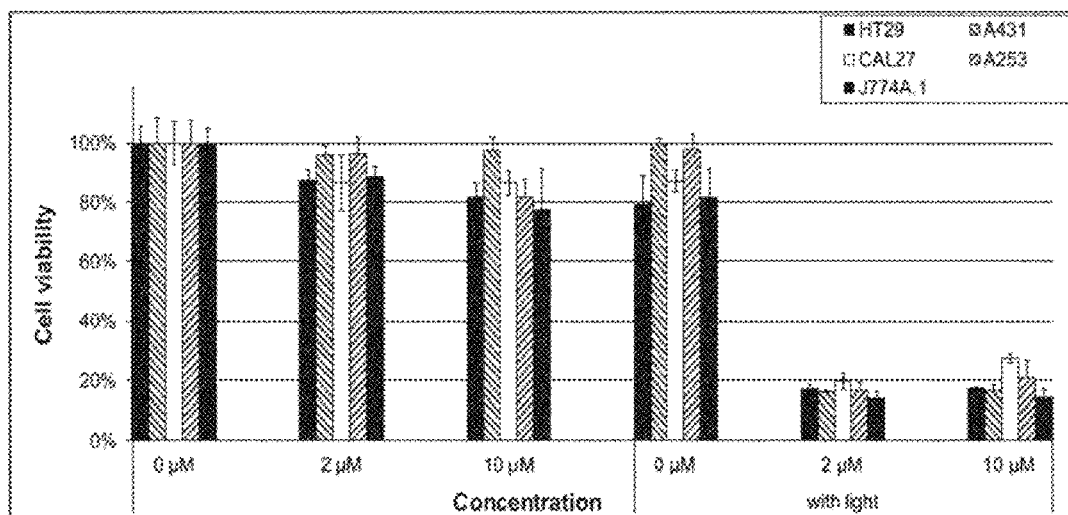
FIG. 6 illustrates the photodynamic activity ('with light' means phototoxicity) of {5-[4-(N-2-hydroxyethylamino)-2,3,5,6-tetrafluorophenyl]dipyrrinato}bis(2-phenyl-pyridyl)iridium(III) tested in selected cell lines.

4.6 Cell test of {5-[4-(N-2-hydroxyethylamino)-2,3,5,6-tetrafluorophenyl]dipyrrinato}bis(2-phenylpyridyl)iridium(III) shown in FIG. 6

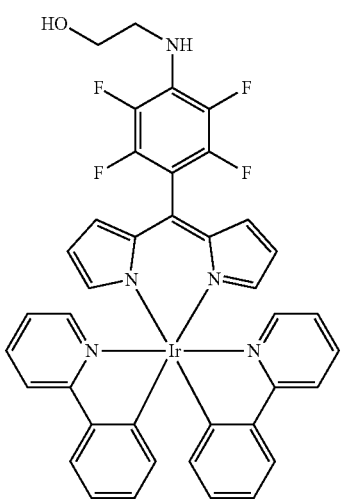

Figure 7:
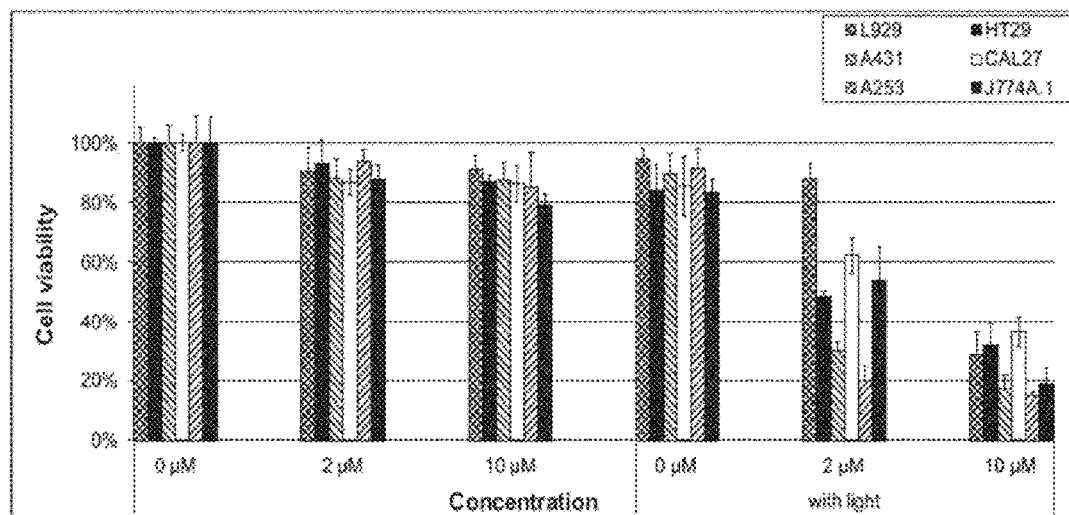
FIG. 7 illustrates the photodynamic activity ('with light' means phototoxicity) of {5-[4-(N-2-hydroxyethylamino)-3-nitrophenyl]dipyrrinato}bis(2-phenylpyridyl)iridium(III) tested in selected cell lines.

4.7 Cell test of {5-[4-(N-2-hydroxyethylamino)-3-nitrophenyl]dipyrrinato}bis(2-phenylpyridyl)iridium (III) shown in FIG. 7

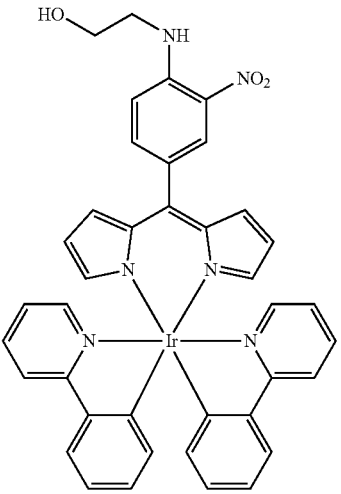

Figure 8:
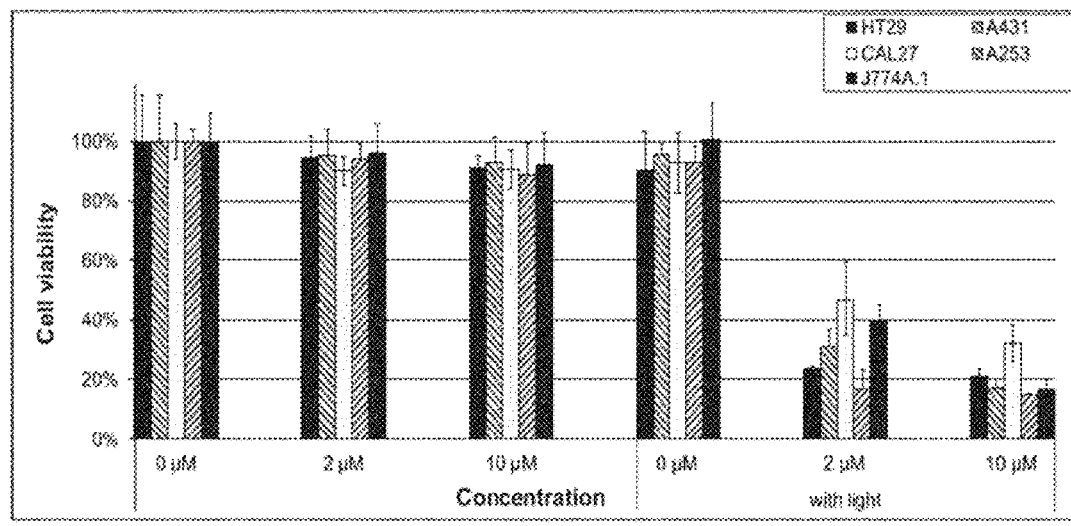
FIG. 8 illustrates the photodynamic activity ('with light' means phototoxicity) of {5-[4-(N-1-hydroxymethyl-2-hydroxyethylamino)-3-nitrophenyl]dipyrrinato}bis(2-phenylpyridyl)iridium(III) tested in selected cell lines.

4.8 Cell test of {5-[4-(N-1-hydroxymethyl-2-hydroxyethylamino)-3-nitrophenyl]dipyrrinato}bis(2-phenylpyridyl)iridium(III) shown in FIG. 8

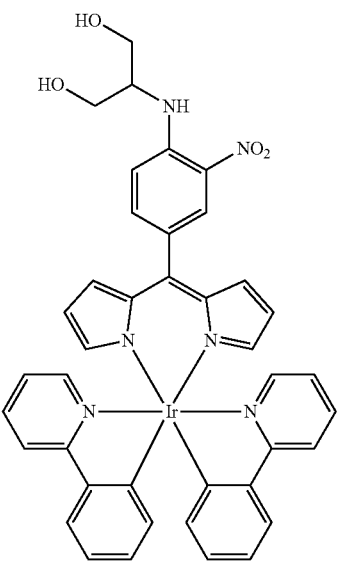

Figure 9:
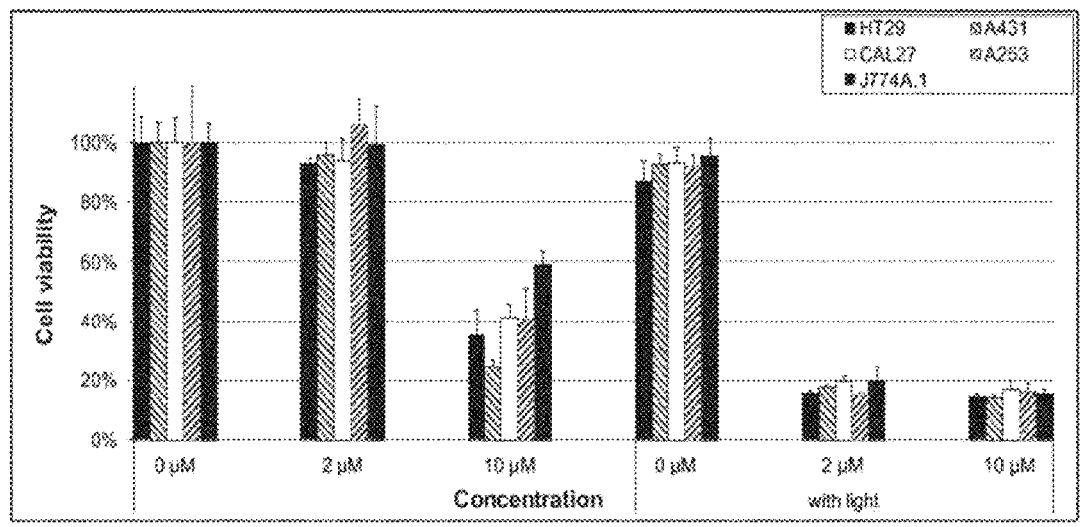
FIG. 9 illustrates the photodynamic activity ('with light' means phototoxicity) of bis(2-phenylpyridyl){5-[2,3,5,6-tetrafluoro-4-(1'-thio-β-D-glucosyl)phenyl]dipyrrinato}iridium(III) tested in selected cell lines.

4.9 Cell test of bis(2-phenylpyridyl){5-[2,3,5,6-tetrafluoro-4-(1'-thio-β-D-glucosyl)phenyl]dipyrrinato}iridium(III) shown in FIG. 9

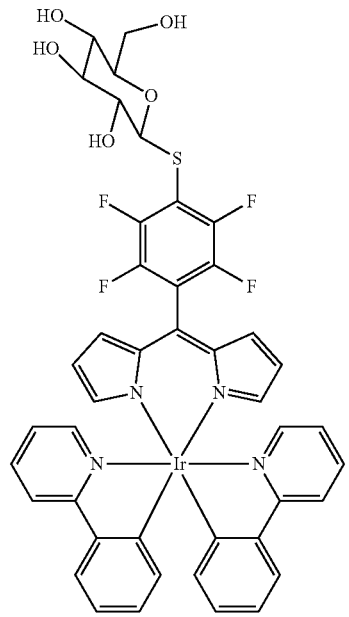

Figure 10:
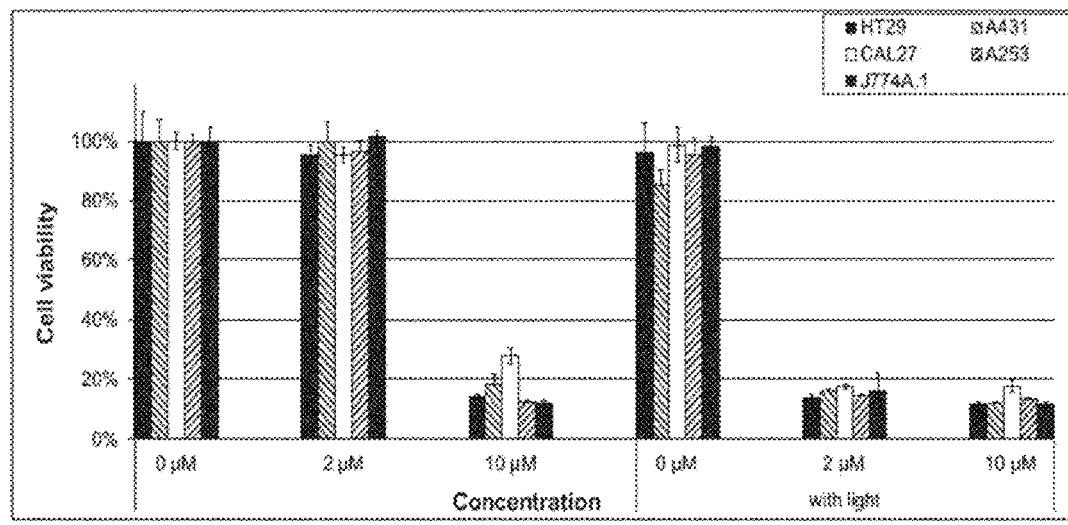
FIG. 10 illustrates the photodynamic activity ('with light' means phototoxicity) of bis(2-phenylpyridyl){5-[2,3,5,6-tetrafluoro-4-(1'-thio-β-D-galactosyl)phenyl]dipyrrinato}iridium(III) tested in selected cell lines.

4.10 Cell test of bis(2-phenylpyridyl){5-[2,3,5,6-tetrafluoro-4-(1'-thio-β-D-galactosyl)phenyl]dipyrrinato}iridium(III) shown in FIG. 10

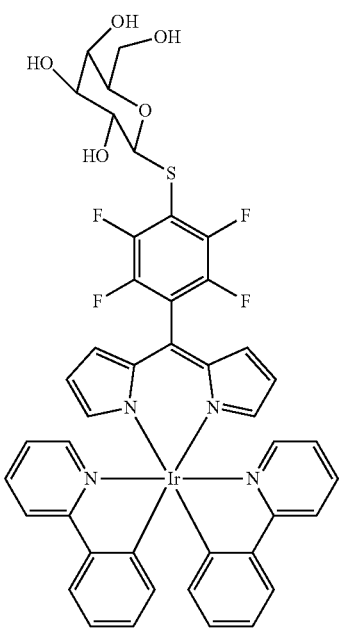

Figure 11:
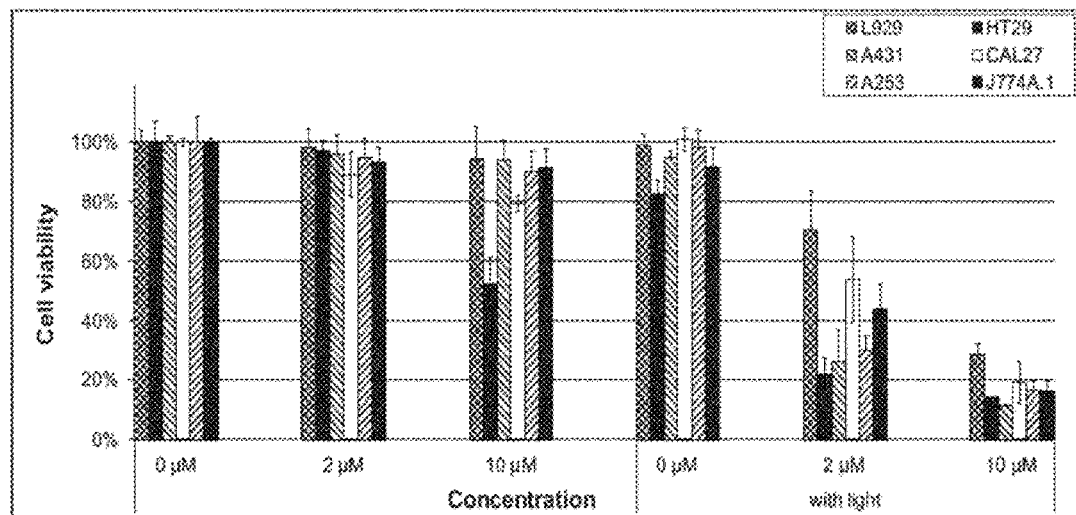
FIG. 11 illustrates the photodynamic activity ('with light' means phototoxicity) of {5-[3-nitro-4-(1'-thio-β-D-glucosyl)phenyl]dipyrrinato}bis(2-phenylpyridyl)iridium(III) tested in selected cell lines.

4.11 Cell test of {5-[3-nitro-4-(1′-thio-β-D-glucosyl)phenyl]dipyrrinato}bis(2-phenylpyridyl)iridium (III) shown in FIG. 11

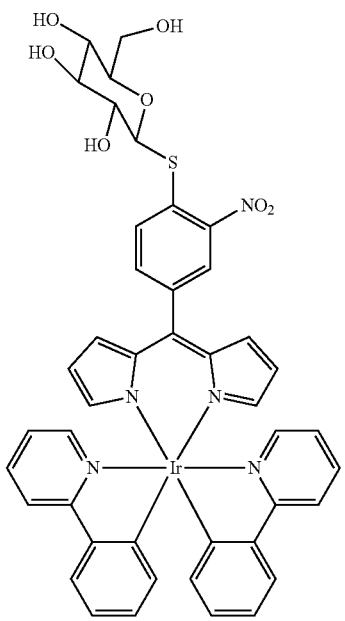

Figure 12:
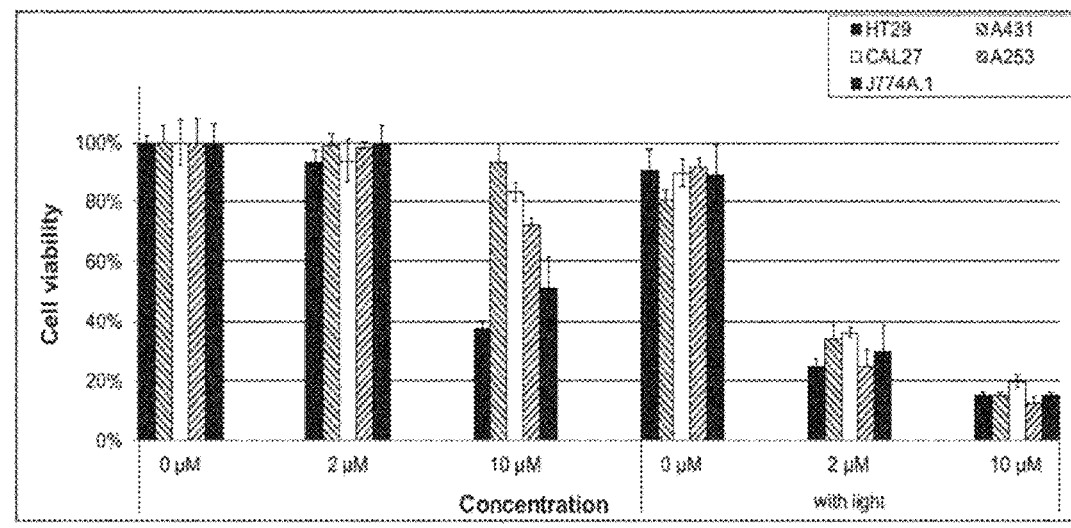
FIG. 12 illustrates the photodynamic activity ('with light' means phototoxicity) of {5-[3-nitro-4-(1'-thio-β-D-galactosyl)phenyl]dipyrrinato}bis(2-phenylpyridyl)iridium(III) tested in selected cell lines.

4.12 Cell test of {5-[3-nitro-4-(1′-thio-β-D-galactosyl)phenyl]dipyrrinato}bis(2-phenylpyridyl)iridium (III) shown in FIG. 12

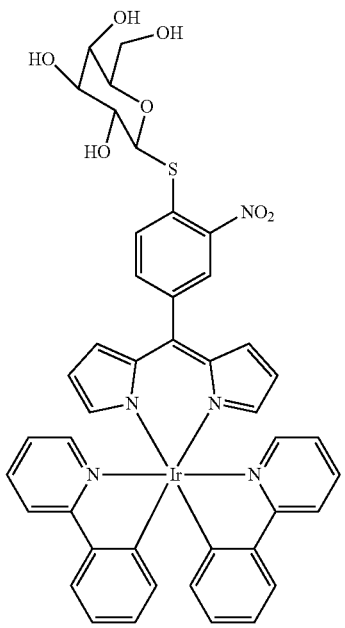

Figure 13:
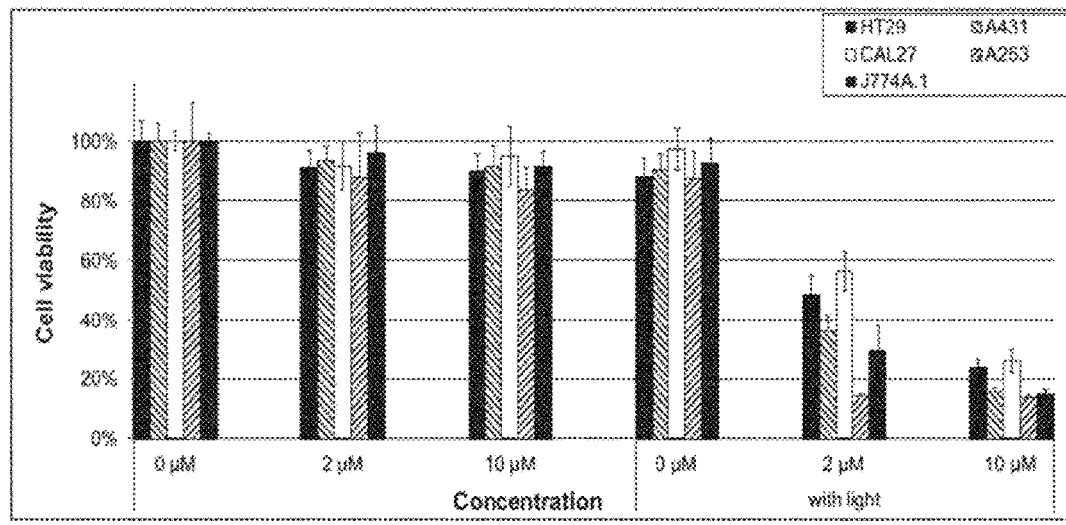
FIG. 13 illustrates the photodynamic activity ('with light' means phototoxicity) of bis(2-Phenylpyidyl){5-[4-(N-prop-2-ynylamino)-2,3,5,6-tetrafluorophenyl]dipyrrinato}iridium(III) tested in selected cell lines.

4.13 Cell test of bis(2-Phenylpyridyl){5-[4-(N-prop-2-ynylamino)-2,3,5,6-tetrafluorophenyl]dipyrrinato}iridium(III) shown in FIG. 13

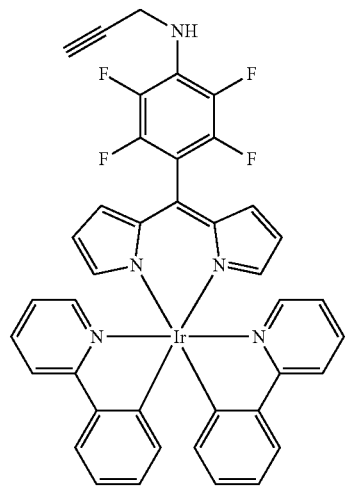

Figure 14:
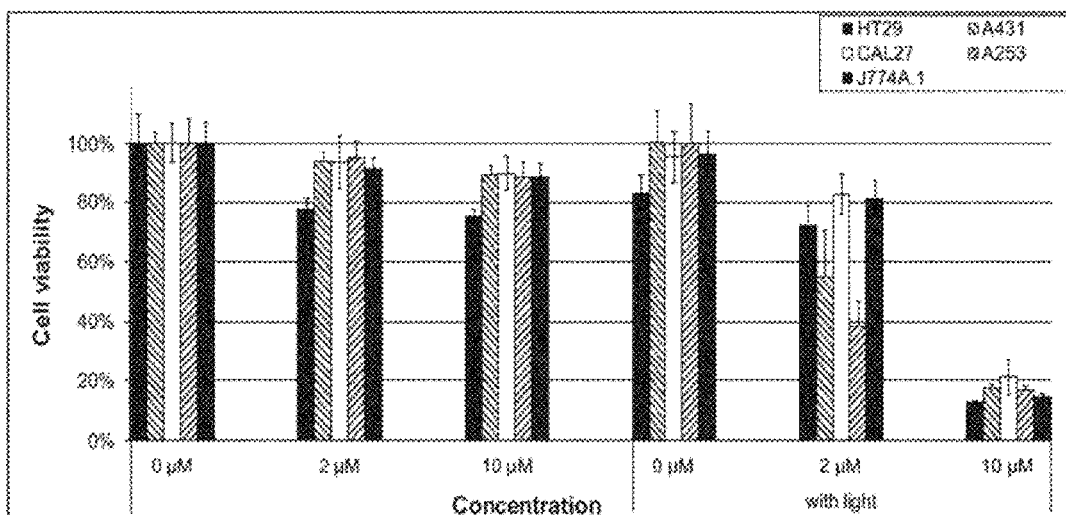
FIG. 14 illustrates the photodynamic activity ('with light' means phototoxicity) of bis(2-Phenylpyridyl){5-[4-(prop-2-ynyloxy)-2,3,5,6-tetrafluorophenyl]dipyrrinato}iridium(III) tested in selected cell lines.

4.14 Cell test of bis(2-Phenylpyridyl){5-[4-(prop-2-ynyloxy)-2,3,5,6-tetrafluorophenyl]dipyrrinato}iridium(III) shown in FIG. 14

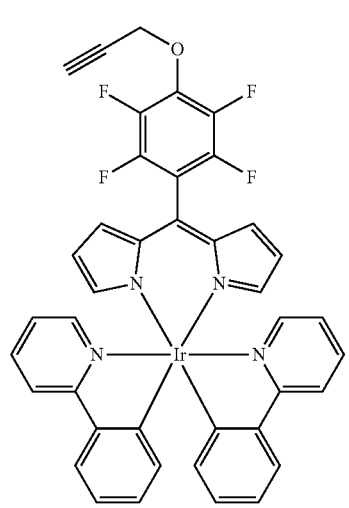

Figure 15:
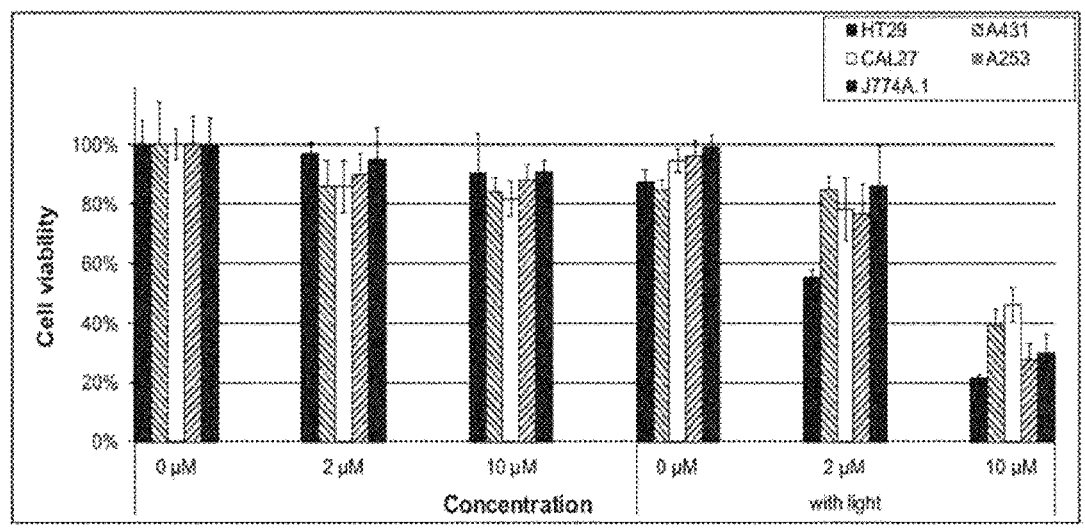
FIG. 15 illustrates the photodynamic activity ('with light' means phototoxicity) of {5-[3-nitro-4-(N-prop-2-ynylamino)phenyl]dipyrrinato}bis(2-phenylpyridyl)iridium(III) tested in selected cell lines.

4.15 Cell test of {5-[3-nitro-4-(N-prop-2-ynylamino)phenyl]dipyrrinato}bis(2-phenylpyridyl)iridium(III) shown in FIG. 15

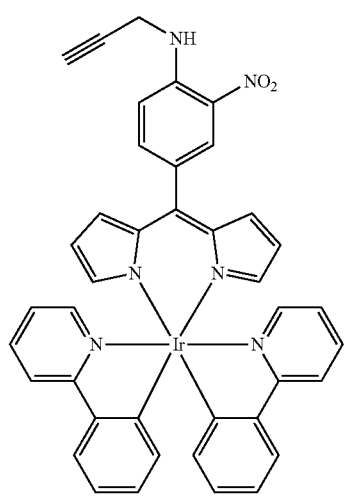

Example 5

Antibacterial Testing

The organisms studied were *Staphylococcus aureus* DSM 1104, Gram-positive and *Pseudomonas aeruginosa* DSM 1117, Gram-negative.

Cultures cells are suspended in sterile phosphate-buffered saline (PBS) or sterile PBS supplemented with 10% sterile horse blood serum. The bacterial suspensions are placed into sterile black well plates with clear bottoms. Concentrations of photosensitizer used in the study were as follows: 100 µM, 10 µM and 1 µM.

After an incubation time period of 30 minutes, the samples are exposed to white light, with a power density and irradiation time resulting in an energy fluency of about 100 J/cm². Control plates contained no photosensitizer and are not exposed to laser light. The control samples for dark toxicity are only exposed to photosensitizer without any illumination.

After irradiation, the samples are removed and suspended again in the culture media. The numbers of colony-forming units (CFU/ml) are enumerated after an adequate incubation time period.

The FIGS. 16 to 29 corresponding to examples 5.1 to 5.14 illustrate the effect of the iridium complexes according to embodiments of present disclosure against bacteria, the Gram-positive germ *Staphylococcus aureus* (5.1 to 5.14) as well as the Gram-negative *Pseudomonas aeruginosa* (5.1 to 5.4). As can be seen from the examples, selected compounds (5.1 to 5.6, 5.8, 5.11, 5.12) show a high antibacterial activity against *S. aureus* even in the absence of light exemplifying their principal suitability for a systemic treatment, especially since the compounds are on the other hand non-toxic to cells in the absence of light (cf. example 4, e.g. 4.2, 4.3, 4.4). For examples 5.1 to 5.7 and 5.12 antibacterial activity is also observed in the presence of complex media (serum addition).

Figure 16A:
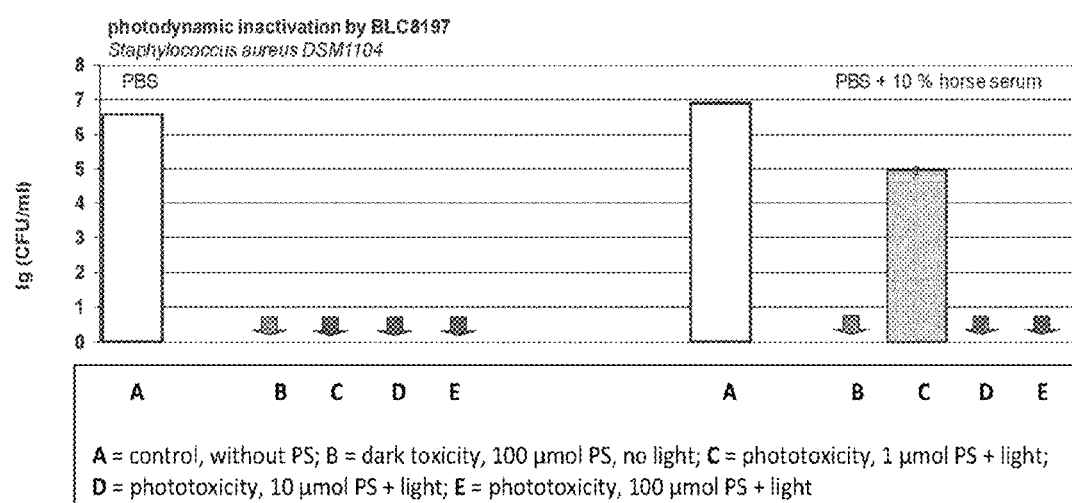
FIG. 16A illustrates the antibacterial effect of chlorido(5-pentafluorophenyldipyrrinato)-(pentamethylcyclopentadienyl)iridium(III) against *S. aureus*.
Figure 16B:
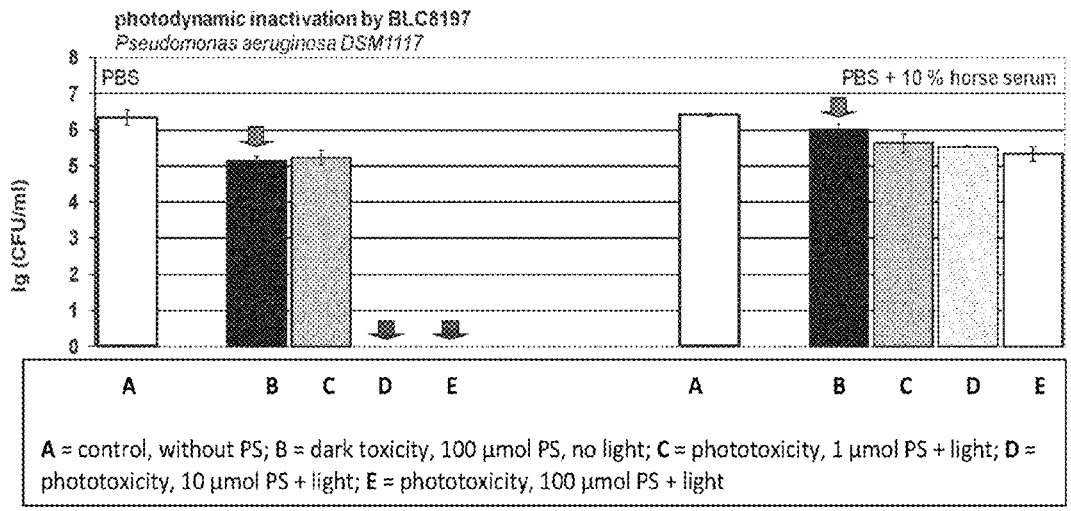
FIG. 16B illustrates the antibacterial effect of chlorido(5-pentafluorophenyldipyrrinato)-(pentamethylcyclopentadienyl)iridium(III) against *Pseudomonas aeruginosa*.

5.1 Antibacterial test of chlorido(5-pentafluorophenyldipyrrinato)-(pentamethylcyclopentadienyl)iridium(III) against *S. aureus* is shown in FIG. 16A and against *Pseudomonas aeruginosa* in FIG. 16B

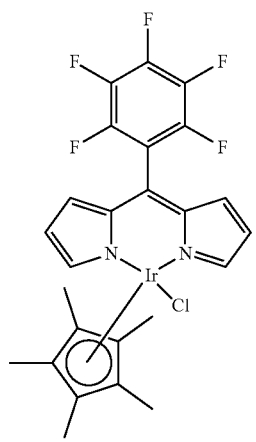

Figure 17A:
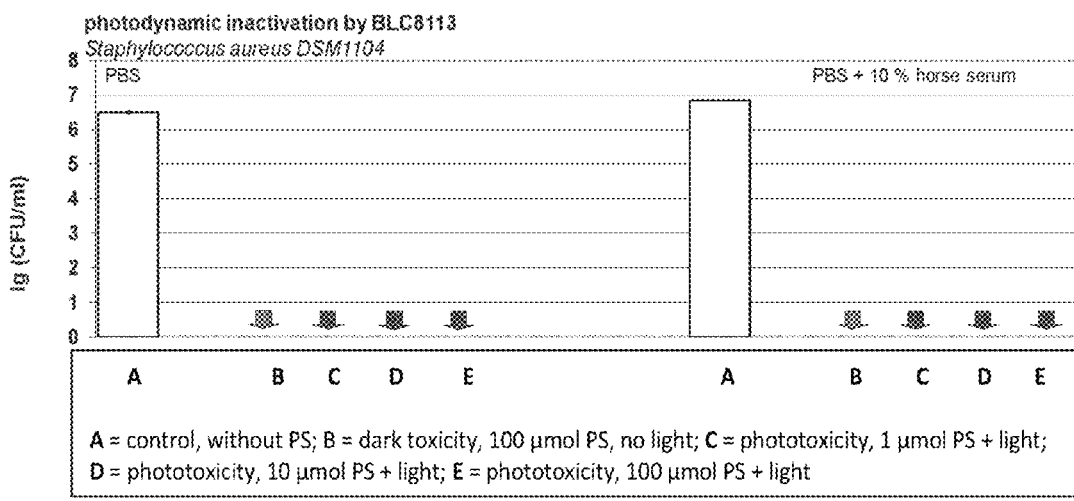
FIG. 17A illustrates the antibacterial effect of {5-[4-(N-butylamino)-2,3,5,6-tetrafluorophenyl]dipyrrinato}chlorido-(pentamethylcyclopentadienyl)iridium(III) against *S. aureus*.
Figure 17B:
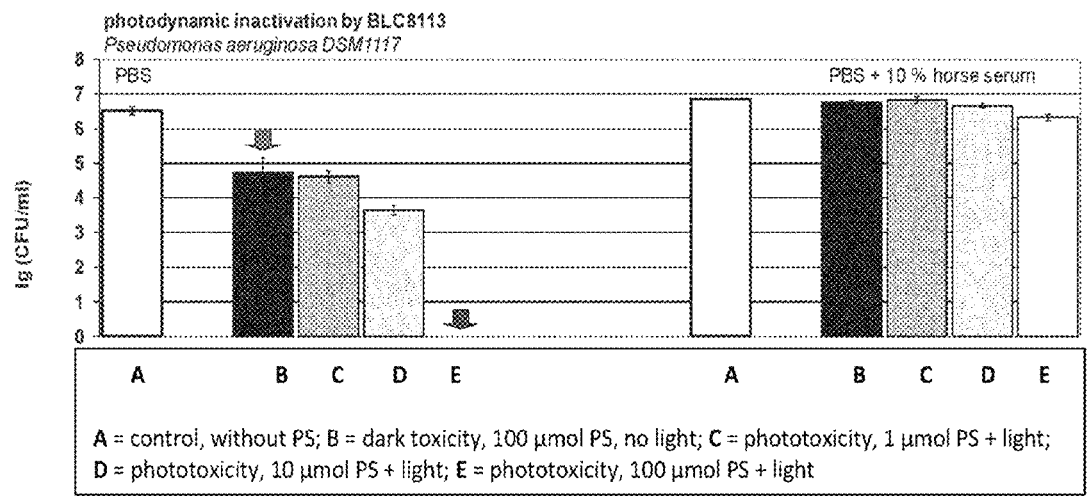
FIG. 17B illustrates the antibacterial effect of {5-[4-(N-butylamino)-2,3,5,6-tetrafluorophenyl]dipyrrinato}chlorido-(pentamethylcyclopentadienyl)iridium(III) against *Pseudomonas aeruginosa*.

5.2 Antibacterial test of {5-[4-(N-butylamino)-2,3,5,6-tetrafluorophenyl]dipyrrinato}chlorido-(pentamethylcyclopentadienyl)iridium(III) against *S. aureus* is shown in FIG. 17A and against *Pseudomonas aeruginosa* in FIG. 17B

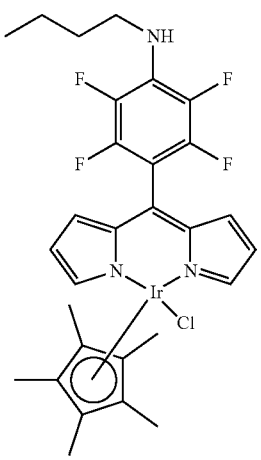

Figure 18A:
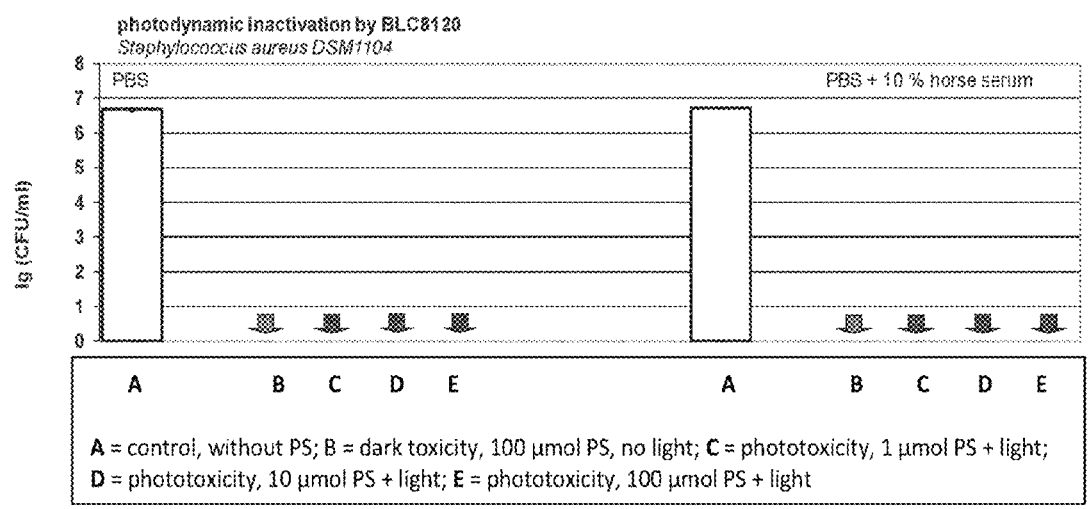
FIG. 18A illustrates the antibacterial effect of [5-(4-butyloxy-2,3,5,6-tetrafluorophenyl)dipyrrinato]chlorido-(pentamethylcyclopentadienyl)iridium(III) against *S. aureus*.
Figure 18B:
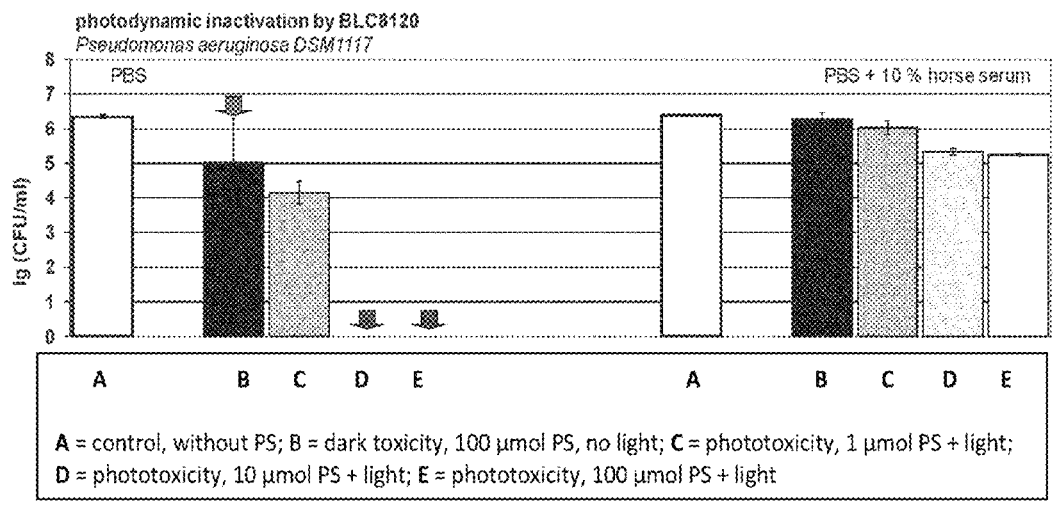
FIG. 18B illustrates the antibacterial effect of [5-(4-butyloxy-2,3,5,6-tetrafluorophenyl)dipyrrinato]chlorido-(pentamethylcyclopentadienyl)iridium(III) against *Pseudomonas aeruginosa*.
Figure 20:
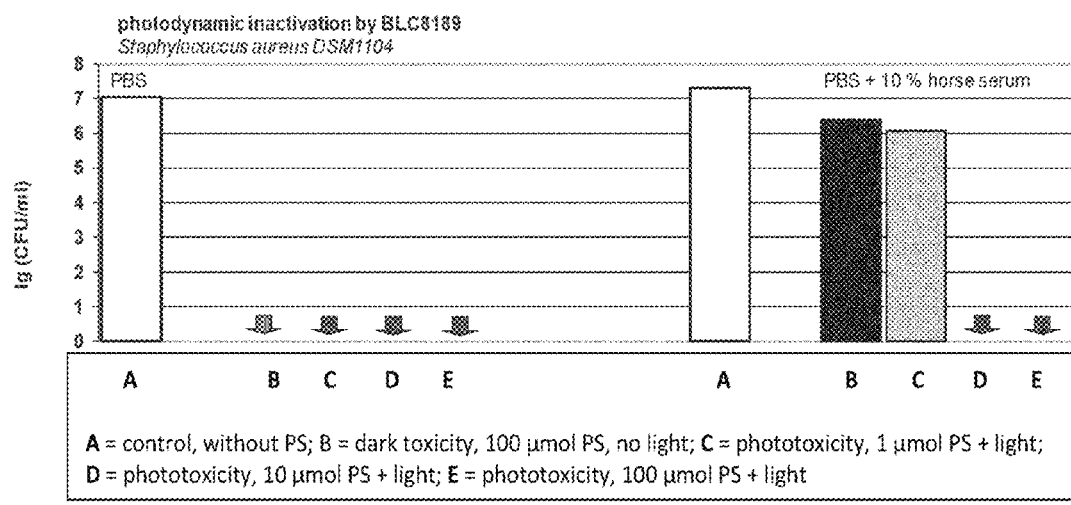
FIG. 20 illustrates the antibacterial effect of chlorido{5-[4-(N-6-methoxy-6-oxohexylamino)-3-nitrophenyl]dipyrrinato}-(pentamethylcyclopentadienyl)iridium(III) against *S. aureus*.

5.3 Antibacterial test of [5-(4-butyloxy-2,3,5,6-tetrafluorophenyl)dipyrrinato]chlorido-(pentamethylcyclopentadienyl)iridium(III) against *S. aureus* is shown in FIG. 18A and against *Pseudomonas aeruginosa* in FIG. 18B 5.5 Antibacterial test of chlorido{5-[4-(N-6-methoxy-6-oxohexylamino)-3-nitrophenyl]dipyrrinato}-(pentamethylcyclopentadienyl)iridium(III) against *S. aureus* is shown in FIG. 20

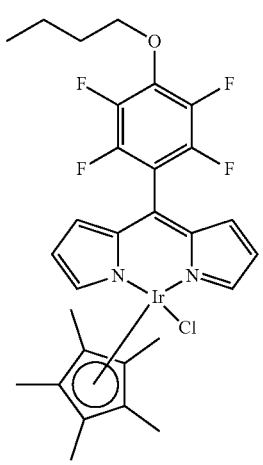

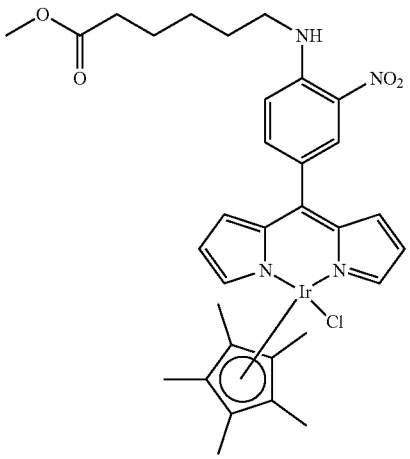

Figure 19A:
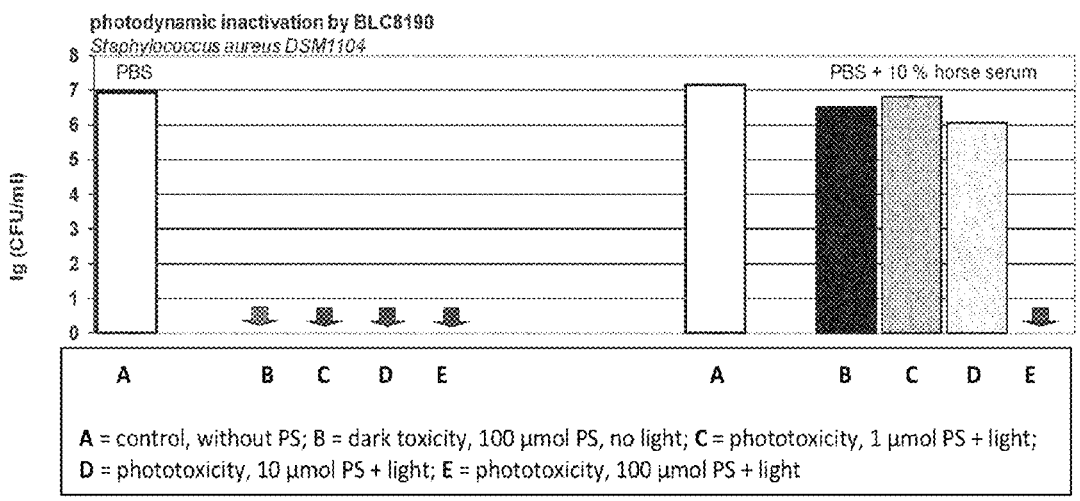
FIG. 19A illustrates the antibacterial effect of {5-[4-(N-butylamino)-3-nitrophenyl]dipyrrinato}chlorido(pentamethyl-cyclopentadienyl)iridium(III) against *S. aureus*.
Figure 19B:
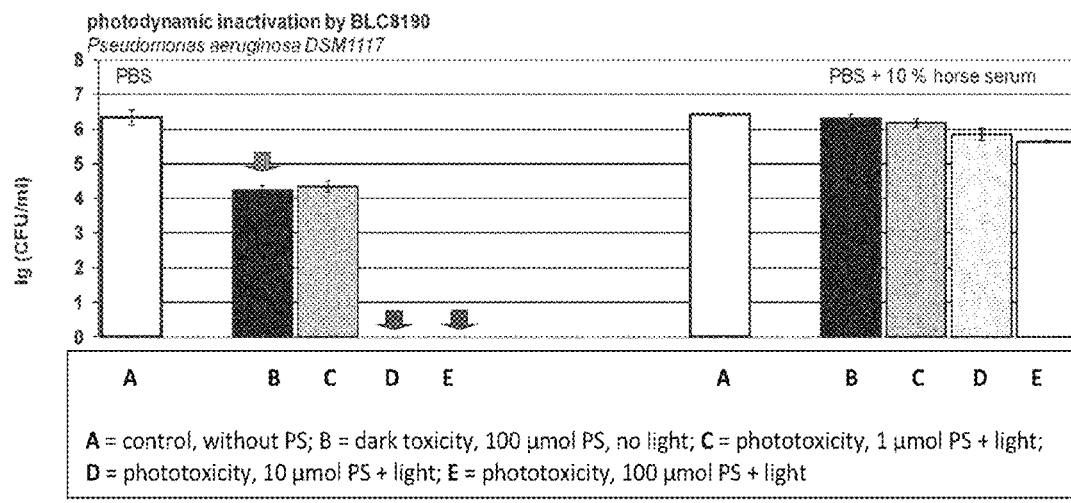
FIG. 19B illustrates the antibacterial effect of {5-[4-(N-butylamino)-3-nitrophenyl]dipyrrinato}chlorido(pentamethyl-cyclopentadienyl)iridium(III) against *Pseudomonas aeruginosa*.
Figure 21:
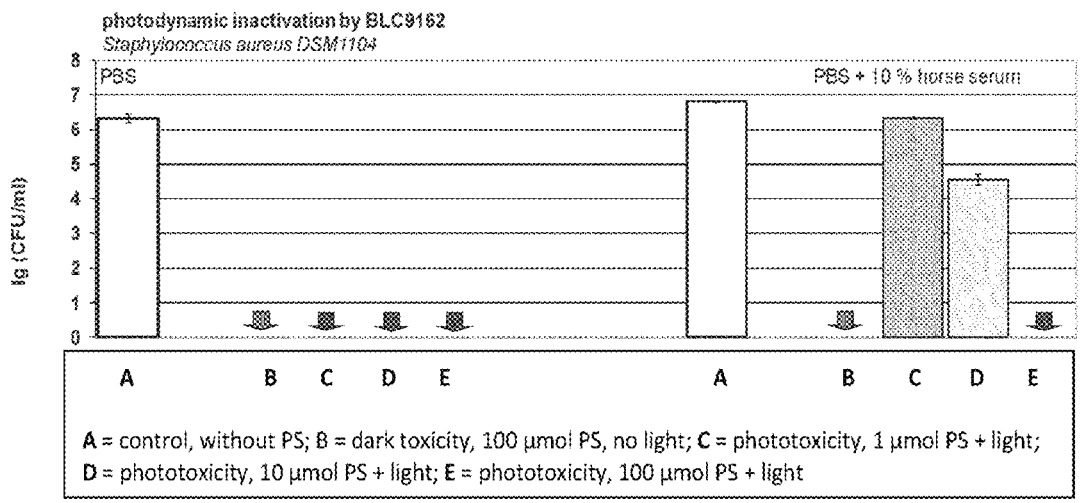
FIG. 21 illustrates the antibacterial effect of chlorido(5-[4-(N,N-dibutylamino)-3-nitrophenyl]dipyrrinato)(pentamethyl-cyclopentadienyl)iridium(III) against *S. aureus*.

5.4 Antibacterial test of {5-[4-(N-butylamino)-3-nitrophenyl]dipyrrinato}chlorido(pentamethyl-cyclopentadienyl)iridium(III) against *S. aureus* is shown in FIG. 19A and against *Pseudomonas aeruginosa* in FIG. 19B 5.6 Antibacterial test of chlorido{5-[4-(N,N-dibutylamino)-3-nitrophenyl]dipyrrinato}(pentamethylcyclopentadienyl)iridium(III) against *S. aureus* is shown in FIG. 21

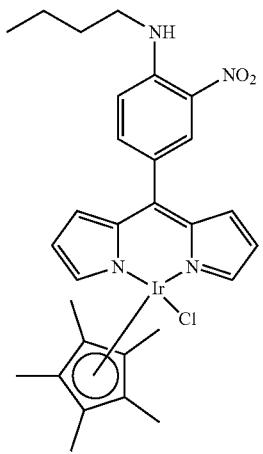

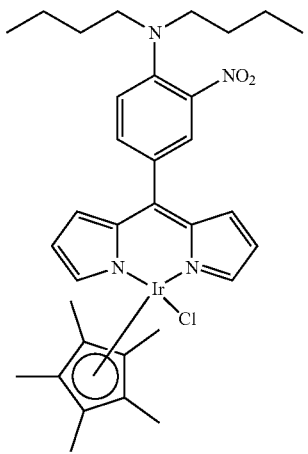

Figure 22:
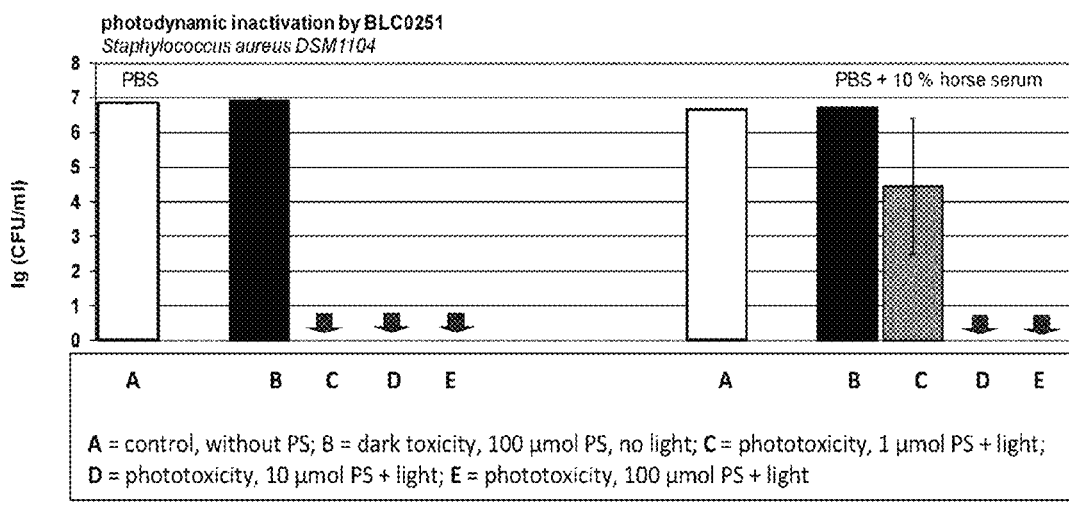
FIG. 22 illustrates the antibacterial effect of chlorido(5-pentafluorophenyl-1,3,7,9-tetramethyldipyrrinato)(pentamethyl-cyclopentadienyl)iridium(III) against *S. aureus*.

5.7 Antibacterial test of chlorido(5-pentafluorophe-nyl-1,3,7,9-tetramethyldipyrrinato)(pentamethyl-cyclopentadienyl)iridium(III) against *S. aureus* is shown in FIG. 22

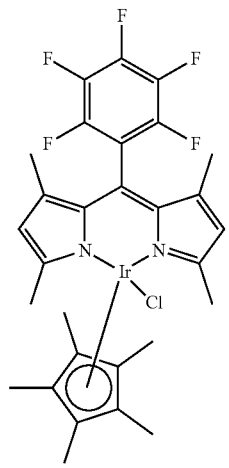

Figure 23:
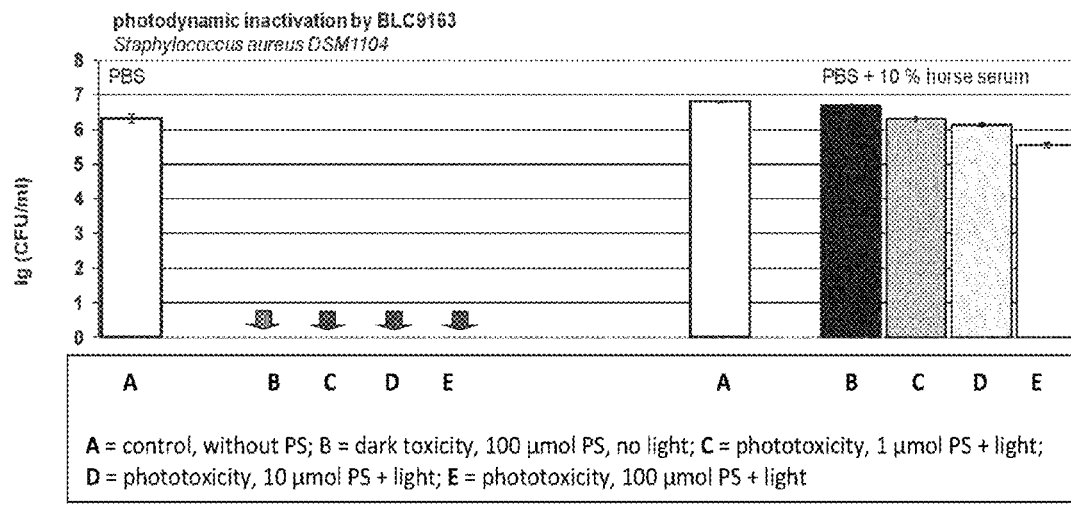
FIG. 23 illustrates the antibacterial effect of {5-[4-(N-2-hydroxyethylamino)-2,3,5,6-tetrafluorophenyl]dipyrrinato}bis(2-phenyl-pyridyl)iridium(III) against *S. aureus*.

5.8 Antibacterial test of {5-[4-(N-2-hydroxyethyl-amino)-2,3,5,6-tetrafluorophenyl]dipyrrinato}bis(2-phenyl-pyridyl)iridium(III) against *S. aureus* is shown in FIG. 23

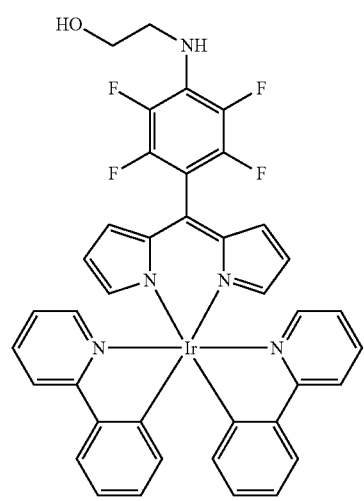

Figure 24:
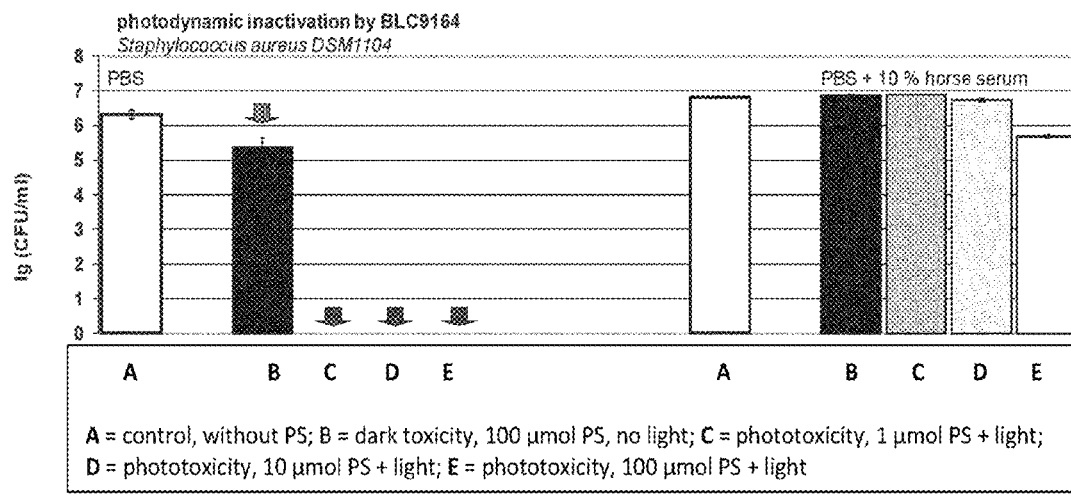
FIG. 24 illustrates the antibacterial effect of {5-[4-(N-2-hydroxyethylamino)-3-nitrophenyl]dipyrrinato}bis(2-phenylpyridyl)iridium(III) against *S. aureus*.

5.9 Antibacterial test of {5-[4-(N-2-hydroxyethyl-amino)-3-nitrophenyl]dipyrrinato}bis(2-phe-nylpyridyl)iridium(III) against *S. aureus* is shown in FIG. 24

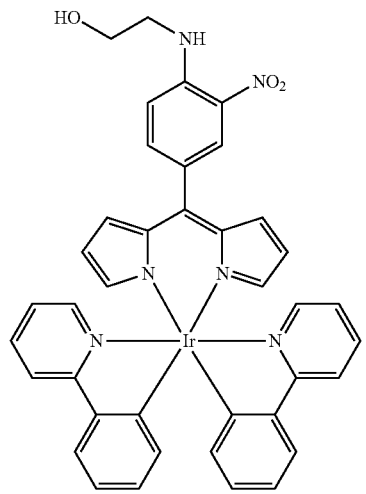

Figure 25:
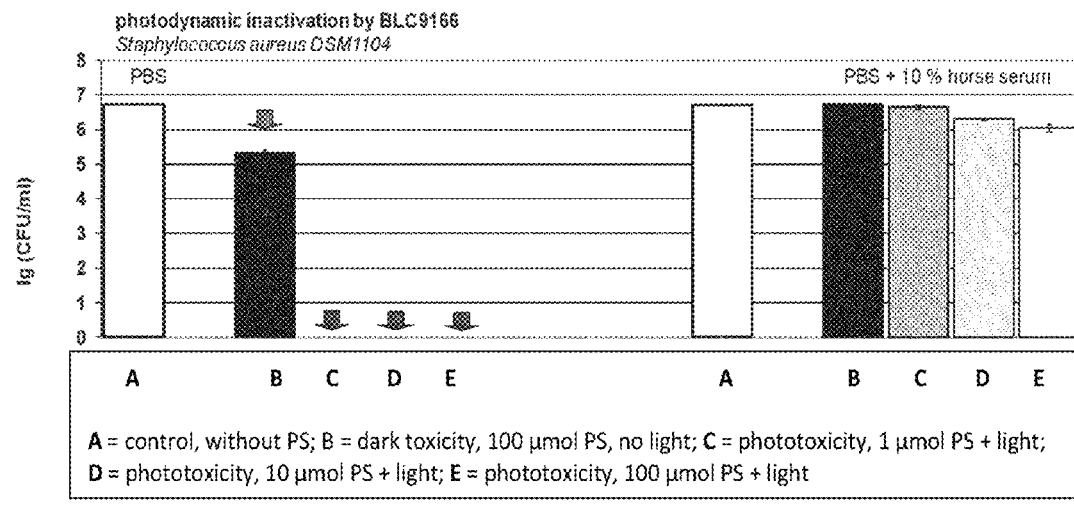
FIG. 25 illustrates the antibacterial effect of {5-[4-(N-1-hydroxymethyl-2-hydroxyethylamino)-3-nitrophenyl]dipyrrinato}bis(2-phenylpyridyl)iridium(III) against *S. aureus*.

5.10 Antibacterial test of {5-[4-(N-1-hydroxym-ethyl-2-hydroxyethylamino)-3-nitrophenyl]dipyrrinato}bis(2-phenylpyridyl)iridium(III) against *S. aureus* is shown in FIG. 25

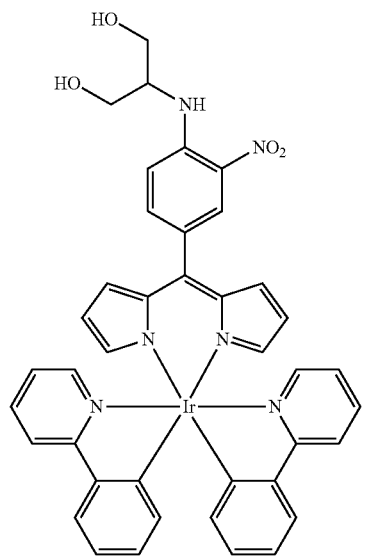

Figure 26:
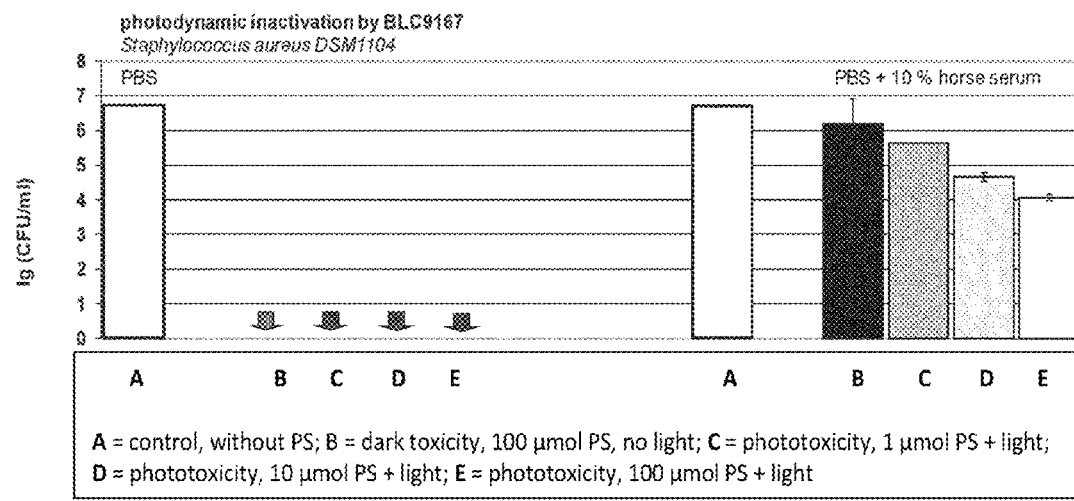
FIG. 26 illustrates the antibacterial effect of bis(2-phenylpyridyl){5-[2,3,5,6-tetrafluoro-4-(1'-thio-β-D-glucosyl)phenyl]dipyrrinato}iridium(III) against *S. aureus*.

5.11 Antibacterial test of bis(2-phenylpyridyl){5-[2,3,5,6-tetrafluoro-4-(1'-thio-β-D-glucosyl)phenyl]dipyrrinato}iridium(III) against *S. aureus* is shown in FIG. 26

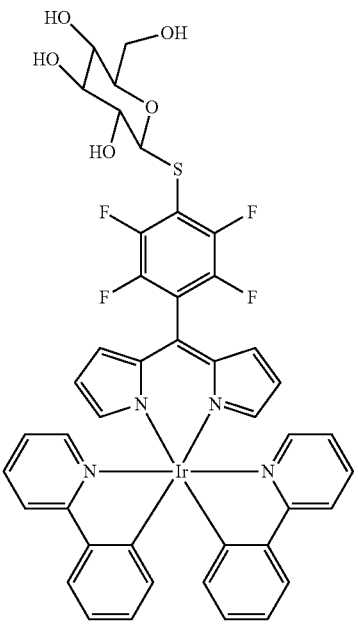

Figure 27:
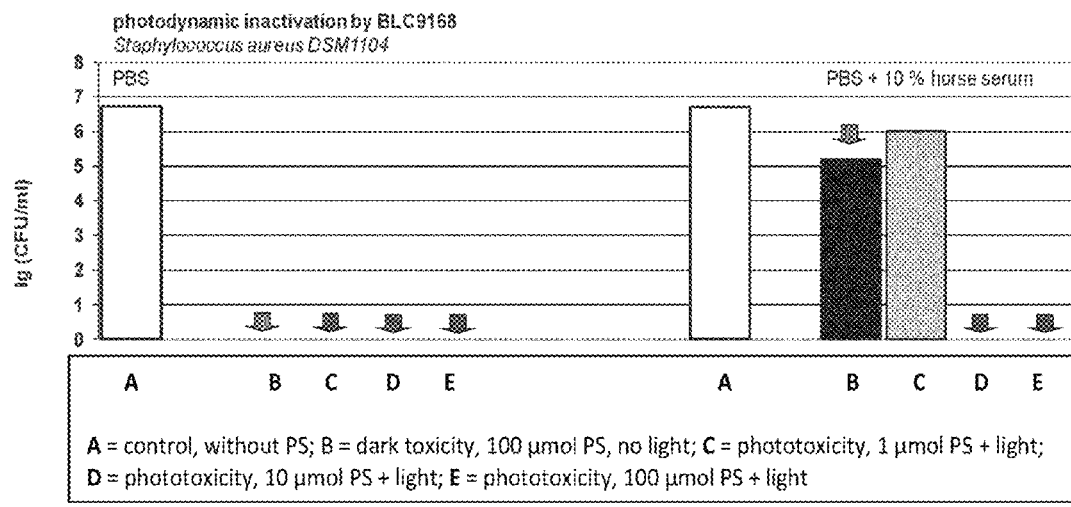
FIG. 27 illustrates the antibacterial effect of bis(2-phenylpyridyl){5-[2,3,5,6-tetrafluoro-4-(1'-thio-β-D-galactosyl)phenyl]dipyrrinato}iridium(III) against *S. aureus*.

5.12 Antibacterial test of bis(2-phenylpyridyl){5-[2,3,5,6-tetrafluoro-4-(1'-thio-β-D-galactosyl)phenyl]dipyrrinato}iridium(III) against *S. aureus* is shown in FIG. 27

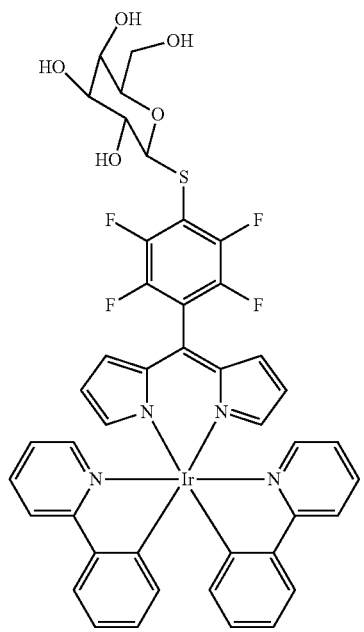

Figure 28:
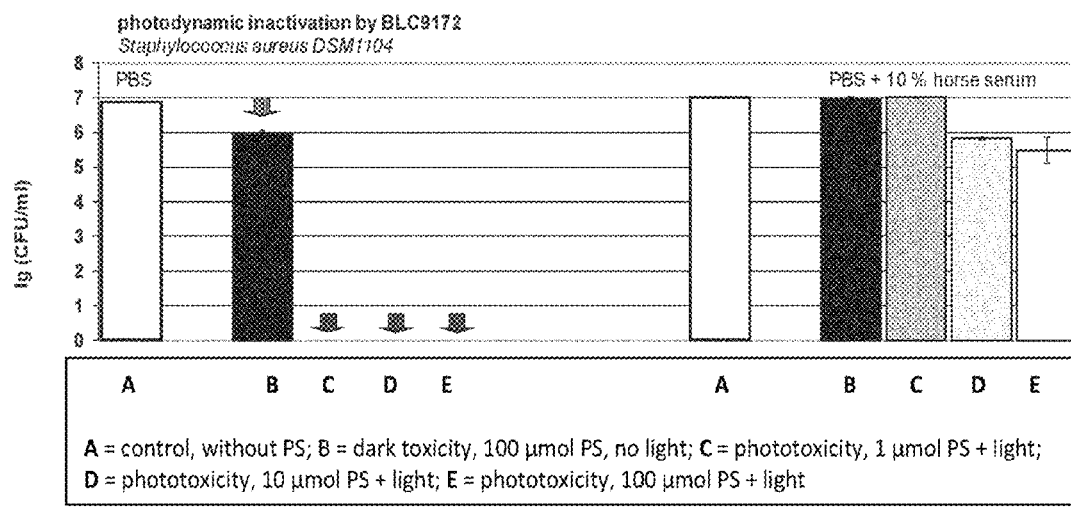
FIG. 28 illustrates the antibacterial effect of {5-[3-nitro-4-(1'-thio-β-D-glucosyl)phenyl]dipyrrinato}bis(2-phenylpyridyl)iridium(III) against *S. aureus*.

5.13 Antibacterial test of {5-[3-nitro-4-(1'-thio-β-D-glucosyl)phenyl]dipyrrinato}bis(2-phenylpyridyl)iridium(III) against *S. aureus* is shown in FIG. 28

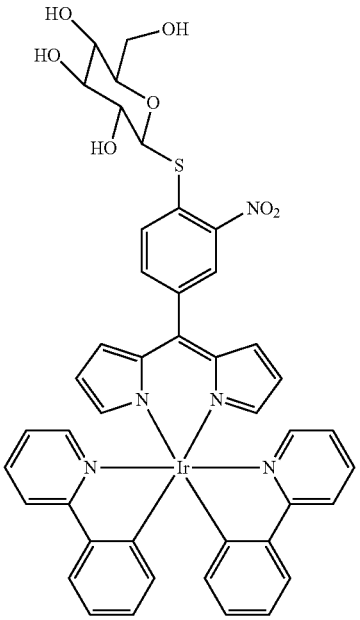

Figure 29:
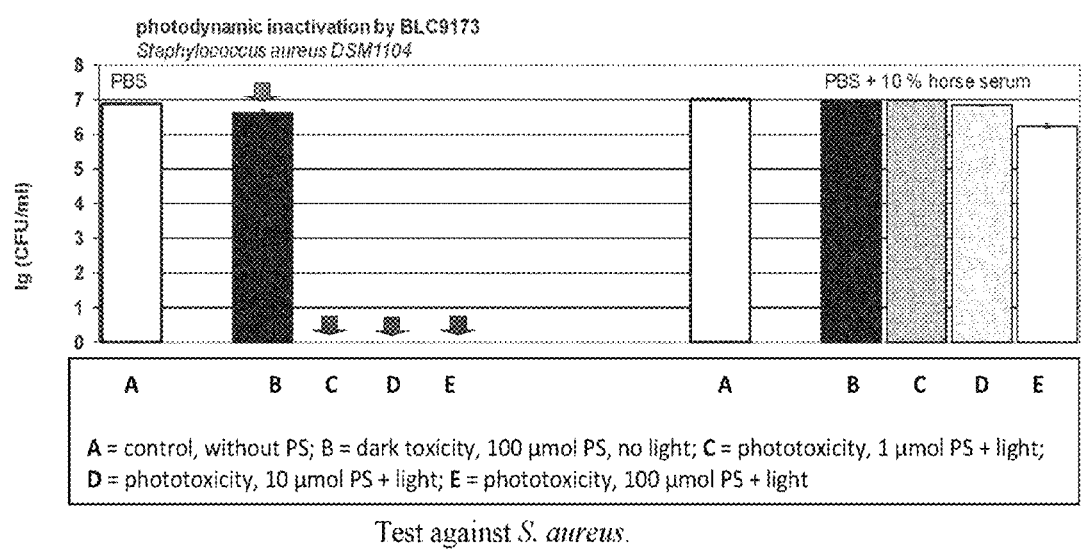
FIG. 29 illustrates the antibacterial effect of {5-[3-nitro-4-(1'-thio-β-D-galactosyl)phenyl]dipyrrinato}bis(2-phenylpyridyl)iridium(III) against *S. aureus*.

5.14 Antibacterial test of {5-[3-nitro-4-(1'-thio-β-D-galactosyl)phenyl]dipyrrinato}bis(2-phenylpyridyl)iridium(III) against *S. aureus* is shown in FIG. 29

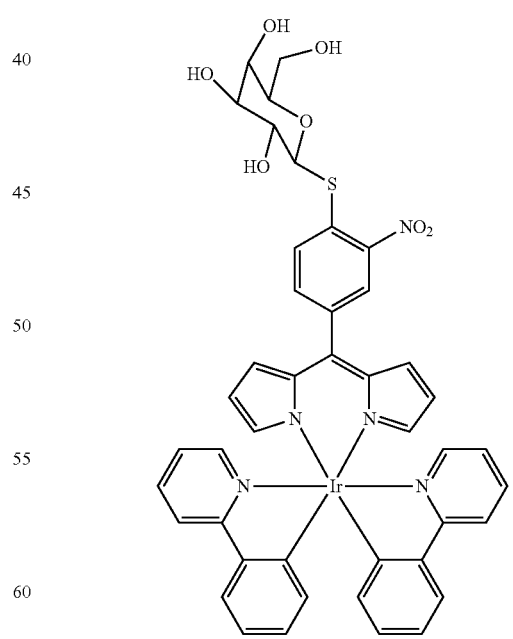

Having described preferred embodiments of the invention with reference to the accompanying examples, it is to be understood that the invention is not limited to the precise embodiments, and that various changes and modifications may be effected therein by skilled in the art without departing from the scope of the invention as defined in the appended claims.

REFERENCES

[1] B. W. Henderson, T. J. Dougherty, Photodynamic therapy, basic principles and clinical applications, New York: Marcel Dekker, 1992.

[2] J. G. Moser, Photodynamic tumor therapy. 2nd and 3rd generation photosensitizers, Amsterdam: Harwood Academic Publishers, 1998.

[3] Z. Lv, H. Wei, Q. Li, X. Su, S. Liu, K. Y. Zhang, W. Lv, Q. Zhao, X. Li, W. Huang, <<Achieving efficient photodynamic therapy under both normoxia and hypoxia using cyclometalated Ru(II) photosensitizer through type I photochemical process>>, Chem. Sci., 9, pp. 502-512, 2018.

[4] J. W. Kleinovink, P. B. van Driel, T. J. Snoeks, N. Prokopi, M. F. Fransen, L. J. Cruz, L. Mezzanotte, A. Chan, C. W. Löwik, F. Ossendorp, <<Combination of Photodynamic Therapy and Specific Immunotherapy Efficiently Eradicates Established Tumors>>, Clin. Cancer Res., 22, pp. 1459-1468, 2016.

[5] T. Maisch, <<Strategies to optimize photosensitizers for photodynamic inactivation of bacteria>>, J Photochem. Photobiol. B, 150, pp. 2-10, 2015.

[6] A. Treibs, F. H. Kreuzer, <<Difluorboryl-Komplexe von Di- und Tripyrrylmethenen>>, Justus Liebigs Ann. Chem., 718, pp. 208-223, 1968.

[7] B. F. Hohlfeld, K. J. Flanagan, N. Kulak, M. O. Senge, M. Christmann, A. Wiehe, <<Synthesis of Porphyrinoids, BODIPYs, and (Dipyrrinato)ruthenium(III) Complexes from Prefunctionalized Dipyrromethanes>>, Eur. J. Org. Chem., 4020-4033, 2019.

[8] C.-H. Lee, J. S. Lindsey, <<One-Flask Synthesis of Meso-Substituted Dipyrromethanes and Their Application in the Synthesis of Trans-Substituted Porphyrin Building Blocks>>, Tetrahedron, 50, pp. 11427-11440, 1994.

[9] H. R. A. Golf, H.-U. Reissig, A. Wiehe, <<Nucleophilic Substitution on (Pentafluorophenyl)dipyrromethane: A New Route to Building Blocks for Functionalized BODIPYs and Tetrapyrroles>, Org. Lett., 17, pp. 982-985, 2015.

[10] R. Klingenburg, C. B. W. Stark, A. Wiehe, <<Nucleophilic Thioglycosylation of Pentafluorophenyl-Substituted Porphyrinoids. Synthesis of Glycosylated Calix[n]phyrin and [28]Hexaphyrin Systems>>, Org. Lett., 21, pp. 5417-5420, 2019.

[11] B. F. Hohlfeld, B. Gitter, K. J. Flanagan, C. J. Kingsbury, N. Kulak, M. O. Senge, A. Wiehe, <<Exploring the relationship between structure and activity in BODIPYs designed for antimicrobial phototherapy>>, Org. Biomol. Chem., 18, pp. 2416-2431, 2020.

[12] C. S. Gutsche, M. Ortwerth, S. Gräfe, K. J. Flanagan, M. O. Senge, H.-U. Reissig, N. Kulak, A. Wiehe, <<Nucleophilic Aromatic Substitution on Penta¬fluoro¬phenyl-Substituted Dipyrranes and Tetrapyrroles as a Route to Multifunctionalized Chromophores for Potential Application in Photodynamic Therapy>>, Chem. Eur. J., 22, pp. 13953-13964, 2016.

[13] C. S. Gutsche, B. F. Hohlfeld, K. J. Flanagan, M. O. Senge, N. Kulak, A. Wiehe, <<Sequential Nucleophilic Substitution of the α-Pyrrole and p-ArylPositions of meso-Pentafluorophenyl-Substituted BODIPYs>>, Eur. J. Org. Chem., pp. 3187-3196, 2017.

[14] L. Yu, K. Muthukumaran, I. V. Sazanovich, C. Kirmaier, E. Hindin, J. R. Diers, P. D. Boyle, D. F. Bocian, D. Holten, J. S. Lindsey, <<Excited-State Energy-Transfer Dynamics in Self-Assembled Triads Composed of Two Porphyrins and an Intervening Bis(dipyrrinato)metal Complex>>, Inorg. Chem., 42, pp. 6629-6647, 2003.

[15] C. S. Gutsche, S. Gräfe, B. Gitter, K. J. Flanagan, M. O. Senge, N. Kulak, A. Wiehe <<Pre-/post-functionalization in dipyrrin metal complexes—antitumor and antibacterial activity of their glycosylated derivatives>>, Dalton Trans., 47, pp. 12373-12384, 2018.

[16] X. Liu, H. Nan, W. Sun, Q. Zhang, M. Zhan, L. Zou, Z. Xie, X. Li, C. Lu, Y. Cheng, <<Synthesis and characterisation of neutral mononuclear cuprous complexes based on dipyrrin derivatives and phosphine mixed-ligands>>, Dalton Trans., 41, pp. 10199-10210, 2012.

What is claimed is:

1. An iridium compound of formula 1, 2, 3 or 4:

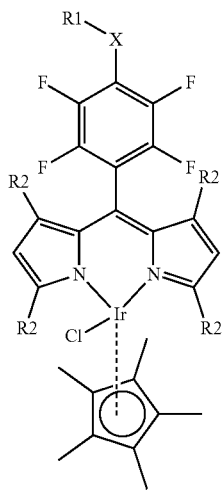

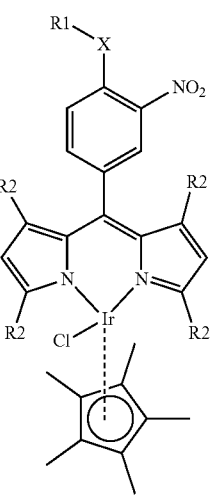

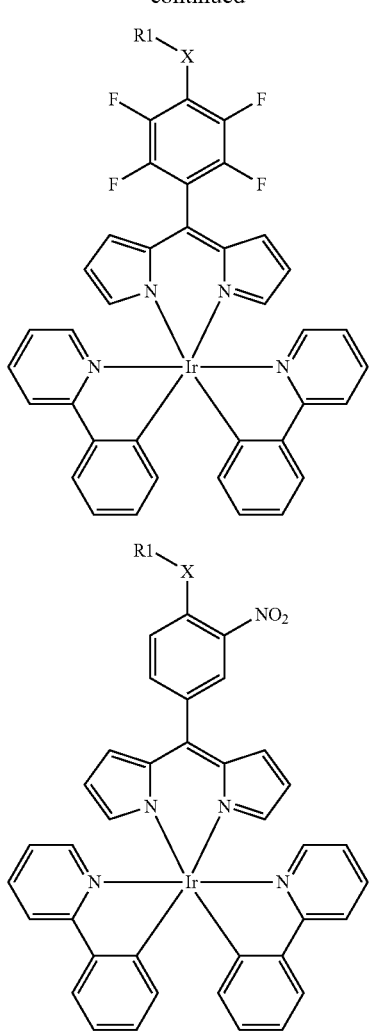

Wherein:

X is at least one of O, NH or S;

R¹ is at least one of a carbohydrate moiety, a short alkyl chain with 3 to 6 carbon atoms, propargyl, HO—CH$_2$—CH$_2$—, CH(CH$_2$OH)$_2$, CH$_2$—CH(OH)—CH$_2$OH, or CH(OH)—CH(OH)—CH$_3$; and R² is at least one of hydrogen or a methyl group.

2. The compound of claim 1 for use in tumor therapy.

3. The compound of claim 1 for use in photodynamic therapy.

4. The compound of claim 1 for use in the therapy of at least one of tumors, dermatological disorders, viral infections, bacterial infections, otorhinolaryngology disorders, ophthalmological disorders or urological disorders.

5. The compound of claim 1 for use in the photodynamic therapy of at least one of tumors, dermatological disorders, viral infections, bacterial infections, otorhinolaryngology disorders, ophthalmological disorders or urological disorders.

6. A compound of claim 1 as a component in the preparation of a pharmaceutical composition for tumor therapy or photodynamic tumor therapy.

7. The compound of claim 1 for use in the therapy or photodynamic therapy of arthritis and inflammatory diseases.

8. The compound of claim 1 for use in the diagnosis of arthritis and inflammatory diseases or in the diagnosis of tumors.

9. The compound of claim 1 when loaded onto a surface of a medical device.

10. A pharmaceutical composition comprising a compound according to claim 1 as an active ingredient.

11. The pharmaceutical composition of claim 10, wherein the compound is conjugated to a targeting agent.

12. The pharmaceutical composition of claim 11, wherein the targeting agent is a peptide.

* * * * *